(12) United States Patent
Oronsky et al.

(10) Patent No.: US 12,109,348 B2
(45) Date of Patent: Oct. 8, 2024

(54) MEDICATION INFUSION DEVICES, SYSTEMS, AND METHODS

(71) Applicant: EpicentRx, Inc., La Jolla, CA (US)

(72) Inventors: Bryan T. Oronsky, Los Altos Hills, CA (US); Scott Caroen, San Francisco, CA (US)

(73) Assignee: EPICENTRX, INC., La Jolla, CA (US)

( * ) Notice: Subject to any disclaimer, the term of this patent is extended or adjusted under 35 U.S.C. 154(b) by 330 days.

(21) Appl. No.: 17/119,423

(22) Filed: Dec. 11, 2020

(65) Prior Publication Data

US 2021/0178050 A1    Jun. 17, 2021

Related U.S. Application Data

(60) Provisional application No. 62/946,856, filed on Dec. 11, 2019, provisional application No. 62/946,858, filed on Dec. 11, 2019.

(51) Int. Cl.
*A61M 1/36* (2006.01)
*A61M 1/38* (2006.01)

(52) U.S. Cl.
CPC ...... *A61M 1/3673* (2014.02); *A61M 1/36225* (2022.05); *A61M 1/362266* (2022.05);
(Continued)

(58) Field of Classification Search
CPC .... A61M 1/34; A61M 1/3696; A61M 1/3626; A61M 1/303; A61M 1/308; A61M 1/302;
(Continued)

(56) References Cited

U.S. PATENT DOCUMENTS 2,910,981 A    11/1959    Wilson et al.
4,865,583 A    9/1989    Tu
(Continued)

FOREIGN PATENT DOCUMENTS

CN    101299998 A    11/2008
CN    101380491 A    3/2009
(Continued)

OTHER PUBLICATIONS

Extended European Search Report and Written Opinion received for European Patent Application No. 19819790.7 mailed on Mar. 10, 2022, 7 pages.
(Continued)

*Primary Examiner* — Benjamin L Lebron
(74) *Attorney, Agent, or Firm* — Morrison & Foerster LLP

(57) ABSTRACT

Devices, systems, and methods for medication infusion are described herein. In some embodiments, a system includes a patient access subassembly, a first fluid reservoir, a second fluid reservoir, and an assembly. The assembly can have a first configuration in which the patient access subassembly is in fluid communication with the first fluid reservoir via a first tube, a second configuration in which the first fluid reservoir is in fluid communication with the second fluid reservoir, and a third configuration in which the first fluid reservoir is in fluid communication with the patient access subassembly via a second tube, the first fluid reservoir fluidically isolated from the first tube in the third configuration.

23 Claims, 41 Drawing Sheets

(52) U.S. Cl.
CPC ....... *A61M 1/38* (2013.01); *A61M 2202/0007* (2013.01); *A61M 2202/0216* (2013.01); *A61M 2202/0275* (2013.01); *A61M 2202/0427* (2013.01); *A61M 2202/0429* (2013.01); *A61M 2202/0439* (2013.01); *A61M 2205/75* (2013.01)

(58) Field of Classification Search
CPC .............. A61M 1/3683; A61M 1/3681; A61M 1/1692; A61M 1/3693; A61M 1/3673; A61M 1/38; A61M 2202/0007; A61M 2202/0216; A61M 2202/0275; A61M 2202/0427; A61M 2202/0429; A61M 2202/0439; A61M 2205/75
See application file for complete search history.

(56) References Cited

U.S. PATENT DOCUMENTS

| | | |
|---|---|---|
| 5,015,226 A | 5/1991 | Polaschegg |
| 5,378,227 A | 1/1995 | O'Riordan et al. |
| 6,709,413 B1 | 3/2004 | Chance et al. |
| 7,488,309 B2 | 2/2009 | Kissinger et al. |
| 7,507,842 B2 | 3/2009 | Bednarski et al. |
| 8,299,053 B2 | 10/2012 | Bednarski et al. |
| 8,927,527 B2 | 1/2015 | Bednarski et al. |
| 10,155,082 B2 * | 12/2018 | Roger ..................... A61M 1/34 |
| 2004/0054320 A1 | 3/2004 | Kissinger et al. |
| 2005/0049539 A1 * | 3/2005 | O'Hara ............... A61M 1/3696 604/4.01 |
| 2006/0079809 A1 | 4/2006 | Goldberger et al. |
| 2007/0225675 A1 | 9/2007 | Robinson et al. |
| 2010/0100027 A1 | 4/2010 | Schilthuizen et al. |
| 2010/0305507 A1 | 12/2010 | Duncan |
| 2012/0065502 A1 | 3/2012 | Levy et al. |
| 2013/0023813 A1 | 1/2013 | Roorda |
| 2013/0040797 A1 | 2/2013 | Lindner et al. |
| 2014/0107480 A1 | 4/2014 | Spohn et al. |
| 2017/0072134 A1 | 3/2017 | Fish et al. |
| 2018/0078699 A1 | 3/2018 | Prendergast et al. |
| 2018/0133416 A1 | 5/2018 | Silver et al. |
| 2018/0147335 A1 | 5/2018 | Nilsson |
| 2020/0188571 A1 | 6/2020 | Gipson |
| 2021/0244870 A1 | 8/2021 | Oronsky et al. |

FOREIGN PATENT DOCUMENTS

| | | | |
|---|---|---|---|
| CN | 101808681 A | 8/2010 | |
| CN | 102548521 A | 7/2012 | |
| CN | 103561798 A | 2/2014 | |
| CN | 106573098 A | 4/2017 | |
| CN | 107735140 A | 2/2018 | |
| JP | S63-281653 A | 11/1988 | |
| JP | H01-113069 A | 7/1989 | |
| JP | 2001198225 A | 7/2001 | |
| JP | 2014514052 A | 6/2014 | |
| TW | 200403086 A | 3/2004 | |
| WO | WO-9622117 A2 * | 7/1996 | .......... A61M 1/1692 |
| WO | WO-1996022117 A2 | 7/1996 | |
| WO | WO-2017123593 A1 | 7/2017 | |

OTHER PUBLICATIONS

International Search Report and Written Opinion received for International Patent Application No. PCT/US2019/036588 mailed on Sep. 4, 2019, 11 pages.

* cited by examiner

400

402 — Fluidically coupling a first coupling member of a first subassembly to a valve assembly of a second subassembly, the second subassembly including a first fluid reservoir and a second fluid reservoir fluidically coupled to the valve subassembly, the first fluid reservoir selectively fluidically coupled to the second fluid reservoir via the valve assembly, the first subassembly including a patient access port, a first coupling member, and a second coupling member, the first coupling member and the second coupling member in fluid communication with the patient access port, the first coupling member coupled to the valve assembly such that the first fluid reservoir of the second subassembly is in selective fluid communication with the patient access port via a first flow path 404 — Fluidically coupling the second coupling member of the first subassembly to the valve assembly such that the first fluid reservoir is in selective fluid communication with the patient access port via a second flow path different from the first flow path 406 — Coupling a third fluid reservoir to the valve assembly such that the third fluid reservoir is in selective fluid communication with the patient access port via the second flow path

FIG. 4

MEDICATION INFUSION DEVICES, SYSTEMS, AND METHODS

CROSS-REFERENCE TO RELATED APPLICATIONS

This application claims priority to U.S. Provisional Patent Application No. 62/946,856, titled "Medication Infusion Devices, Systems, and Methods," filed Dec. 11, 2019 and U.S. Provisional Patent Application No. 62/946,858, titled "Medication Infusion Devices, Systems, and Methods," filed Dec. 11, 2019, the disclosures of both of which are incorporated herein by reference in their entireties.

FIELD OF THE INVENTION

Embodiments described herein relate to devices, systems, and methods for combining medication with biological fluids of a patient ex vivo (i.e., outside of the body of the patient) and reinfusing the combination to the patient. In particular, embodiments described herein relate to medication infusion devices, systems, and methods for combining medication with blood of a patient ex vivo and reinfusing the combined medication and blood to the patient.

BACKGROUND

Some types of medication, such as some used for chemotherapy, cause pain and other side effects when delivered intravenously to a patient. For example, some medications may release nitric oxide during infusion that causes a severe burning sensation to the patient. These medications may be necessary to treat a patient suffering from various medical issues, such as cancer. Thus, the rate of infusion is often decreased to mitigate the pain associated with the infusion, which results in long infusion durations (e.g., over 8 hours). Long infusion durations, however, reduce the number of patients that are treatable in a clinical setting whether in a private practice, a group practice, or a hospital-based clinic during routine working hours. Long infusion durations are not only time-consuming and uncomfortable for individual patients but also increase the risk of infection.

Thus, there is a need for devices, systems, and methods that can reduce or eliminate the pain and other side effects related to the delivery of medication to the patient's vasculature while allowing for reduced administration periods.

SUMMARY

Systems, apparatus, and methods for extracorporeal medication infusion are described herein. In some embodiments, an extracorporeal blood device may include a venous or arterial blood line for removing blood from a patient, treating the blood with a medication, and returning the treated blood to the patient via a filter. For example, in some embodiments, a method includes coupling a patient access subassembly to a patient. The patient access subassembly can be fluidically coupled to a first fluid reservoir containing a first substance and a second fluid reservoir containing a second substance via an assembly. Cells can be drawn through the patient access subassembly, through the assembly, and into the first fluid reservoir such that the cells and the first substance form a third substance. The assembly can be manipulated such that the first fluid reservoir is fluidically isolated from the patient access subassembly and such that the first fluid reservoir is in fluidic communication with the second fluid reservoir. A portion of the third substance can then be transferred from the first fluid reservoir through the assembly and into the second fluid reservoir such that the portion of the third substance and the second substance form a fourth substance. The fourth substance can be transferred from the second fluid reservoir through the assembly and into the first fluid reservoir such that the remainder of the third substance and the fourth substance form a fifth substance. The assembly can be manipulated such that the first fluid reservoir is in fluid communication with the patient access subassembly. The fifth substance can be transferred from the first fluid reservoir through the assembly, through the patient access subassembly, and into the patient. A third fluid reservoir containing a saline solution can be fluidically coupled to the assembly. The assembly can be manipulated such that the third fluid reservoir is in fluid communication with the patient access subassembly via the assembly. At least a portion of the saline solution can be transferred from the assembly to the patient access subassembly.

BRIEF DESCRIPTION OF THE DRAWINGS

FIG. 4 is a flow chart of a method, according to another embodiment.

DETAILED DESCRIPTION

Figure 1:
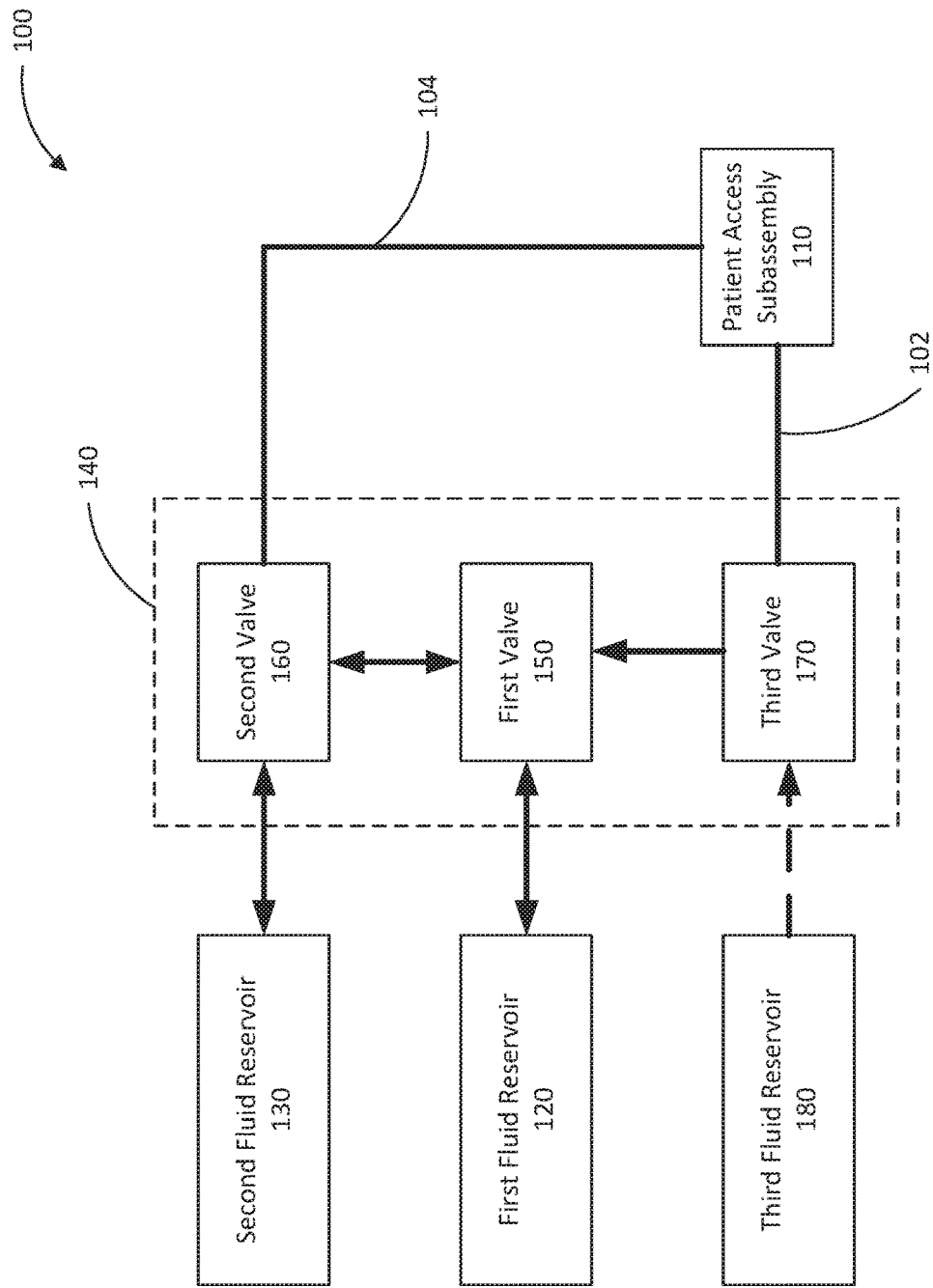
FIG. 1 is a schematic illustration of a system, according to an embodiment.

In some embodiments, the devices, systems, and methods described herein can be used for extracorporeal blood treatment (e.g., with medication). For example, a system or device can be used to draw blood from a patient's vein or artery, combine the blood with one or more medicaments to produce treated blood, and reintroduce the treated blood via a filter (e.g., to trap microbubbles and debris) into the patient. The system or device can be closed or can include a closed circuit to prevent infection of the treated blood. In some embodiments, the system or device can include an inlet line, a stopcock, a reservoir, and an outlet line such that blood can be drawn through the inlet line, the stopcock, and into the reservoir and be returned to the patient from the reservoir, through the stopcock, and through the outlet line. The system or device can include one or more filters disposed before and/or after the stopcock and/or in the blood circuit. Optionally, the system or device can also include one or more secondary fluid reservoirs (e.g., fluid containers and/or bags), each containing one or more of a medicament (e.g., a drug), an anticoagulant, an antioxidant, and/or a flush solution. In some embodiments, the system or device can optionally include a partial deoxygenation device for removal of gases from the treated blood and/or a pumping device for controlling the flow of blood and/or treated blood through the system or device.

In some embodiments, a method includes coupling a patient access subassembly to a patient. The patient access subassembly can be fluidically coupled to a first fluid reservoir containing a first substance and a second fluid reservoir containing a second substance via an assembly. Cells can be drawn through the patient access subassembly, through the assembly, and into the first fluid reservoir such that the cells and the first substance form a third substance. The assembly can be manipulated such that the first fluid reservoir is fluidically isolated from the patient access subassembly and such that the first fluid reservoir is in fluidic communication with the second fluid reservoir. A portion of the third substance can then be transferred from the first fluid reservoir through the assembly and into the second fluid reservoir such that the portion of the third substance and the second substance form a fourth substance. The fourth substance can be transferred from the second fluid reservoir through the assembly and into the first fluid reservoir such that the remainder of the third substance and the fourth substance form a fifth substance. The assembly can be manipulated such that the first fluid reservoir is in fluid communication with the patient access subassembly. The fifth substance can be transferred from the first fluid reservoir through the assembly, through the patient access subassembly, and into the patient. A third fluid reservoir containing a saline solution can be fluidically coupled to the assembly. The assembly can be manipulated such that the third fluid reservoir is in fluid communication with the patient access subassembly via the assembly. At least a portion of the saline solution can be transferred from the assembly to the patient access subassembly. In some embodiments, a kit includes a first assembly including a first fluid reservoir, a second fluid reservoir, a valve assembly, and a first tube. The first fluid reservoir, the second fluid reservoir, and the first tube can be fluidically coupled to the valve assembly. The valve assembly can be configured to selectively allow fluid communication between the first fluid reservoir and the second fluid reservoir and between the first fluid reservoir and the first tube. The kit can also include a second assembly including a patient access port fluidically coupled to a second tube. The second tube can be configured to be fluidically coupled to the valve assembly of the first assembly via a first flow path including a third tube and via a second flow path via the first tube such that the valve assembly can be in fluid communication with the patient access port via the first tube and via the second tube. The kit can further include a third fluid reservoir configured to be coupled to the valve assembly such that the valve assembly can selectively allow fluid communication between the third fluid reservoir and the first tube.

In some embodiments, a method includes fluidically coupling a first coupling member of a first subassembly to a valve assembly of a second subassembly. The second subassembly can include a first fluid reservoir and a second fluid reservoir fluidically coupled to the valve subassembly. The first fluid reservoir can be selectively fluidically coupled to the second fluid reservoir via the valve assembly. The first subassembly can include a patient access port, a first coupling member, and a second coupling member. The first coupling member and the second coupling member can be in fluid communication with the patient access port. The first coupling member can be coupled to the valve assembly such that the first fluid reservoir of the second subassembly is in selective fluid communication with the patient access port via a first flow path. The second coupling member of the first subassembly can be fluidically coupled to the valve assembly such that the first fluid reservoir is in selective fluid communication with the patient access port via a second flow path different from the first flow path. A third fluid reservoir can be coupled to the valve assembly such that the third fluid reservoir is in selective fluid communication with the patient access port via the second flow path.

In some embodiments, an apparatus includes a patient access subassembly, a first fluid reservoir, a second fluid reservoir, and an assembly. The first fluid reservoir can be configured to contain a first fluid substance. The second fluid reservoir can be configured to contain a second fluid substance. The assembly can have a first configuration in which the patient access subassembly is in fluid communication with the first fluid reservoir via a first tube, a second configuration in which the first fluid reservoir is in fluid communication with the second fluid reservoir, and a third configuration in which the first fluid reservoir is in fluid communication with the patient access subassembly via a second tube. The first fluid reservoir can be fluidically isolated from the first tube in the third configuration.

In some embodiments, an apparatus includes a patient access subassembly, a first fluid reservoir, a second fluid reservoir, and an assembly. The patient access subassembly can be configured to provide access to a blood vessel of a patient. The first fluid reservoir can be configured to contain a first fluid substance. The second fluid reservoir can be configured to contain a second fluid substance. The assembly can include a first valve, a second valve, and a third valve. The first fluid reservoir can be in selective fluid communication with the second fluid reservoir via the first valve and the second valve. The patient access subassembly can be in selective fluid communication with the first fluid reservoir via the first valve. The third valve can be configured to be coupled to a third fluid reservoir such that the third fluid reservoir is in selective fluid communication with the patient access subassembly via the first valve and the second valve.

In some embodiments, the medicament described herein can include any suitable medicament or therapeutic agent, such as any of the medicaments or therapeutic agents described in U.S. Pat. Nos. 7,507,842; 8,299,053; and/or 8,927,527; and/or in International Publication No. WO/2017/123593A1, the contents of each of which are hereby incorporated by reference. For example, the medicament can include 2-Bromo-1-(3,3-dinitroazetidin-1-yl)ethanone. In another example, the medicament can include propofol (also referred to as Diprivan). In another example, the medicament can include ozone. In another example, the medicament can include nitric oxide. For example, the medicament can include nitric oxide donors such as sildenafil (also referred to as VIAGRA®), tadalafil (also referred to as CIALIS®) vardenafil (also referred to as Levitra®), and/or nitrate esters such as nitroglycerin, sodium nitrite, and/or sodium nitrate. In another example, the medicament can include electrophiles that can bind to sulhydryl groups (e.g., a sulfhydryl-reactive alkylating agent) such as maleimide, iodoacetate, iodoacetic acid, bromoacetate, bromoacetic acid, iodoacetamide, chloroacetamide, acrylate, and/or bromoacetamide. In another example, the medicament can include a chemotherapy drug (e.g., antitumor platinum coordination complexes, antimetabolites, mitotic inhibitors, anticancer antibiotics, topoisomerase I and/or II inhibitors, proteasome inhibitors, histone deacetylase inhibitors, nitrogen mustard alkylating agents, nitrosourea alkylating agents, nonclassical alkylating agents, estrogen antagonists, androgen antagonists, mTOR inhibitors, and/or tyrosine kinase inhibitors), FIG. 1 is a schematic illustration of a system 100. In some embodiments, the system 100 is useful for drawing cells (e.g., packed red blood cells, white blood cells, and/or platelets) from a patient, combining medicament with the cells of the patient ex vivo, and infusing the combined cells and medicament into the patient's bloodstream. The system 100 includes a patient access subassembly 110, a first fluid reservoir 120, a second fluid reservoir 130, a third fluid reservoir 180, and an assembly 140. The assembly 140 can include a first valve 150, a second valve 160, and a third valve 170. The first fluid reservoir 120 can be coupled to the first valve 150 and the second fluid reservoir 130 can be coupled to the second valve 160. In some embodiments, the third valve 170, the first valve 150, and the second valve 160 can be arranged in series. In some embodiments, the first valve 150 can be engaged with the third valve 170 and the second valve 160. In some embodiments, the first valve 150 can be fluidically coupled to the third valve 170 and the second valve 160 via, for example, interconnecting tubing. The third fluid reservoir 180 can be coupled to the third valve 170. In some embodiments, the third fluid reservoir 180 can be separate from the assembly 140 during a portion of the use of the system 100 (e.g., during initial blood draw through the first tube 102 and/or transfer between the first fluid reservoir 120 and the second fluid reservoir 130).

The patient access subassembly 110 can be coupled to the third valve 170 via a first tube 102, such that the patient access subassembly 110 can be in fluid communication with the third valve 170 via a first fluid route. The patient access subassembly 110 can be coupled to the second valve 160 via a second tube 104 such that the patient access subassembly 110 can be in fluid communication with the second valve 160 via a second fluid route. Thus, in some embodiments, the system 100 can function as a closed loop system in which fluid can flow away from the patient access subassembly 110 via the first tube 102 and return to the patient access subassembly 110 via the second tube 104.

In an example use scenario, the second fluid reservoir 130 can include medicament, such as 2-Bromo-1-(3,3-dinitroazetidin-1-yl)ethanone, a dinitroazetidine, propofol, a nitric oxide donor, sulfhydryl-reactive alkylating agents, and/or ozone. The system 100 can be attached to a patient via the patient access subassembly 110. A volume of blood of the patient can be drawn through the patient access subassembly 110, through the first tube 102, through the assembly 140, and into the first fluid reservoir 120. A portion of the volume of blood drawn can be transferred to the second fluid reservoir 130 via the assembly 140 such that the portion combines with the medicament in the second fluid reservoir 130 to form a first combined substance. The first combined substance can then be returned to the first fluid reservoir 120 via the assembly 140 to combine with the remaining blood in the first fluid reservoir 120 to form a second combined substance. The second combined substance can then be pushed through the assembly 140, through the second tube 104, and through the patient access subassembly 110 such that the second combined substance flows into the bloodstream of the patient.

Each of the first valve 150, the second valve 160, and the third valve 170 can be configured to transition between two or more configurations, with each configuration corresponding to a different flow path. Each of the first valve 150, the second valve 160, and the third valve 170 can include any suitable valve mechanism, such as, for example, a manual valve mechanism, a solenoid-actuated valve mechanism, a motor-operated valve mechanism, a hydraulic valve mechanism, and/or a pneumatic valve mechanism. For example, each of the first valve 150, the second valve 160, and the third valve 170 can include a three-way stopcock. Each of the first valve 150, the second valve 160, and the third valve 170 can define or include an interior region such that fluid can travel through the interior region. The first fluid reservoir 120 can be coupled to the first valve 150 such that the first fluid reservoir 120 can be in selective fluid communication with the patient access subassembly 110 via the third valve 170 and the first valve 150, the second fluid reservoir 130 via the first valve 150 and the second valve 160, or the second tube 104 via the first valve 150 and the second valve 160. For example, the first valve 150 can have a first configuration in which the first valve 150 allows fluid communication between an interior region of the third valve 170 and the first fluid reservoir 120, but fluidically isolates an interior region of the second valve 160 from both the first fluid reservoir 120 and the interior region of the third valve 170. The first valve 150 can have a second configuration in which the first valve 150 allows fluid communication between the first fluid reservoir 120 and an interior region of the second valve 160, but fluidically isolates the interior region of the third valve 170 from both the first fluid reservoir 120 and the interior region of the second valve 160. The first valve 150 can have a third configuration in which the first valve 150 allows fluid communication between the interior region of the third valve 170 and the interior region of the second valve 160, but fluidically isolates the first fluid reservoir 120 from both the interior region of the third valve 170 and the interior region of the second valve 160.

In some embodiments, the second fluid reservoir 130 can be coupled to the second valve 160 such that the second fluid reservoir 130 can be in selective fluid communication with the first fluid reservoir 120 via the second valve 160 and the first valve 150 and with the patient access subassembly 110 via the second valve 160. For example, the second valve 160 can have a first configuration in which the second valve 160 allows fluid communication between the interior region of the first valve 150 and the second fluid reservoir 130, but fluidically isolates the second tube 104 from both the second fluid reservoir 130 and the interior region of the first valve 150. The second valve 160 can have a second configuration in which the second valve 160 allows fluid communication between the interior region of the first valve 150 and the second tube 104, but fluidically isolates the second fluid reservoir 130 from both the interior region of the first valve 150 and the second tube 104.

The third valve 170 can be coupled to the first valve 150 such that the patient access subassembly 110 and the third fluid reservoir 180 can each be in selective fluid communication with the first fluid reservoir 120 and/or the second tube 104 via the third valve 170. For example, the third valve 170 can have a first configuration in which the third valve 170 allows fluid communication between the first tube 102 and the interior region of the first valve 150, but fluidically isolates the third fluid reservoir 180 (or a connector configured to be coupled to the third fluid reservoir 180) from both the first tube 102 and the interior region of the first valve 150. The third valve 170 can have a second configuration in which the third valve 170 allows fluid communication between the third fluid reservoir 180 and the interior region of the first valve 150, but fluidically isolates the first tube 102 from both the interior region of the first valve 150 and the third fluid reservoir 180.

Thus, the assembly 140 can have a first assembly configuration in which the patient access subassembly 110 is in fluid communication with the first fluid reservoir 120 via the first tube 102, a second assembly configuration in which the first fluid reservoir 120 is in fluid communication with the second fluid reservoir 130, and a third assembly configuration in which the first fluid reservoir 120 is in fluid communication with the patient access subassembly 110 via the second tube 104. In the first assembly configuration, the first valve 150 can be in the first configuration of the first valve 150 and the third valve 170 can be in the first configuration of the third valve 170 such that the first tube 102 and the first fluid reservoir 120 can be in fluid communication via the third valve 170 and the first valve 150. In the first assembly configuration, the second valve 160 can be in either the first or second configuration of the second valve 160 because the second valve 160 is isolated from the flow path from the patient access subassembly 110, through the first tube 102, the third valve 170, the first valve 150, and into the first fluid reservoir 120.

In the second assembly configuration, the first valve 150 can be in the second configuration of the first valve 150 and the second valve 160 can be in the first configuration of the second valve 160 such that the first fluid first reservoir 120 and the second fluid reservoir 130 are in fluid communication via the first valve 150 and the second valve 160. The third valve 170 can be in either the first or second configuration of the third valve 170 because the third valve 170 is isolated from the flow path between the first fluid reservoir 120 and the second fluid reservoir 130 via the first valve 150 and the second valve 160.

In the third assembly configuration, the first valve 150 can be in the third configuration of the first valve 150 and the second valve 160 can be in the second configuration of the second valve 160 such that the first fluid reservoir 120 can be in fluid communication with the second tube 104. The third valve 170 can be in either the first or second configuration of the third valve 170 because the third valve 170 is isolated from the flow path between the first fluid reservoir 120 and the second tube 104 via the first valve 150 and the second valve 160.

In some embodiments, the assembly 140 can have a fourth assembly configuration in which the third fluid reservoir 180 is in fluid communication with the second tube 104. In the fourth assembly configuration, the first valve 150 can be in the third configuration of the first valve 150, the second valve 160 can be in the second configuration of the second valve 160, and the third valve 170 can be in the second configuration of the third valve 170, such that the third fluid reservoir 180 is in fluid communication with the second tube 104 (and the patient access subassembly 110) via the third valve 170, the first valve 150, and the second valve 160. In the fourth assembly configuration, the flow path from the third fluid reservoir 180 to the second tube 104 can be fluidically isolated from the first tube 102, the first fluid reservoir 120, and the second fluid reservoir 130.

The first fluid reservoir 120, the second fluid reservoir 130, and/or the third fluid reservoir 180 can be defined or included in any suitable fluid containing component. For example, in some embodiments, the system 100 can include a number of syringes such that the first fluid reservoir 120, the second fluid reservoir 130, and/or the third fluid reservoir 180 are each defined by a syringe having a barrel and a plunger, such that fluid can be drawn into and expelled from each of the fluid reservoirs via, for example, translation of the respective plunger. In some embodiments, the system 100 can include one or more gas syringes. For example, the second fluid reservoir 130 can be a gas syringe. In some embodiments, the system 100 can include a number of fluid bags such that the first fluid reservoir 120, the second fluid reservoir 130, and/or the third fluid reservoir 180 can each be defined by a fluid bag such that fluid can be drawn into and/or expelled from each of the fluid reservoirs via, for example, squeezing a respective fluid bag, a pump, and/or gravitational effects on the fluid. In some embodiments, the system 100 can include a combination of one or more syringes and one or more fluid bags such that one or more of the first fluid reservoir 120, the second fluid reservoir 130, and/or the third fluid reservoir 180 can be defined by a syringe and one or more of the others can be defined by a fluid bag.

In some embodiments, the first fluid reservoir 120 can include (e.g., be prefilled with) an anti-coagulant, such as, for example, ACD-A, ACD-B, EDTA, or heparin. In some embodiments, the first fluid reservoir 120 can be prefilled with both an anti-coagulant and an antioxidant (e.g., vitamin C or N-acetylcysteine). In some embodiments, the second fluid reservoir 130 can include (e.g., be prefilled with) a medicament, such as, for example, 2-Bromo-1-(3,3-dinitroazetidin-1-yl)ethanone, propofol nitric oxide, and/or ozone. In some embodiments, the third fluid reservoir 180 can include (e.g., be prefilled with) saline.

The patient access subassembly 110 can include any suitable elements configured to provide access to a patient's vasculature system. For example, the patient access subassembly 110 can include a needle, such as, for example, a Huber needle. In some embodiments, the patient access subassembly 110 can include a connector configured to couple to a port coupled to the patient's vasculature system. The patient access subassembly 110 can also include a connector such that the patient's vasculature can be in fluid communication with the first tube 102 and/or the second tube 104. For example, the patient access subassembly 110 can include a connector configured to couple to the first tube 102, the second tube 104, and the patient vasculature system via, for example, a third tube coupled to a needle or port. For example, in some embodiments, the connector of the patient access subassembly 110 can be configured to be coupled to a connector disposed on an end of an intravenous tubing line. The intravenous tubing line can be fluidically coupled to the patient's vasculature (e.g., prior to being coupled to the connector of the patient access subassembly 110) such that the patient's vasculature is in fluidic communication with the first tube 102 and the second tube 104 via the patient access subassembly 110.

In use, the first fluid reservoir 120 can be prefilled with a volume of anti-coagulant. The second fluid reservoir 130 can be prefilled with a volume of medicament. The third fluid reservoir 180 can be prefilled with a volume of saline. In some embodiments, the third fluid reservoir 180 can be separate from the assembly 140 during the initial stages of use of the system 100. In some embodiments, the third fluid reservoir 180 can be attached to the assembly 140 prior to the initial stages of use of the system 100 (e.g., prior to coupling the patient access subassembly 110 to the patient's vasculature). In some embodiments, the assembly 140, and/or the second tube 104 can be primed (e.g., filled with saline) prior to coupling the assembly 140 and/or the second tube 104 to the patient access subassembly 110.

The patient access subassembly 110 can be placed in fluid communication with a patient's vasculature (e.g., via inserting a needle of the patient access subassembly 110 through a patient's skin or via coupling the patient access subassembly 110 to an existing port through a patient's skin (e.g., a connector coupled to an intravascular tubing line)). The assembly 140 can be arranged in the first assembly configuration such that the patient access subassembly 110 is in fluid communication with the first fluid reservoir 120 via the first tube 102, the third valve 170, and the first valve 150. For example, the first valve 150 can be manipulated or toggled into the first configuration of the first valve 150 and the third valve 170 can be manipulated or toggled into the first configuration of the third valve 170. Blood can then be drawn from the patient, through the patient access subassembly 110, the first tube 102, the third valve 170, the first valve 150, and into the first fluid reservoir 120 such that the blood combines with the anticoagulant within the first fluid reservoir 120 to form a first substance. For example, a plunger of a syringe defining the first fluid reservoir 120 can be translated relative to a barrel of the syringe to draw blood into the first fluid reservoir 120.

The assembly 120 can then be transitioned to the second assembly configuration such that the first fluid reservoir 120 is in fluid communication with the second fluid reservoir 130. For example, the first valve 150 and the second valve 160 can be manipulated or toggled such that the first valve 150 is in the second configuration of the first valve 150 and the second valve 160 is in the first configuration of the second valve 160. A portion of the first substance (e.g., a volume equal to or greater than the volume of medicament in the second fluid reservoir 130) can then be transferred from the first fluid reservoir 120 to the second fluid reservoir 130 such that the portion of the first substance combines with the medicament within the second fluid reservoir 130 to form a second substance. For example, a plunger of a syringe defining the first fluid reservoir 120 can be translated to expel the portion of the first substance from the first fluid reservoir 120 and push the first substance into the second fluid reservoir 130. In some embodiments, a plunger or a syringe defining the second fluid reservoir 130 can be simultaneously translated relative to a barrel of the syringe to assist in drawing the first substance into the second fluid reservoir 130.

While the assembly 140 remains in the second assembly configuration, the second substance can be transferred from the second fluid reservoir 130 to the first fluid reservoir 120 such that the second substance combines with the remaining portion of the first substance in the first fluid reservoir 120 to form a third substance. For example, a plunger of a syringe defining the second fluid reservoir 130 can be translated to expel the second substance from the second fluid reservoir 130 and push the second substance into the first fluid reservoir 120. In some embodiments, a plunger or a syringe defining the first fluid reservoir 120 can be simultaneously translated relative to a barrel of the syringe to assist in drawing the second substance into the first fluid reservoir 120.

The assembly 140 can then be transitioned to the third assembly configuration such that the first fluid reservoir 120 is in fluid communication with the patient access subassembly 110 via the first valve 150, the second valve 160, and the second tube 104. For example, the first valve 150 can remain in the second configuration of the first valve 150 and the second valve 160 can be manipulated or toggled such that the second valve 160 is in the second configuration of the second valve 160. The third substance can then be transferred from the first fluid reservoir 120 to the patient's vasculature system via the first valve 150, the second valve 160, the second tube 104, and the patient access subassembly 110.

After transferring the third substance to the patient's vasculature, the third fluid reservoir 180 can be coupled to the third valve 170. The assembly 140 can then be transitioned to the fourth assembly configuration such that the third fluid reservoir 180 is in fluid communication with the patient access subassembly 110 via the third valve 170, the first valve 150, the second valve 160, and the second tube 104. For example, the first valve 150 can be manipulated or toggled such that the first valve 150 is in the third configuration of the first valve 150, the second valve 160 can remain in the second configuration of the second valve 160, and the third valve 170 can be manipulated or toggled such that the third valve 170 is in the second configuration of the third valve 170. The contents of the third fluid reservoir 180 (i.e., saline) can then be transferred to the patient access subassembly 110 via the third valve 170, the first valve 150, the second valve 160, and the second tube 104 such that the saline flushes the fluid flow path of the third substance. The system 100 can then be detached from the patient.

In some embodiments, the system 100 can optionally include an actuation subsystem (not shown). The actuation subsystem can include one or more actuators configured to engage with one or more of the components of the system 100. For example, rather than manually adjusting a configuration or orientation of a valve of the assembly 140, an actuator can engage and adjust the configuration of orientation of the valve of the assembly 140. In some embodiments, the actuation subsystem can include a first actuator operably coupled to the first valve 150, a second actuator operably coupled to the second valve 160, and a third actuator operably coupled to the third valve 170. Each of the first actuator, the second actuator, and the third actuator can be configured to transition (e.g., manipulate or toggle) the first valve 150, the second valve 160, and the third valve 170, respectively, between their respective operating configurations. The actuation subsystem can also include a first reservoir actuator configured to control the flow of fluid into and out of the first fluid reservoir, a second reservoir actuator configured to control the flow of fluid into and out of the second fluid reservoir, and a third reservoir actuator configured to control the flow of fluid into and out of the third fluid reservoir.

In some embodiments, rather than including an actuation subsystem, the system 100 can optionally be coupleable to a separate actuation system (not shown). For example, the actuation system can include a housing and a number of actuators, each configured to operably engage and/or control a configuration of a valve or a flow of fluid relative to a reservoir of the system 100. The actuation system can be configured to receive the system 100 such that the actuation system can operably engage the system 100 and control operation of the system 100 to perform any of the methods steps described herein. In some embodiments, the system 100 can be disposable and the actuation system can be reusable.

Figure 2:
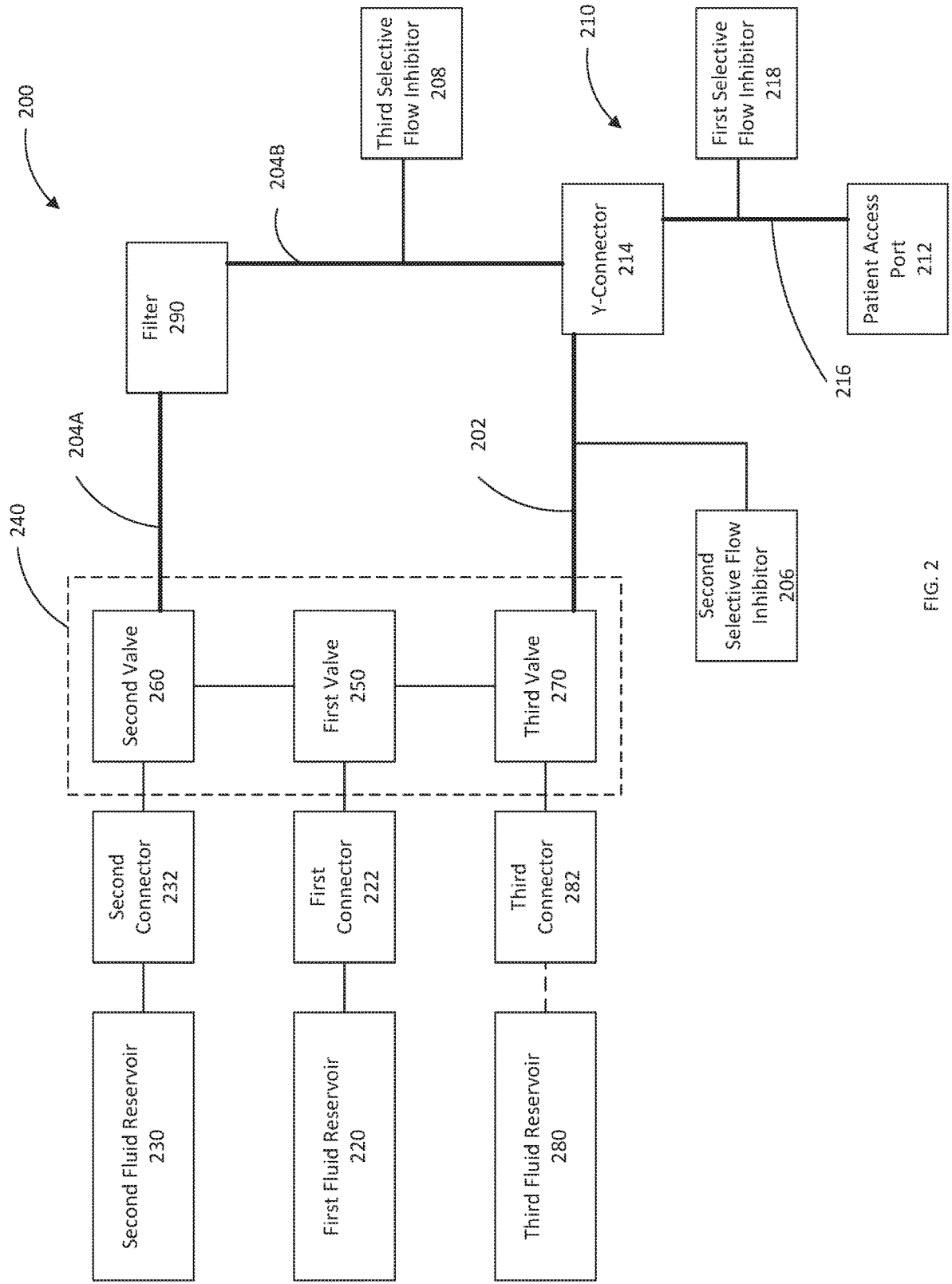
FIG. 2 is a schematic illustration of a system, according to another embodiment.

FIG. 2 is a schematic illustration of a system 200. Unless explicitly noted otherwise, similarly named and referenced components can be structurally and/or functionally similar to those described above with reference to FIG. 1. In some embodiments, the system 200 is useful for drawing cells (e.g., packed red blood cells, white blood cells, and/or platelets) from a patient, combining medicament with the cells of the patient ex vivo, and infusing the combined cells and medicament into the patient's bloodstream. The system 200 includes a patient access subassembly 210, a first fluid reservoir 220, a second fluid reservoir 230, a third fluid reservoir 280, and an assembly 240. The assembly 240 can include a first valve 250, a second valve 260, and a third valve 270. In some embodiments, the assembly 240 can be a 3-gang valve manifold having three levers such that each lever controls the configuration of a valve of the valve manifold. The first fluid reservoir 220 can be coupled to the first valve 250 via a first connector 222 and the second fluid reservoir 230 can be coupled to the second valve 260 via a second connector 232. In some embodiments, the first valve 250 can be engaged with the third valve 270 and the second valve 260. In some embodiments, the first valve 250 can be fluidically coupled to the third valve 270 and the second valve 260 via, for example, interconnecting tubing. The third fluid reservoir 280 can be coupled to the third valve 270 via a third connector 282. In some embodiments, the third fluid reservoir 280 can be separate from the assembly 240 during a portion of the use of the system 200. The first connector 232, the second connector 222, and/or the third connector 282 can be needleless connectors (also referred to as needle free connectors). The system 200 can also include a first tube 202, a second tube 204A, a third tube 204B, and a filter 290, the second tube 204A coupled to the second valve 260 and the filter 290, the third tube 204B coupled to the patient access subassembly 210 and the filter 290. In some embodiments, the filter 290 can have, for example, a pore size of 150 microns. In some embodiments, the filter 290 can have, for example, a pore size of 170 microns to 260 microns, including all values and sub ranges in between. The filter 290 can be used to filter sediment such that the sediment is prevented from flowing into the patient via the patient access subassembly 210. For example, in some embodiments, the filter 290 can prevent an embolism (e.g., by filtering clots and/or clumps of platelets and white blood cells, air blood bubbles, and/or hemoglobin that, for example, may have been released from lysed red cells).

The patient access subassembly 210 can include a patient access port 212, access tubing 216, and a connector 214. The patient access port 212 can include any suitable element configured to provide access to a patient's vasculature system. For example, the patient access subassembly 210 can include a needle, such as, for example, a Huber needle. In some embodiments, the patient access subassembly 210 can include a connector configured to couple to a port previously coupled to the patient's vasculature system. The connector 214 of the patient access subassembly 210 can be coupled to the third valve 270 via the first tube 202 such that the patient access subassembly 210 can be in fluid communication with the third valve 270 via a first fluid route. In some embodiments, the patient access subassembly 210 includes the first tube 202. The connector 214 can be coupled to the second valve 260 via a second fluid route including the second tube 204A, the third tube 204B, and the filter 290 such that the patient access subassembly 210 can be in fluid communication with the second valve 260 via the second fluid route. In some embodiments, the connector 214 can be, for example, a Y-connector. Thus, in some embodiments, the system 200 can function as a closed loop system in which fluid can flow away from the patient access subassembly 210 via the first tube 202 and return to the patient access subassembly 210 via the second tube 204A, the filter 290, and the third tube 204B.

In an example use scenario, the second fluid reservoir 230 can include medicament, such as 2-Bromo-1-(3,3-dinitroazetidin-1-yl)ethanone, propofol, a nitric oxide donor, a chemotherapy drug (e.g., antitumor platinum coordination complexes, antimetabolites, mitotic inhibitors, anticancer antibiotics, topoisomerase I and/or II inhibitors, proteasome inhibitors, histone deacetylase inhibitors, nitrogen mustard alkylating agents, nitrosourea alkylating agents, nonclassical alkylating agents, estrogen antagonists, androgen antagonists, mTOR inhibitors, and/or tyrosine kinase inhibitors), and/or ozone. The system 200 can be attached to a patient via the patient access subassembly 210. A volume of blood of the patient can be drawn through the patient access subassembly 210, through the first tube 202, through the assembly 240, and into the first fluid reservoir 220. A portion of the volume of blood drawn can be transferred to the second fluid reservoir 230 via the assembly 240 such that the portion combines with the medicament in the second fluid reservoir 230 to form a first combined substance. The first combined substance can then be returned to the first fluid reservoir 220 via the assembly 240 to combine with the remaining blood in the first fluid reservoir 220 to form a second combined substance. The second combined substance can then be pushed through the assembly 240, through the second tube 204A, through the filter 290, through the third tube 204B, and through the patient access subassembly 210 such that the second combined substance flows into the bloodstream of the patient.

Each of the first valve 250, the second valve 260, and the third valve 270 can be configured to transition between two or more configurations, each configuration corresponding to a different available flow path through the assembly 240. Each of the first valve 250, the second valve 260, and the third valve 270 can include any suitable valve mechanism, such as, for example, a manual valve mechanism, a solenoid-actuated valve mechanism, a motor-operated valve mechanism, a hydraulic valve mechanism, and/or a pneumatic valve mechanism. For example, each of the first valve 250, the second valve 260, and the third valve 270 can include a three-way stopcock. Each of the first valve 250, the second valve 260, and the third valve 270 can define or include an interior region such that fluid can travel through the interior region. The first fluid reservoir 220 can be coupled to the first valve 250 such that the first fluid reservoir 220 can be in selective fluid communication with the patient access subassembly 210 via the third valve 270 and the first valve 250, the second fluid reservoir 230 via the first valve 250 and the second valve 260, or the second tube 204 via the first valve 250 and the second valve 260. For example, the first valve 250 can have a first configuration in which the first valve 250 allows fluid communication between an interior region of the third valve 270 and the first fluid reservoir 220, but fluidically isolates an interior region of the second valve 260 from both the first fluid reservoir 220 and the interior region of the third valve 270. The first valve 250 can have a second configuration in which the first valve 250 allows fluid communication between the first fluid reservoir 220 and the interior region of the second valve 260, but fluidically isolates the interior region of the third valve 270 from both the first fluid reservoir 220 and the interior region of the second valve 260. The first valve 250 can have a third configuration in which the first valve 250 allows fluid communication between the interior region of the third valve 270 and the interior region of the second valve 260, but fluidically isolates the first fluid reservoir 220 from both the interior region of the third valve 270 and the interior region of the second valve 260.

In some embodiments, the second fluid reservoir 230 can be coupled to the second valve 260 such that the second fluid reservoir 230 can be in selective fluid communication with the first fluid reservoir 220 via the second valve 260 and the first valve 250 and with the patient access subassembly 210 via the second valve 260. For example, the second valve 260 can have a first configuration in which the second valve 260 allows fluid communication between an interior region of the first valve 250 and the second fluid reservoir 230, but fluidically isolates the second tube 204A from both the second fluid reservoir 230 and the interior region of the first valve 250. The second valve 260 can have a second configuration in which the second valve 260 allows fluid communication between the interior region of the first valve 250 and the second tube 204A, but fluidically isolates the second fluid reservoir 230 from both the interior region of the first valve 250 and the second tube 204A.

The third valve 270 can be coupled to the first valve 250 such that the patient access subassembly 210 and the third fluid reservoir 280 can each be in selective fluid communication with the first fluid reservoir 220 and/or the second tube 204A via the third valve 270. For example, the third valve 270 can have a first configuration in which the third valve 270 allows fluid communication between the first tube 202 and the interior region of the first valve 250, but fluidically isolates the third fluid reservoir 280 (or a connector configured to be coupled to the third fluid reservoir 280) from both the first tube 202 and the interior region of the first valve 250. The third valve 270 can have a second configuration in which the third valve 270 allows fluid communication between the third fluid reservoir 280 and the interior region of the first valve 250, but fluidically isolates the first tube 202 from both the interior region of the first valve 250 and the third fluid reservoir 280.

Thus, the assembly 240 can have a first assembly configuration in which the patient access subassembly 210 is in fluid communication with the first fluid reservoir 220 via the first tube 202, a second assembly configuration in which the first fluid reservoir 220 is in fluid communication with the second fluid reservoir 230, and a third assembly configuration in which the first fluid reservoir 220 is in fluid communication with the patient access subassembly 210 via the second tube 204A. In the first assembly configuration, the first valve 250 can be in the first configuration of the first valve 250 and the third valve 270 can be in the first configuration of the third valve 270 such that the first tube 202 and the first fluid reservoir 220 can be in fluid communication via the third valve 270 and the first valve 250. In the first assembly configuration, the second valve 260 can be in either the first or second configuration of the second valve 260 because the second valve 260 is isolated from the flow path from the patient access subassembly 210, through the first tube 202, the third valve 270, the first valve 250, and into the first fluid reservoir 220.

In the second assembly configuration, the first valve 250 can be in the second configuration of the first valve 250 and the second valve 260 can be in the first configuration of the second valve 260 such that the first fluid first reservoir 220 and the second fluid reservoir 230 are in fluid communication via the first valve 250 and the second valve 260. The third valve 270 can be in either the first or second configuration of the third valve 270 because the third valve 270 is isolated from the flow path between the first fluid reservoir 220 and the second fluid reservoir 230 via the first valve 250 and the second valve 260.

In the third assembly configuration, the first valve 250 can be in the third configuration of the first valve 250 and the second valve 260 can be in the second configuration of the second valve 260 such that the first fluid reservoir 220 can be in fluid communication with the second tube 204A. The third valve 270 can be in either the first or second configuration of the third valve 270 because the third valve 270 is isolated from the flow path between the first fluid reservoir 220 and the second tube 204A via the first valve 250 and the second valve 260.

In some embodiments, the assembly 240 can have a fourth assembly configuration in which the third fluid reservoir 280 is in fluid communication with the second tube 204A. In the fourth assembly configuration, the first valve 250 can be in the third configuration of the first valve 250, the second valve 260 can be in the second configuration of the second valve 260, and the third valve 270 can be in the second configuration of the third valve 270 such that the third fluid reservoir 280 is in fluid communication with the second tube 204A (and the patient access subassembly 210) via the third valve 270, the first valve 250, and the second valve 260. In the fourth assembly configuration, the flow path from the third fluid reservoir 280 to the second tube 204A can be fluidically isolated from the first tube 202, the first fluid reservoir 220, and the second fluid reservoir 230.

The first fluid reservoir 220, the second fluid reservoir 230, and/or the third fluid reservoir 280 can be defined or included in any suitable fluid containing component. For example, in some embodiments, the system 200 can include a number of syringes such that the first fluid reservoir 220, the second fluid reservoir 230, and/or the third fluid reservoir 280 are each defined by a syringe having a barrel and a plunger such that fluid can be drawn into and expelled from each of the fluid reservoirs via, for example, translation of the respective plunger. In some embodiments, the system 200 can include a number of fluid bags such that the first fluid reservoir 220, the second fluid reservoir 230, and/or the third fluid reservoir 280 can each be defined by a fluid bag such that fluid can be drawn into and/or expelled from each of the fluid reservoirs via, for example, squeezing a respective fluid bag, a pump, and/or gravitational effects on the fluid. In some embodiments, the system 200 can include a combination of one or more syringes and one or more fluid bags such that one or more of the first fluid reservoir 220, the second fluid reservoir 230, and/or the third fluid reservoir 280 can be defined by a syringe and one or more of the others can be defined by a fluid bag.

In some embodiments, the first fluid reservoir 220 can include (e.g., be prefilled with) an anti-coagulant, such as, for example, ACD-A, ACD-B, EDTA, or heparin. In some embodiments, the first fluid reservoir 220 can be prefilled with both an anti-coagulant and an antioxidant (e.g., vitamin C or N-acetylcysteine). In some embodiments, the second fluid reservoir 230 can include (e.g., be prefilled with) a medicament, such as, for example, 2-Bromo-1-(3,3-dinitroazetidin-1-yl)ethanone, propofol, a nitric oxide donor, a chemotherapy drug, and/or ozone. In some embodiments, the third fluid reservoir 280 can include (e.g., be prefilled with) saline.

In some embodiments, as shown in FIG. 2, the system 200 can include a number of selective flow inhibitors coupled to tubing of the system 200 and configured to transition between an open and a closed configuration such that the flow through the tubing can be temporarily inhibited. For example, a first selective flow inhibitor 218 can be disposed on the access tube 216, a second selective flow inhibitor 206 can be disposed on the first tube 202, and a third selective flow inhibitor 208 can be disposed on the third tube 204B. Each of the first selective flow inhibitor 218, the second selective flow inhibitor 206, and the third selective flow inhibitor 208 can be, for example, tubing clamps or roller clamps.

In use, the first fluid reservoir 220 can be prefilled with a volume of anti-coagulant. The second fluid reservoir 230 can be prefilled with a volume of medicament. The third fluid reservoir 280 can be prefilled with a volume of saline. In some embodiments, the third fluid reservoir 280 can be separate from the assembly 240 during the initial stages of use of the system 200.

With each of the first selective flow inhibitor 218, the second selective flow inhibitor 206, and the third selective flow inhibitor 208 in the closed configuration, the first tube 202 can be coupled to the third valve 270 and the third tube 204B can be coupled to the connector 214. The patient access subassembly 210 can be placed in fluid communication with a patient's vasculature via the patient access port 212 (e.g., via inserting a needle of the patient access port 212 through a patient's skin or via coupling the patient access port 212 to an existing port through a patient's skin or a connector coupled to an intravascular tubing line). The assembly 240 can be arranged in the first assembly configuration such that the patient access subassembly 210 is in fluid communication with the first fluid reservoir 220 via the first tube 202, the third valve 270, and the first valve 250. For example, the first valve 250 can be manipulated or toggled into the first configuration of the first valve 250 and the third valve 270 can be manipulated or toggled into the first configuration of the third valve 270. The first selective flow inhibitor 218 and the second selective flow inhibitor 206 can then be transitioned to the opened configuration. Blood can then be drawn from the patient, through the patient access subassembly 210, the first tube 202, the third valve 270, the first valve 250, and into the first fluid reservoir 220 such that the blood combines with the anticoagulant within the first fluid reservoir 220 to form a first substance. For example, a plunger of a syringe defining the first fluid reservoir 220 can be translated relative to a barrel of the syringe to draw blood into the first fluid reservoir 220.

The first selective flow inhibitor 218 and the second selective flow inhibitor 206 can then be transitioned to the closed configuration. The assembly 220 can then be transitioned to the second assembly configuration such that the first fluid reservoir 220 is in fluid communication with the second fluid reservoir 230. For example, the first valve 250 and the second valve 260 can be manipulated or toggled such that the first valve 250 is in the second configuration of the first valve 250 and the second valve 260 is in the first configuration of the second valve 260. A portion of the first substance (e.g., a volume equal to or greater than twice the volume of the medicament in the second fluid reservoir 230) can then be transferred from the first fluid reservoir 220 to the second fluid reservoir 230 such that the portion of the first substance combines with the medicament within the second fluid reservoir 230 to form a second substance. For example, a plunger of a syringe defining the first fluid reservoir 220 can be translated to expel the portion of the first substance from the first fluid reservoir 220 and push the first substance into the second fluid reservoir 230. In some embodiments, a plunger or a syringe defining the second fluid reservoir 230 can be simultaneously translated relative to a barrel of the syringe to assist in drawing the first substance into the second fluid reservoir 230.

While the assembly 240 remains in the second assembly configuration, the second substance can be transferred from the second fluid reservoir 230 to the first fluid reservoir 220 such that the second substance combines with the remaining portion of the first substance in the first fluid reservoir 220 to form a third substance. For example, a plunger of a syringe defining the second fluid reservoir 230 can be translated to expel the second substance from the second fluid reservoir 230 and push the second substance into the first fluid reservoir 220. In some embodiments, a plunger or a syringe defining the first fluid reservoir 220 can be simultaneously translated relative to a barrel of the syringe to assist in drawing the second substance into the first fluid reservoir 220.

The assembly 240 can then be transitioned to the third assembly configuration such that the first fluid reservoir 220 is in fluid communication with the patient access subassembly 210 via the first valve 250, the second valve 260, the second tube 204, the filter 290, and the third tube 204B. For example, the first valve 250 can remain in the second configuration of the first valve 250 and the second valve 260 can be manipulated or toggled such that the second valve 260 is in the second configuration of the second valve 260. The third selective flow inhibitor 208 and the first selective flow inhibitor 218 can be transitioned to the open configuration. The third substance can then be transferred from the first fluid reservoir 220 to the patient's vasculature system via the first valve 250, the second valve 260, the second tube 204A, the filter 290, the third tube 204B, and the patient access subassembly 210.

After transferring the third substance to the patient's vasculature, the third fluid reservoir 280 can be coupled to the third valve 270. The assembly 240 can then be transitioned to the fourth assembly configuration such that the third fluid reservoir 280 is in fluid communication with the patient access subassembly 210 via the third valve 270, the first valve 250, the second valve 260, and the second tube 204. For example, the first valve 250 can be manipulated or toggled such that the first valve 250 is in the third configuration of the first valve 250, the second valve 260 can remain in the second configuration of the second valve 260, and the third valve 270 can be manipulated or toggled such that the third valve 270 is in the second configuration of the third valve 270. The contents of the third fluid reservoir 280 (i.e., saline) can then be transferred to the patient access subassembly 210 via the third valve 270, the first valve 250, the second valve 260, the second tube 204A, the filter 290, and the third tube 204B such that the saline flushes out the fluid flow path of the third substance. The third selective flow inhibitor 208 and the first selective flow inhibitor 218 can then be transitioned to the closed configuration, and the third tube 204B can be detached from the connector 214. The first tube 202 can be detached from the third valve 270. The patient access subassembly 210 can then be detached from the patient.

In some embodiments, the system 200 can optionally include an actuation subsystem (not shown). The actuation subsystem can include one or more actuators configured to engage with one or more of the components of the system 200. For example, rather than manually adjusting a configuration or orientation of a valve of the assembly 240, an actuator can engage and adjust the configuration of orientation of the valve of the assembly 240. In some embodiments, the actuation subsystem can include a first actuator operably coupled to the first valve 250, a second actuator operably coupled to the second valve 260, and a third actuator operably coupled to the third valve 270. Each of the first actuator, the second actuator, and the third actuator can be configured to transition (e.g., manipulate or toggle) the first valve 250, the second valve 260, and the third valve 270, respectively, between their respective operating configurations. The actuation subsystem can also include a first reservoir actuator configured to control the flow of fluid into and out of the first fluid reservoir 220, a second reservoir actuator configured to control the flow of fluid into and out of the second fluid reservoir 230, and a third reservoir actuator configured to control the flow of fluid into and out of the third fluid reservoir 280. The first reservoir actuator can be configured to operably engage and control the position of a plunger associated with the first fluid reservoir 220 to control the flow of fluid into and out of the first fluid reservoir 220, the second reservoir actuator can be configured to operably engage and control the position of a plunger associated with the second fluid reservoir 230 to control the flow of fluid into and out of the second fluid reservoir 230, and the third reservoir actuator can be can be configured to operably engage and control the position of a plunger associated with the third fluid reservoir 280 to control the flow of fluid into and out of the third fluid reservoir 280.

In some embodiments, rather than including an actuation subsystem, the system 200 can optionally be coupleable to a separate actuation system (not shown). For example, the actuation system can include a housing and a number of actuators, each configured to operably engage and/or control a configuration of a valve or a flow of fluid relative to a reservoir of the system 200. The actuation system can be configured to receive the system 200 such that the actuation system can operably engage the system 200 and control operation of the system 200 to perform any of the methods steps described herein. In some embodiments, the system 200 can be disposable and the actuation system can be reusable.

Figure 3:
FIG. 3 is a flow chart of a method, according to an embodiment.

FIG. 3 is a flow chart representing a method 300. In some embodiments, the method 300 can be used in conjunction with any of the systems described herein for drawing cells (e.g., packed red blood cells, white blood cells, and/or platelets) from a patient, combining medicament with the cells of the patient ex vivo, and infusing the combined cells and medicament into the patient's bloodstream. Unless explicitly noted otherwise, similarly named components can be structurally and/or functionally similar to those in FIG. 1 and/or FIG. 2. As shown in FIG. 3, the method 300 includes coupling, at step 302, a patient access subassembly to a patient, the patient access subassembly fluidically coupled to a first fluid reservoir containing a first substance (e.g., an anticoagulant and/or an antioxidant) and a second fluid reservoir containing a second substance (e.g., a medicament such as 2-Bromo-1-(3,3-dinitroazetidin-1-yl)ethanone, propofol nitric oxide, and/or ozone) via an assembly. Cells (e.g., packed red blood cells, white blood cells, and/or platelets) can be drawn, at step 304, through the patient access subassembly, through the assembly, and into the first fluid reservoir such that the cells and the first substance form a third substance. The assembly can be manipulated, at step 306, such that the first fluid reservoir is fluidically isolated from the patient access subassembly and such that the first fluid reservoir is in fluidic communication with the second fluid reservoir. A portion of the third substance can be transferred, at step 308, from the first fluid reservoir through the assembly and into the second fluid reservoir such that the portion of the third substance and the second substance form a fourth substance. The fourth substance can be transferred, at step 310, from the second fluid reservoir through the assembly and into the first fluid reservoir such that the remainder of the third substance and the fourth substance form a fifth substance. The assembly can be manipulated, at step 312, such that the first fluid reservoir is in fluid communication with the patient access subassembly. The fifth substance can be transferred, at step 314, from the first fluid reservoir through the assembly, through the patient access subassembly, and into the patient. A third fluid reservoir containing a saline solution can be fluidically coupled, at step 316, to the assembly. The assembly can be manipulated, at step 318, such that the third fluid reservoir is in fluid communication with the patient access subassembly via the assembly. At least a portion of the saline solution can be transferred, at step 320, from the assembly to the patient access subassembly.

FIG. 4 is a flow chart representing a method 400. In some embodiments, the method 400 can be used in conjunction with any of the systems described herein for assembling a system for drawing cells (e.g., packed red blood cells, white blood cells, and/or platelets) from a patient, combining medicament with the cells of the patient ex vivo, and infusing the combined cells and medicament into the patient's bloodstream. Unless explicitly noted otherwise, similarly named components can be structurally and/or functionally similar to those in FIG. 1 and/or FIG. 2. As shown in FIG. 4, the method 400 includes fluidically coupling, at step 402, a first coupling member of a first subassembly to a valve assembly of a second subassembly. The second subassembly can include a first fluid reservoir and a second fluid reservoir fluidically coupled to the valve subassembly. The first fluid reservoir can be selectively fluidically coupled to the second fluid reservoir via the valve assembly. The first subassembly can include a patient access port, a first coupling member, and a second coupling member. The first coupling member and the second coupling member can be in fluid communication with the patient access port. The first coupling member can be coupled to the valve assembly such that the first fluid reservoir of the second subassembly is in selective fluid communication with the patient access port via a first flow path. The second coupling member of the first subassembly can be fluidically coupled, at step 404, to the valve assembly such that the first fluid reservoir is in selective fluid communication with the patient access port via a second flow path different from the first flow path. A third fluid reservoir can be coupled, at step 406, to the valve assembly such that the third fluid reservoir is in selective fluid communication with the patient access port via the second flow path.

Figure 5:
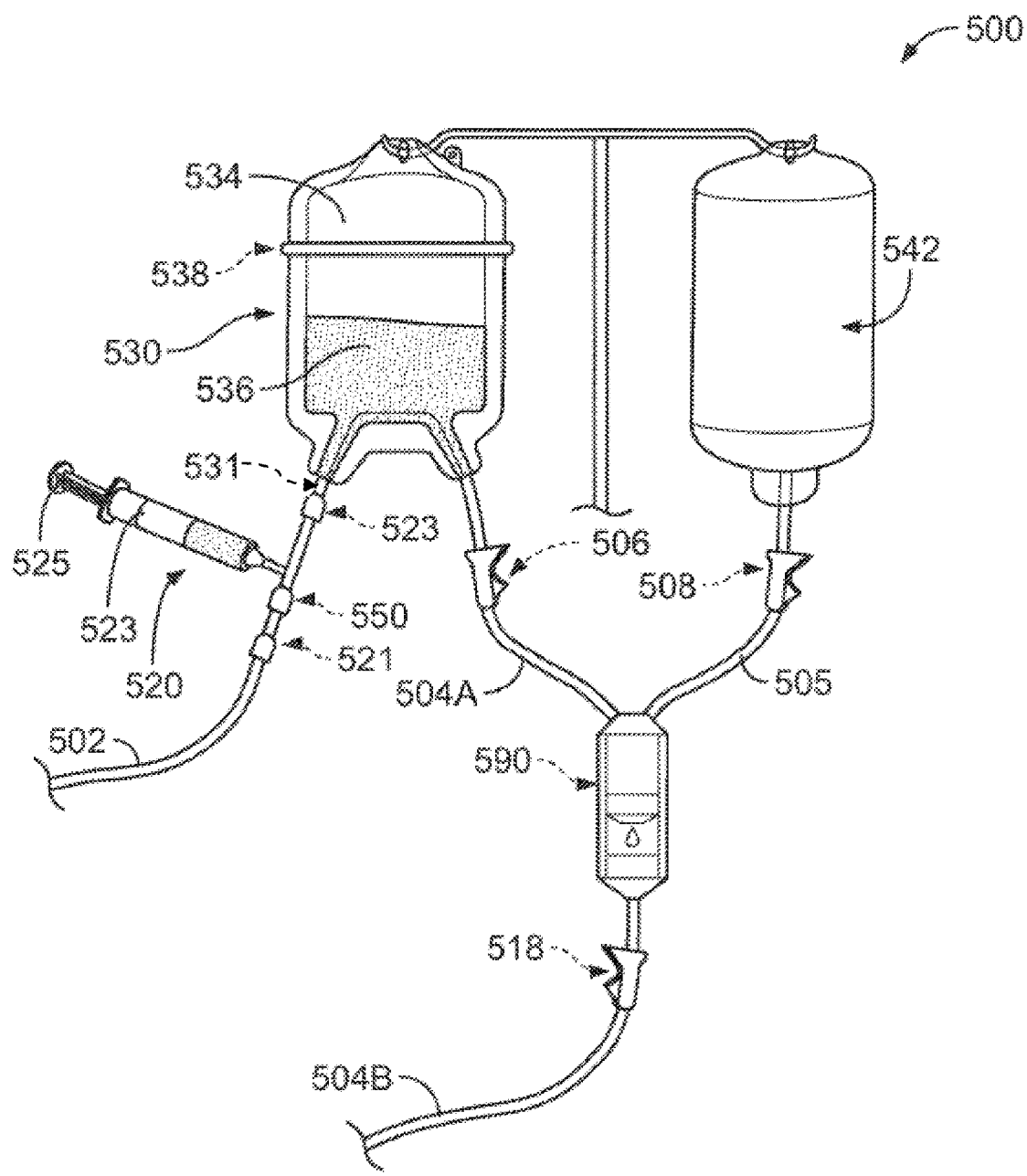
FIG. 5 is an illustration of a system, according to another embodiment.

FIG. 5 is an illustration of a system 500 useful for drawing cells (e.g., packed red blood cells, white blood cells, and/or platelets) from a patient, combining medicament with the cells of the patient ex vivo, and infusing the combined cells and medicament into the patient's bloodstream. The system 500 is a non-limiting example, and can be the same or similar in structure and/or function any of the systems described herein, such as the system 100 and/or the system 200. Unless explicitly noted otherwise, similarly named and referenced components can be structurally and/or functionally similar to those described above, such as with reference to FIG. 1 and/or FIG. 2. The system 500 includes a syringe 520, a valve 550, a first fluid bag 530, a second fluid bag 542, and a filter 590. The syringe 520 includes a barrel 523 and a plunger 525 which collectively define a fluid reservoir. The syringe 520 can be pre-filled with an anticoagulant, such as, for example, ACD-A, ACD-B, EDTA, or heparin. The system 500 can also include a first tube 502 fluidically coupled to a blood vessel of a patient such that cells can be drawn from the patient through the first tube 502. The first tube 502 can include a first connector 521, which can be, for example, a needleless connector (also referred to as a needle free connector), such that the first tube 502 can be coupled to the valve 550 via the needleless connector 521. The system 500 can also include a second connector 523, which can be, for example, a double male luer lock, and a needle 531. The valve 550 can be coupled to the first fluid bag 530 via the second connector 523 and the needle 531.

The syringe 520 can be coupled to the valve 550 such that the valve 550 can control the flow of fluid into and out of the syringe 520. The valve 550 can have a first configuration in which the reservoir of the syringe 520 is in fluid communication with the first tube 502 such that translation of the plunger 525 relative to the barrel 523 draws cells from the patient into the reservoir of the syringe 520, but the reservoir of the syringe 520 is fluidically isolated from the second connector 523. The valve 550 can have a second configuration in which the reservoir of the syringe 520 is in fluid communication with the first fluid bag 530 via the second connector 523 and the needle 531, but the reservoir of the syringe 520 is fluidically isolated from the first tube 502. The valve 550 can include any suitable valve mechanism, such as, for example, a manual valve mechanism, a solenoid-actuated valve mechanism, a motor-operated valve mechanism, a hydraulic valve mechanism, and/or a pneumatic valve mechanism. In some embodiments, the valve 550 can be a stopcock such that a portion of the valve 550 can be rotated between the first configuration and the second configuration.

The first fluid bag 530 includes a first reservoir 536, a second reservoir 534, and a dividing strip 538. The second reservoir 534 can be prefilled with medicament, such as, for example, 2-Bromo-1-(3,3-dinitroazetidin-1-yl)ethanone, propofol, a nitric oxide donor, a chemotherapy drug, and/or ozone. The dividing strip 538 can be removable such that the medicament in the second reservoir 534 can travel into the first reservoir 536 (e.g., due to gravitational effects).

The second fluid bag 542 can be pre-filled with saline (e.g., 0.9% Sodium Chloride). The first fluid bag 530 can be fluidically coupled to the filter 590 via a second tube 504A and the second fluid bag 542 can be fluidically coupled to the filter 590 via a saline tube 505. A first selective flow inhibitor 506 can be disposed on the second tube 504A such that the first selective flow inhibitor 506 can selectively apply pressure to the second tube 504A to prevent fluid flow through the second tube 504A. A second selective flow inhibitor 508 can be disposed on the saline tube 505 such that the first selective flow inhibitor 508 can selectively apply pressure to the saline tube 505 to prevent fluid flow through the saline tube 505.

The filter 590 can be the same or similar in structure and/or function to the filter 290 described above with respect to FIG. 2. For example, the filter 590 can have any suitable pore size depending on the substance intended to be filtered from fluid passing through the filter 590. The filter 590 can be coupled to a third tube 504B such that fluid exiting the filter 590 can be infused into the patient via the third tube 504B. A third selective flow inhibitor 518 can be disposed on the third tube 504B such that the first selective flow inhibitor 506 can selectively apply pressure to the third tube 504B to prevent fluid flow through the third tube 504B. The first selective flow inhibitor 506, the second selective flow inhibitor 508, and the third selective flow inhibitor 518 can each be, for example, roller clamps or any other suitable type of tubing clamp.

In use, the valve 550 can be arranged in the first configuration and the first selective flow inhibitor 506, the second selective flow inhibitor 508, and the third selective flow inhibitor 518 can each be closed such that fluid flow is obstructed through the second tube 504A, the third tube 504B, and the saline tube 505. The plunger 525 can then be translated (e.g., pulled) such that cells are drawn from the patient, through the first tube 502, and into the barrel 523 of the syringe 523. In some embodiments, the cells can be combined with a coagulant in the syringe 523 to form a first substance. The valve 550 can then be transitioned to the second configuration. The plunger 525 can then be translated (e.g., pushed) such that the first substance is expelled from the syringe 520 and pushed through the second connector 523 and the needle 531 into the first reservoir 536 the first fluid bag 530. The dividing strip 538 can then be removed such that the medicament in the second reservoir 534 can be released and combine with the first substance in the reservoir 536 to form a second substance. The first selective flow inhibitor 506 and the third selective flow inhibitor 518 can then be transitioned to an open position such that the second substance can flow through the second tube 504A, the filter 590, the third tube 504B, and into the patient's blood vessel. Then, the second selective flow inhibitor 508 can be transitioned to an open position such that the contents of the second fluid bag 542 (e.g., saline) can flow through the saline tube 505, the filter 590, the third tube 504B, and into the patient's blood vessel.

Figure 6:
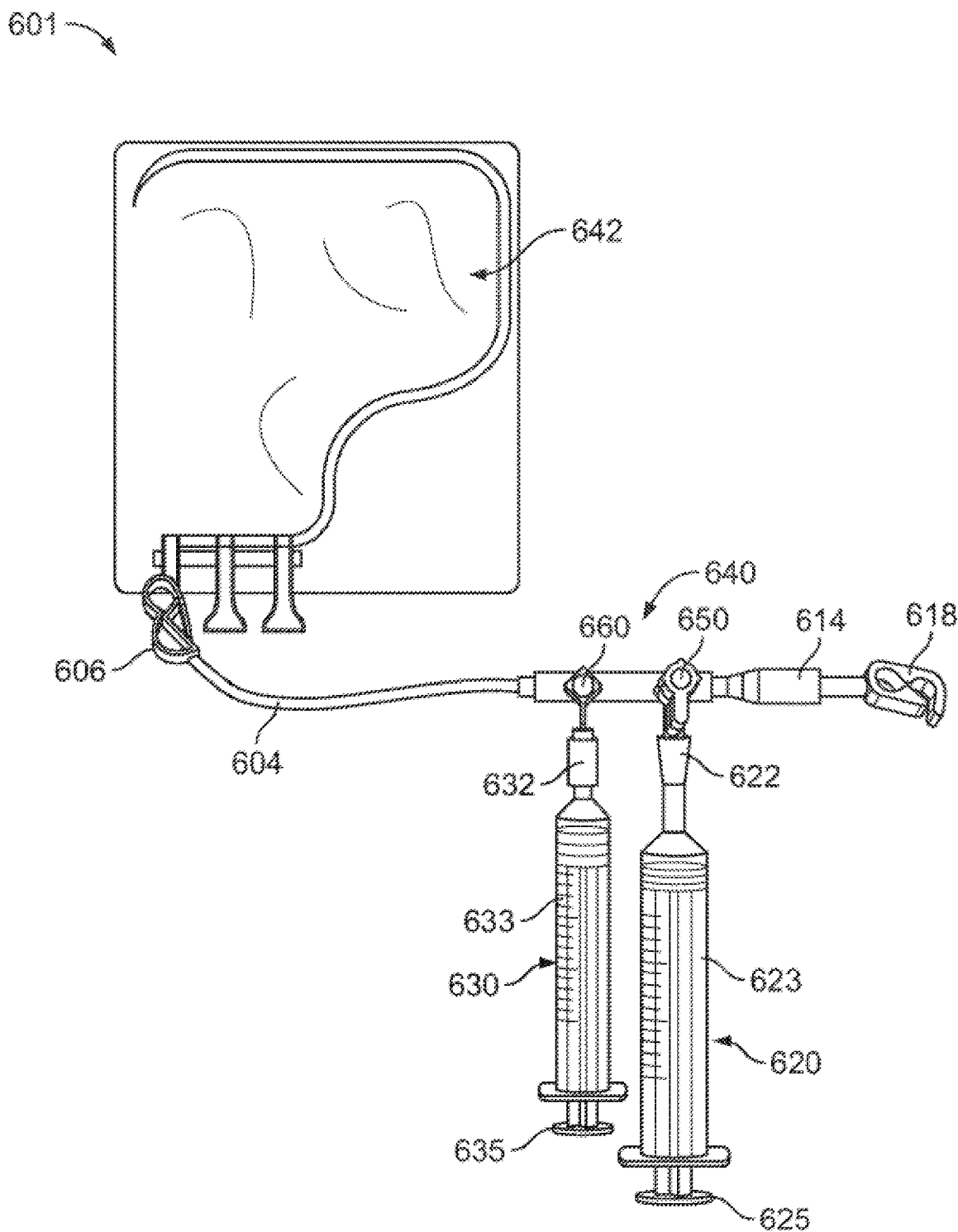
FIG. 6 is a top view of a mixing assembly of an example system, according to an embodiment.

FIG. 6 is a top view of a mixing assembly 601 of a system 600 prior to assembly of the system 600. The system 600 can be the same or similar in structure and/or function to any of the systems described herein. Unless explicitly noted otherwise, similarly named and referenced components can be structurally and/or functionally similar to those described above with reference to, for example, FIGS. 1, 2, and/or 5. In some embodiments, the system 600 is useful for drawing cells (e.g., packed red blood cells, white blood cells, and/or platelets) from a patient, combining medicament with the cells of the patient ex vivo, and infusing the combined cells and medicament into the patient's bloodstream. The mixing assembly 601 includes a first syringe 620 defining a first fluid reservoir, a second syringe 630 defining a second fluid reservoir, a first fluid bag 642, and an assembly 640. The first syringe 620 includes a barrel 623 and a plunger 625. The second syringe 630 includes a barrel 633 and a plunger 635. The assembly 640 includes a first valve 650 and a second valve 660. In some embodiments, the assembly 640 can include a 2-gang valve manifold. Each valve of the first valve 650 and the second valve 660 can include a valve lever to control the flow of fluid through the valve. The direction of extension of the valve lever can indicate the direction of the fluid line that is isolated or "off". In some embodiments, the first valve 650 can be coupled to the second fluid valve 660 by the user (e.g., a clinician, doctor, or nurse) during assembly of the mixing assembly 601. The first valve 650 can include a needleless connection port for connection to a needleless connector, such as the third connector 614 discussed below. The first syringe 620 can be coupled to the first valve 650 via a first connector 622 and the second syringe 630 can be coupled to the second valve 660 via a second connector 632. The first valve 650 can be coupled to the second valve 660. The first fluid bag 642 can be coupled to the second valve 660 via a first tube 604. A first selective flow inhibitor 606 can be disposed on the first tube 604 such that the first selective flow inhibitor 606 can selectively prevent the flow of fluid through the first tube 604. For example, the first selective flow inhibitor 606 can have an open configuration and a closed configuration, the first selective flow inhibitor 606 configured to squeeze the first tube 604 closed in the closed configuration. For example, the first selective flow inhibitor 606 can be a roller clamp or a tubing clamp. The first connector 632 and/or the second connector 622 can be needleless connectors (also referred to as needle free connectors). For example, the first connector 632 and/or the second connector 622 can be an ICU Medical MC100 MicroClave Neutral Connector. The first syringe 620 can be pre-filled with an anti-coagulant such as, for example, ACD-A, ACD-B, EDTA, or heparin. The second syringe 630 can be pre-filled with a medicament, such as, for example, 2-Bromo-1-(3,3-dinitroazetidin-1-yl)ethanone, propofol, a nitric oxide donor, a chemotherapy drug (e.g., a tyrosine kinase inhibitor), and/or ozone. In some embodiments, the first syringe 620 can having a volume of 20 mL. In some embodiments, the second syringe 630 can have a volume of 10 mL. In some embodiments, the second syringe 630 can be pre-filled with between 1 mL and 5 mL of medicament.

In an example use scenario, the second fluid reservoir 630 can include medicament, such as 2-Bromo-1-(3,3-dinitroazetidin-1-yl)ethanone, propofol, a nitric oxide donor, a chemotherapy drug (e.g., a tyrosine kinase inhibitor), and/or ozone. The system 600 can be attached to a patient via the patient access subassembly 610 (described below). A volume of blood of the patient can be drawn through the patient access subassembly 610, through the assembly 640, and into the first fluid reservoir 620. A portion of the volume of blood drawn can be transferred to the second fluid reservoir 630 via the assembly 640 such that the portion combines with the medicament in the second fluid reservoir 630 to form a first combined substance. The first combined substance can then be returned to the first fluid reservoir 620 via the assembly 640 to combine with the remaining blood in the first fluid reservoir 620 to form a second combined substance. The second combined substance can then be pushed through the assembly 640, through the first tube 604, and into the first fluid bag 642. The second combined substance can then be delivered to the patient's bloodstream from the first fluid bag 642, via the patient access subassembly 610 as described below with reference to FIG. 19.

Each of the first valve 650 and the second valve 660 can be configured to transition between two or more configurations, each configuration corresponding to a different available flow path through the assembly 640. Each of the first valve 650 and the second valve 660 can include any suitable valve mechanism, such as, for example, a manual valve mechanism, a solenoid-actuated valve mechanism, a motor-operated valve mechanism, a hydraulic valve mechanism, and/or a pneumatic valve mechanism. For example, each of the first valve 650 and the second valve 660 can include a three-way stopcock. Each of the first valve 650 and the second valve 660 can define or include an interior region such that fluid can travel through the interior region. The first syringe 620 can be coupled to the first valve 650 such that the first syringe 620 can be in selective fluid communication with a patient access subassembly 610 (described below) via the first valve 650, the second syringe 630 via the first valve 650 and the second valve 660, or the first tube 604 via the first valve 650 and the second valve 660. For example, the first valve 650 can include a junction of three fluid lines, and can fluidically isolate one of the three fluid lines while allowing fluid flow between the other two lines. The first valve 650 can include a lever 651 that can be rotated to transition the first valve 650 between various valve configurations. The lever 651 can be configured to extend in the direction of the fluid line that is isolated. Therefore, for example, the first valve 650 can have a first configuration in which the first valve 650 allows fluid communication between the patient access subassembly 610 and the first syringe 620, but fluidically isolates an interior region of the second valve 660 from both the first syringe 620 and the patient access subassembly 610. The first valve 650 can have a second configuration in which the first valve 650 allows fluid communication between the first syringe 620 and an interior region of the second valve 660, but fluidically isolates the patient access subassembly 610 from both the first syringe 620 and the interior region of the second valve 660. The first valve 650 can have a third configuration in which the first valve 650 allows fluid communication between the patient access subassembly 610 and the interior region of the second valve 660, but fluidically isolates the first syringe 620 from both the patient access subassembly 610 and the interior region of the second valve 660.

In some embodiments, the second syringe 630 can be coupled to the second valve 660 such that the second syringe 630 can be in selective fluid communication with the first syringe 620 via the second valve 660 and the first valve 650 and with the first tubing 604 via the second valve 760. For example, the second valve 660 can include a junction of three fluid lines, and can fluidically isolate one of the three fluid lines while allowing fluid flow between the other two lines. The second valve 660 can include a lever 661 that can be rotated to transition the second valve 660 between various valve configurations. The lever 661 can be configured to extend in the direction of the fluid line that is isolated. Therefore, for example, the second valve 660 can have a first configuration in which the second valve 660 allows fluid communication between an interior region of the first valve 650 and the second syringe 630, but fluidically isolates the first tube 604 from both the second syringe 630 and the interior region of the first valve 650. The second valve 660 can have a second configuration in which the second valve 660 allows fluid communication between the interior region of the first valve 650 and the first tube 604, but fluidically isolates the second syringe 630 from both the interior region of the first valve 650 and the first tube 604.

Figure 7:
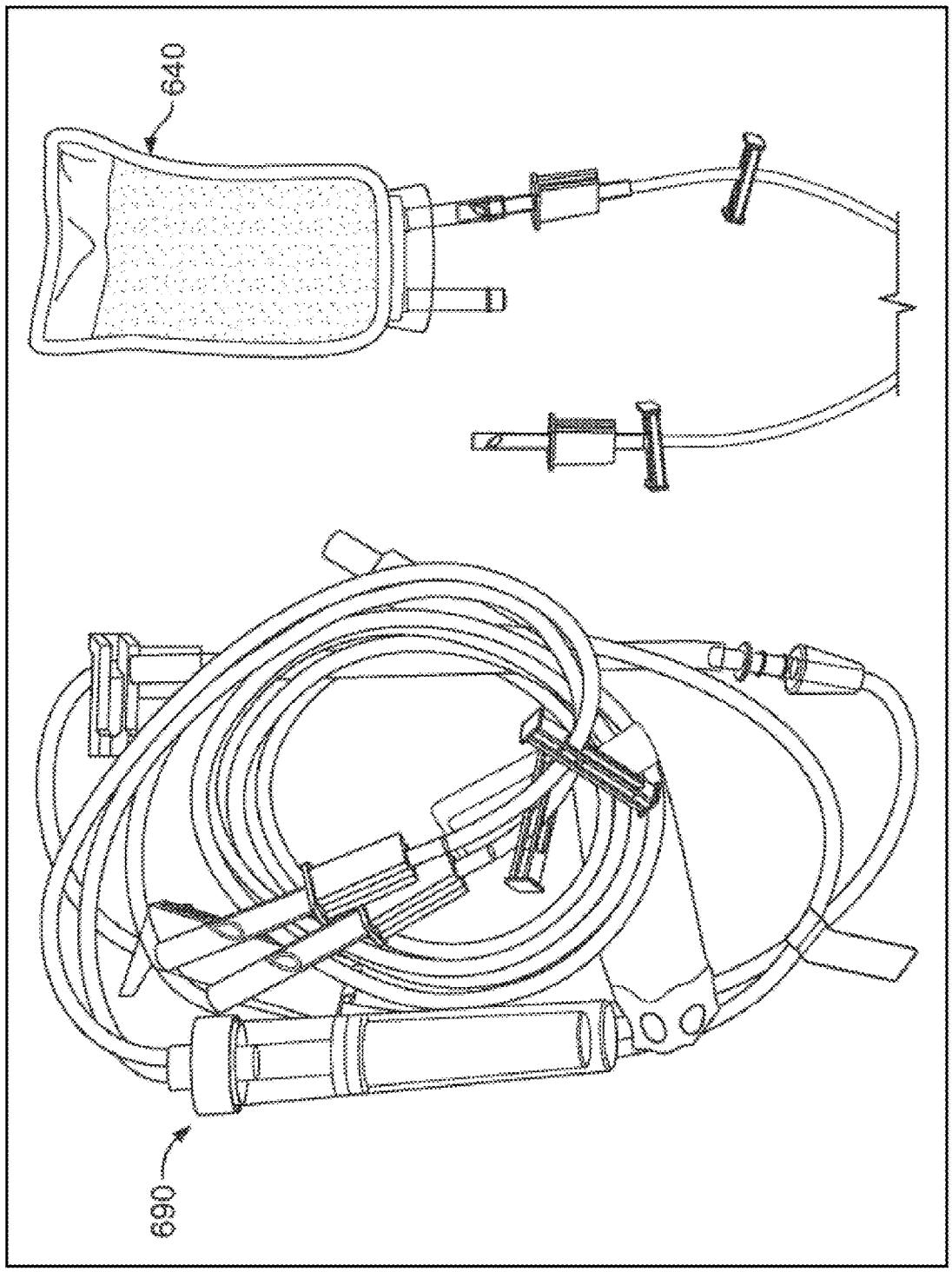
FIG. 7 is a top view of a filter subassembly of the system of FIG. 6, according to an embodiment.
Figure 19:
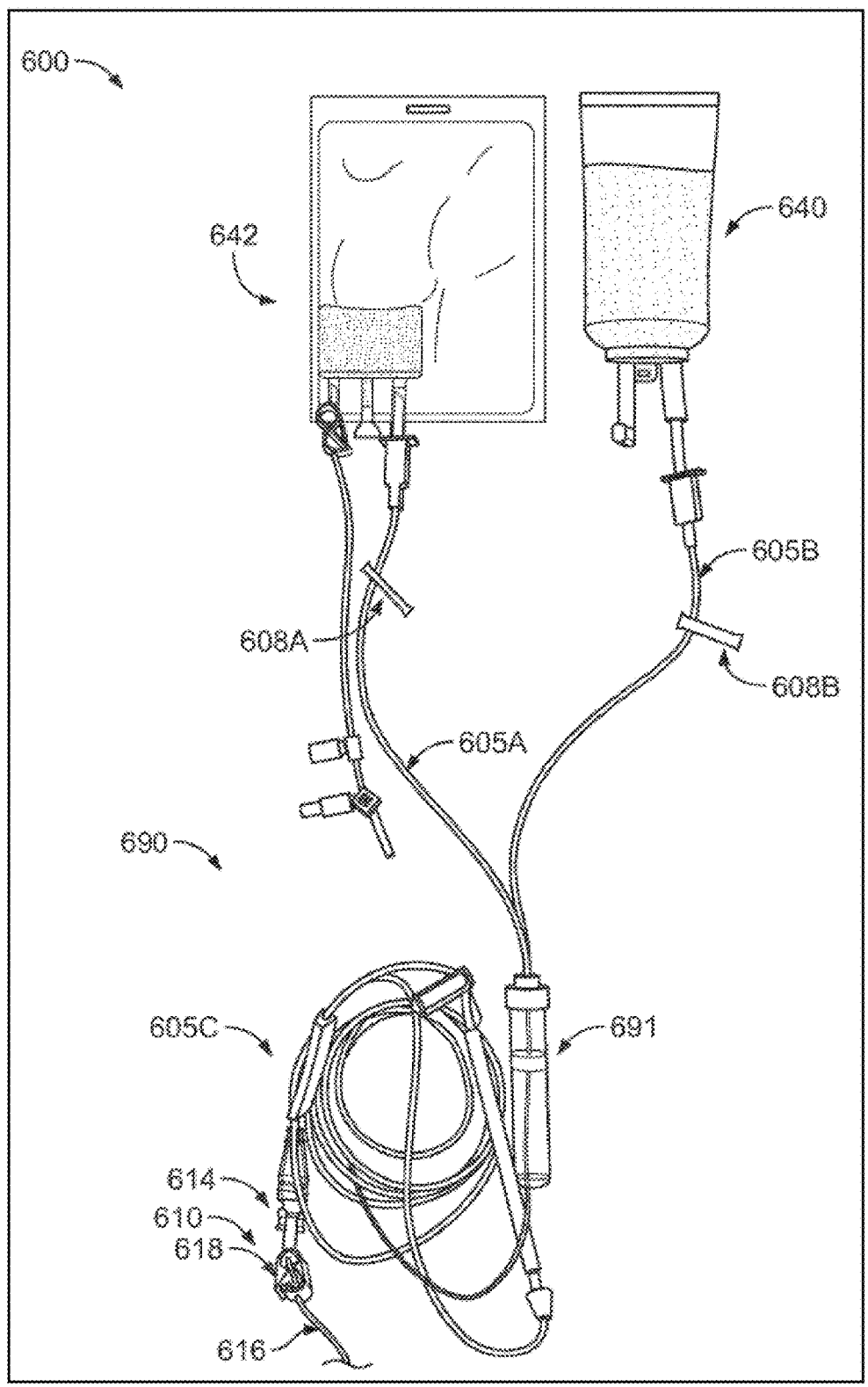
FIG. 19 is a top view of the system of FIG. 6 prior to infusion.

As shown in FIG. 7, the system 600 can also include a filter subassembly 690 including a second tube 605A, a third tube 605B, a fourth tube 605C, and a filter 691, which are shown and described in more detail with respect to FIG. 19. In some embodiments, filter 691 can be a drip chamber. The system 600 can also include a second fluid bag 640. The second fluid bag 640 can include, for example, saline (e.g., 0.9% Sodium Chloride). In some embodiments, the second fluid bag 640 can be, for example, a 100 mL bag.

Figure 8:
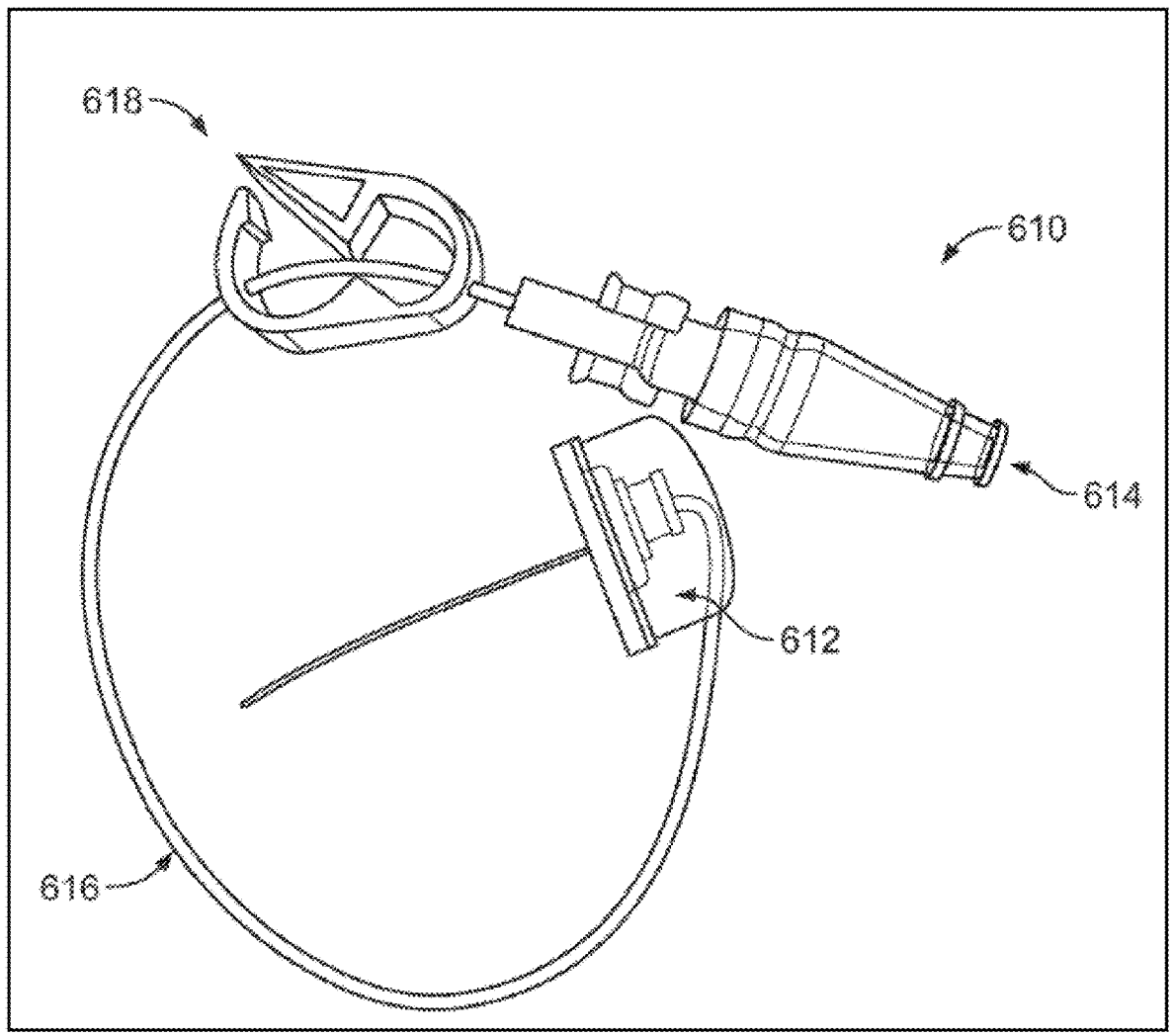
FIG. 8 is top view of a patient access subassembly of the system of FIG. 6, according to an embodiment.

As shown in FIG. 8, the system 600 can also include a patient access subassembly 610. The patient access subassembly 610 can include a patient access port 612, access tubing 616, and a third connector 614. The patient access port 612 can include any suitable element configured to provide access to a patient's vasculature system. For example, the patient access subassembly 610 can include a needle, such as, for example, a Huber needle. In some embodiments, the patient access subassembly 610 can include a connector configured to couple to a port previously coupled to the patient's vasculature system. The third connector 614 of the patient access subassembly 610 can be coupled to the first valve 650 (as shown in FIG. 6) such that the patient access subassembly 610 can be in fluid communication with the first valve 650. In some embodiments, the patient access subassembly 610 can be 19 G×1.5" or larger needle.

Figure 9:
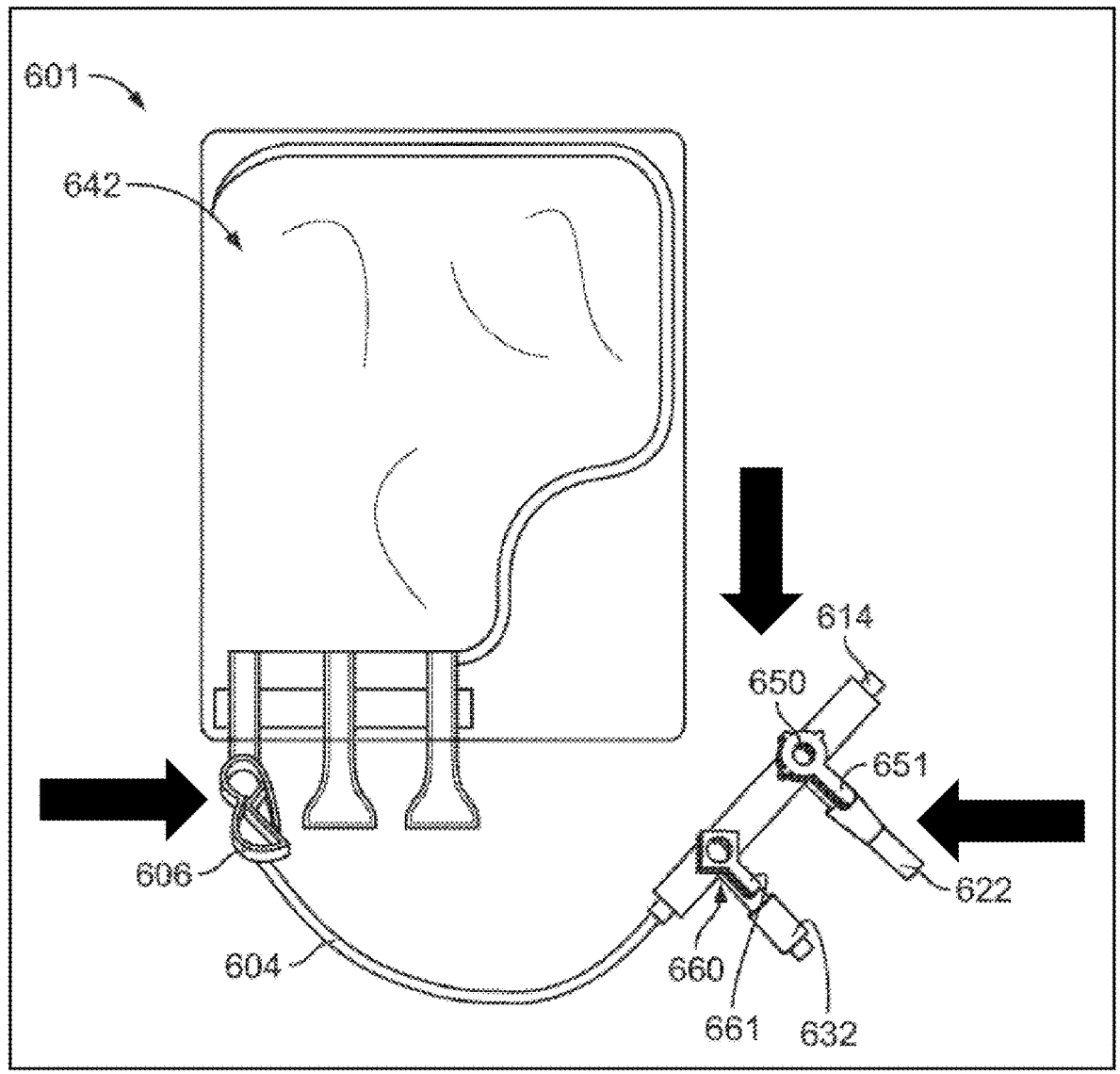
FIG. 9 is a top view of the mixing assembly of FIG. 6 in a partially assembled configuration, according to an embodiment.

FIG. 9 shows a top view of the mixing assembly 601 in a partially assembled configuration prior to attachment to the patient access subassembly 610. As shown, both the first valve 650 and the second valve 660 can be arranged such that the first connector 622 and the second connector 632 are fluidically isolated. The lever 651 of the first valve 650 and the lever 651 of the second valve 660 are both directed toward the first connector 622 and the second connector 632, respectively, signifying that fluid flow is isolated along those flow lines. Furthermore, the first selective flow inhibitor 606 can be slid near or adjacent to the first fluid bag 642 and transitioned to the closed position such that flow is inhibited within the first tube 604 at the location of the first selective flow inhibitor 606.

Figure 10:
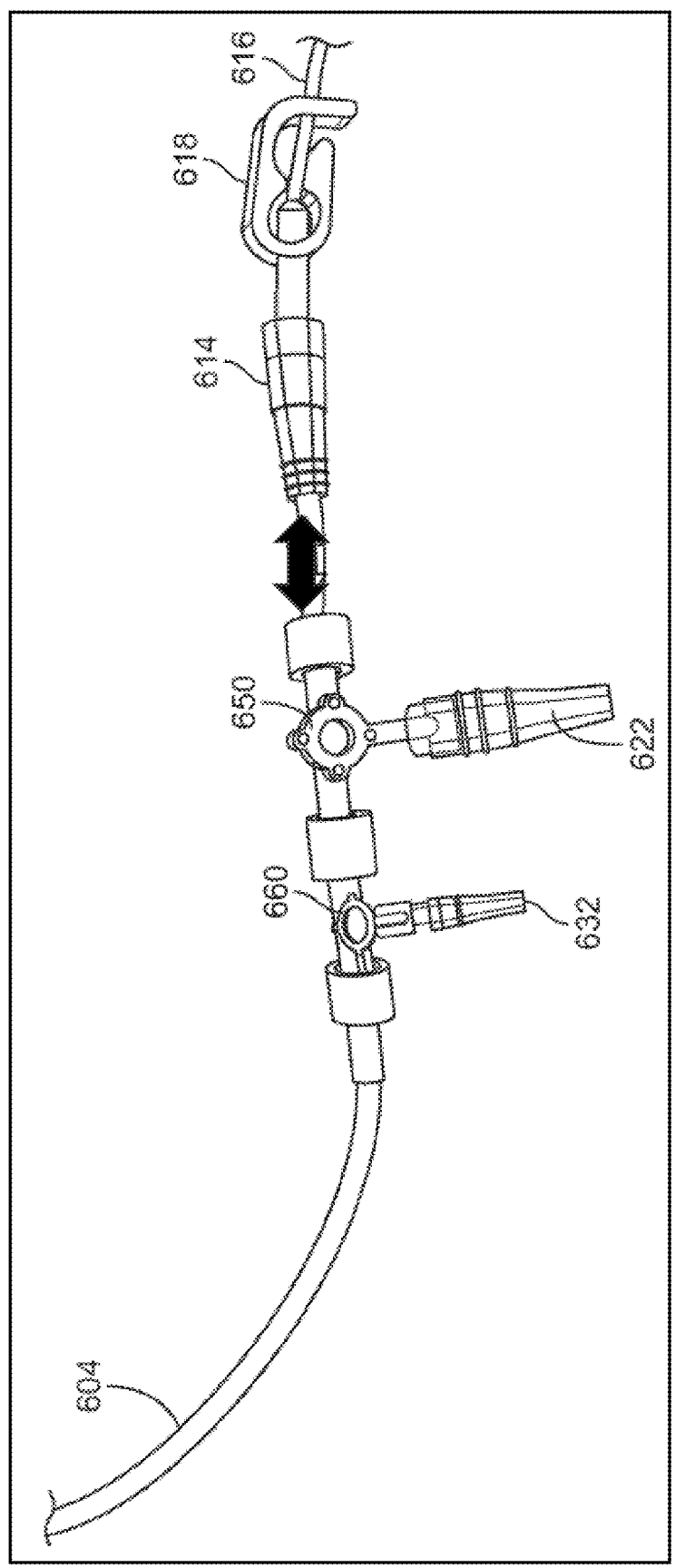
FIG. 10 is a top view of a portion of the mixing assembly of FIG. 6 and a portion of the patient access subassembly of FIG. 8 shown prior to assembly.

As shown in FIG. 10, with the third selective flow inhibitor 618 in the closed configuration to prevent the flow of fluid through the access tubing 616, the needleless connection port of the first valve 650 can be coupled to the third connector 614. In some embodiments, the third connector 614 can be swapped with alcohol prior to the coupling of the third connector 614 to the first valve 650.

Figure 11:
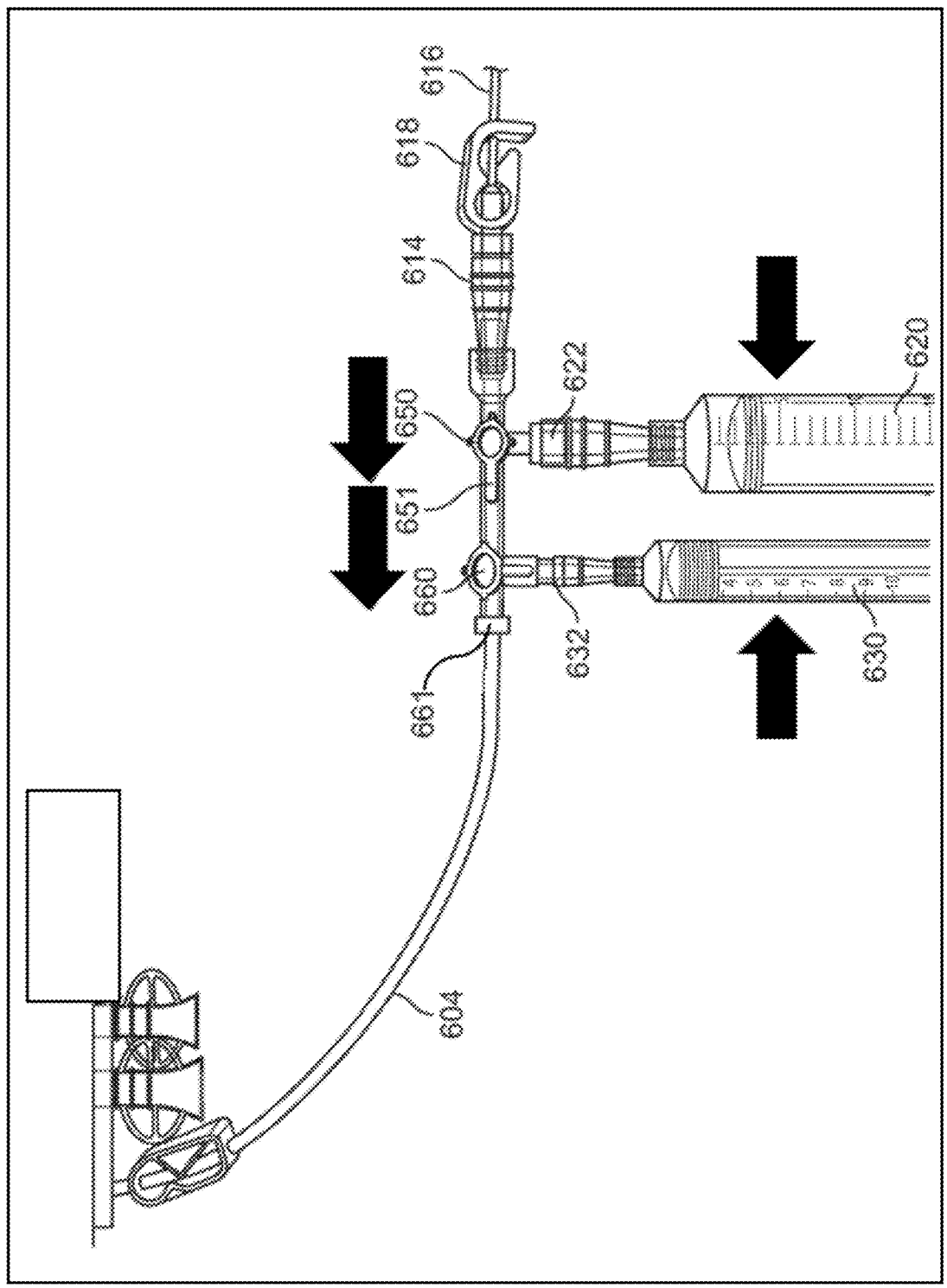
FIG. 11 is a top view of a portion of the mixing assembly of FIG. 6 and a portion of the patient access subassembly of FIG. 8 shown in an assembled configuration.

As shown in FIG. 11, the first syringe 620 can be coupled to the first connector 622 and the second syringe 630 can be coupled to the second connector 632. In some embodiments, an isopropyl alcohol pad can be used to swab the first connector 622 and the second connector 632 prior to coupling the first connector 622 and the second connector 632 to the first syringe 620 and the second syringe 630, respectively. The lever 651 of the first valve 650 and the lever 661 of the second valve 660 can then be rotated such that the first lever 651 is directed toward the second valve 660 and the second lever 661 is direct toward the first tube 604. Thus, the first valve 650 can fluidically isolate the first syringe 620 and the patient access subassembly 610 from the second valve 660, and the second valve 660 can fluidically isolate the second syringe 630 and the first valve 650 from the first tube 604.

Figure 12:
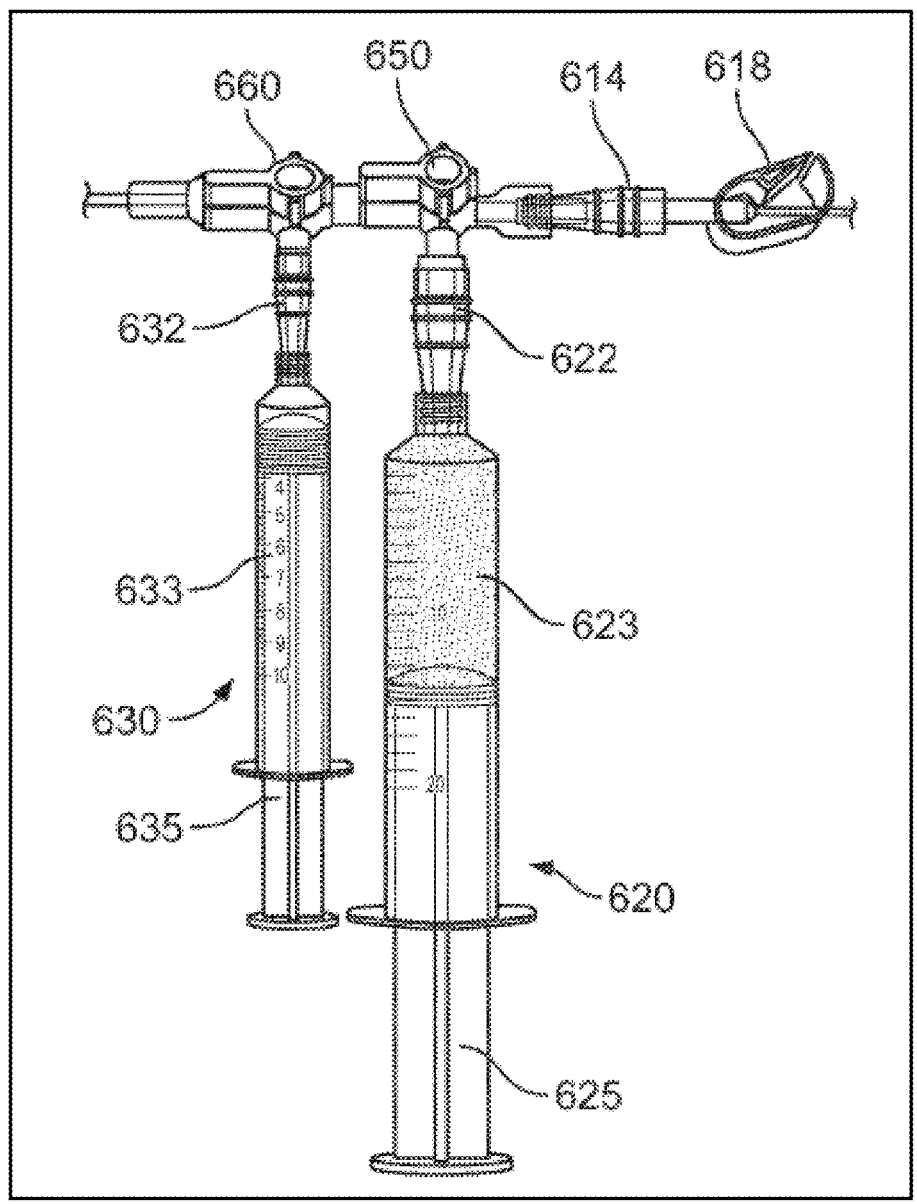
FIG. 12 is a top view of a portion of the mixing assembly of FIG. 6 and a portion of the patient access subassembly of FIG. 8 shown in a blood drawing configuration.

As shown in FIG. 12, with the patient access port 612 coupled to a patient's blood vessel, the third selective flow inhibitor 618 can be opened to allow blood flow through the access tubing 616. Blood can then be drawn from the patient, through the patient access subassembly 610, through the first valve 650, and into the syringe barrel 623. For example, the plunger 625 can be pulled as shown in FIG. 12 to draw the blood into the syringe barrel 623. The blood can combine with the anticoagulant in the syringe barrel 623 to form a first substance.

Figure 13:
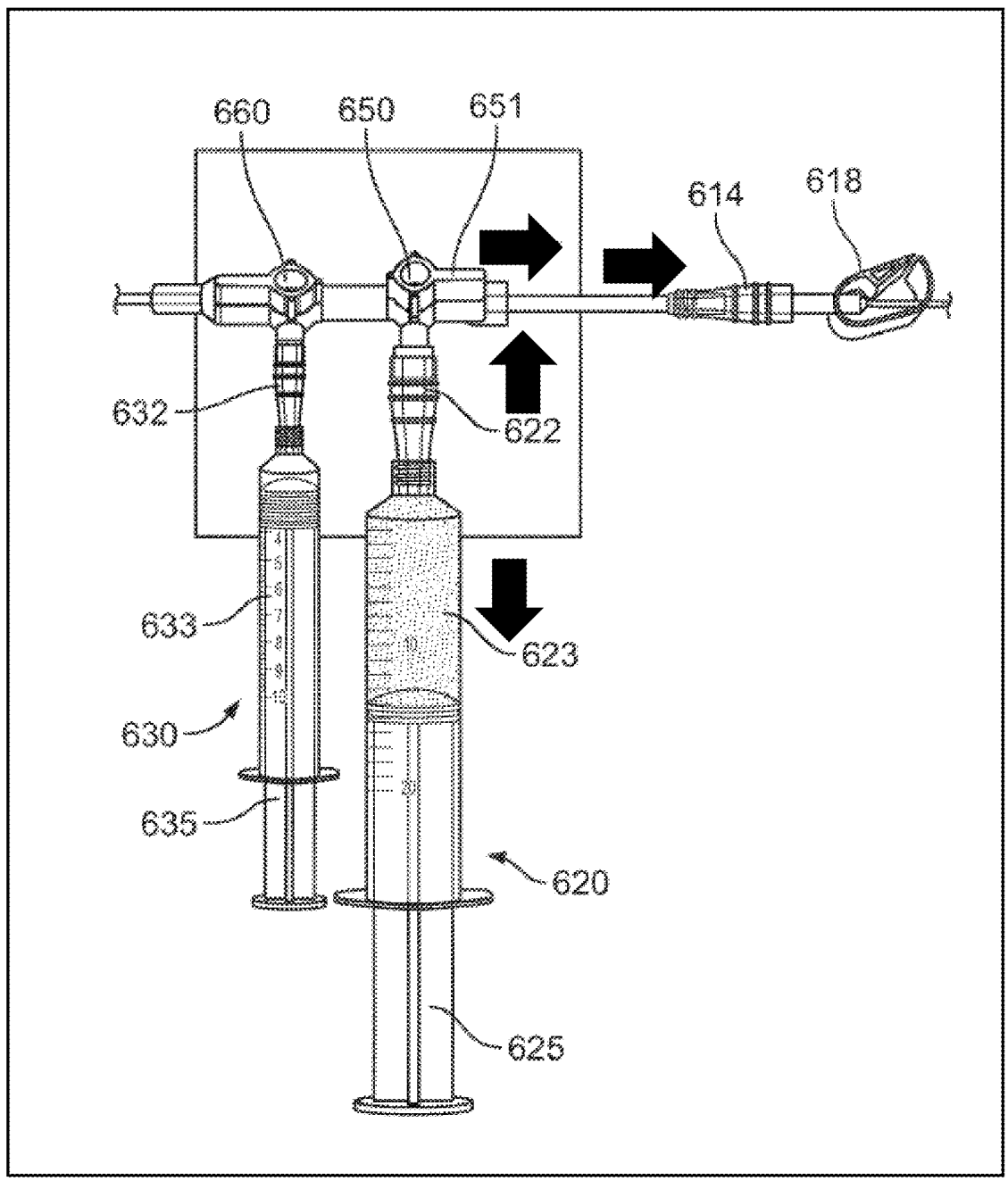
FIG. 13 is a top view of a portion of the mixing assembly of FIG. 6 and a portion of the patient access subassembly of FIG. 8 shown in a decoupled configuration.

As shown in FIG. 13, the patient access subassembly 610 can then be separated from the first valve 650. First, the lever 651 of the first valve 650 can be rotated to be directed toward the third connector 614 such that the third connector 614 and the access tubing 616 are fluidically isolated from the first syringe 620 and the second valve 660. The third selective flow inhibitor 618 can be closed to prevent fluid flow through the access tubing 616. Then, the third connector 614 can be decoupled from the first valve 650.

Figure 14:
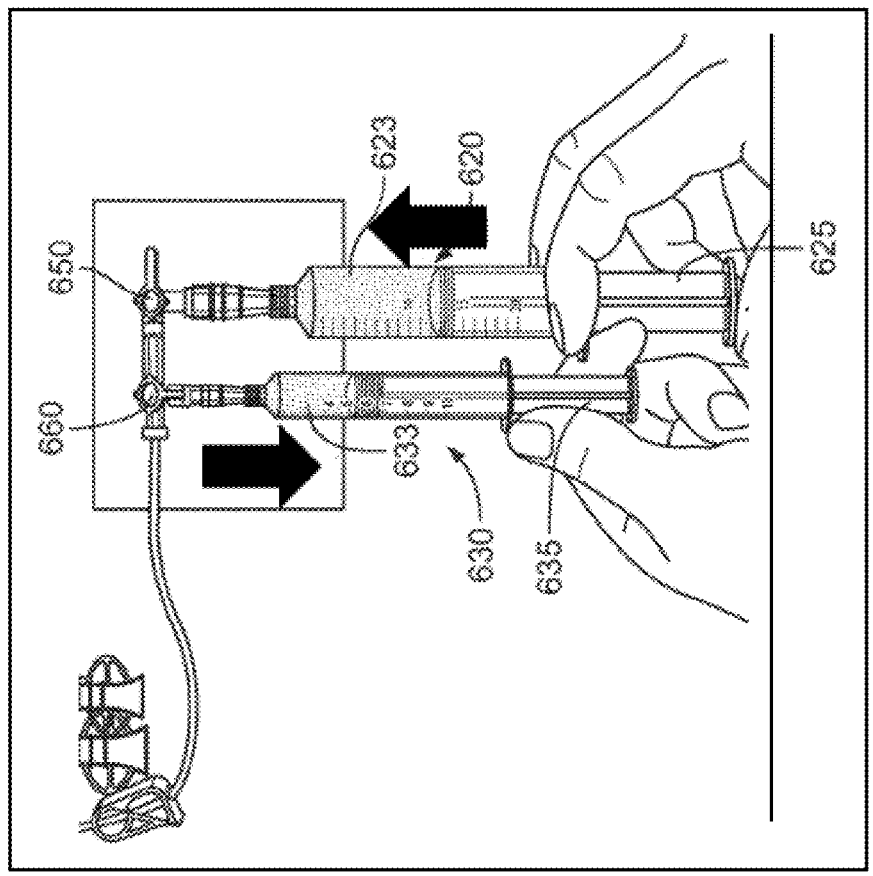
FIG. 14 is a top view of a portion of the mixing assembly of FIG. 6 shown in a first stage of a mixing procedure.

As shown in FIG. 14, the first substance in the syringe barrel 623 of the first syringe 620 can be transferred to the syringe barrel 633 of the second syringe 630 via translating (e.g., pushing) the plunger 625 relative to the syringe barrel 623 such that the first substance is transferred through the first valve 650, through the second valve 660, and into the second syringe 630. In some embodiments, the plunger 635 of the second syringe 630 can be translated (e.g., pulled) simultaneously while the plunger 625 of the first syringe 620 is pushed to assist in transferring the first substance. In some embodiments, the first substance can be transferred to the second syringe 630 at a flow rate sufficiently low to avoid stress to red blood cells (e.g., shear stress and hemolysis) within the first substance (e.g., stress caused by pushing on the plunger 625 too forcefully). For example, the first substance can be transferred to the second syringe 630 at a flow rate ranging from about 0.2 mL per second to about 1 mL per second. In some embodiments, the first substance can be transferred to the second syringe 630 at a flow rate of about 0.5 mL per second. When the first substance is in the second syringe 630, the first substance can combine with the medicament to form a second substance.

Figure 15:
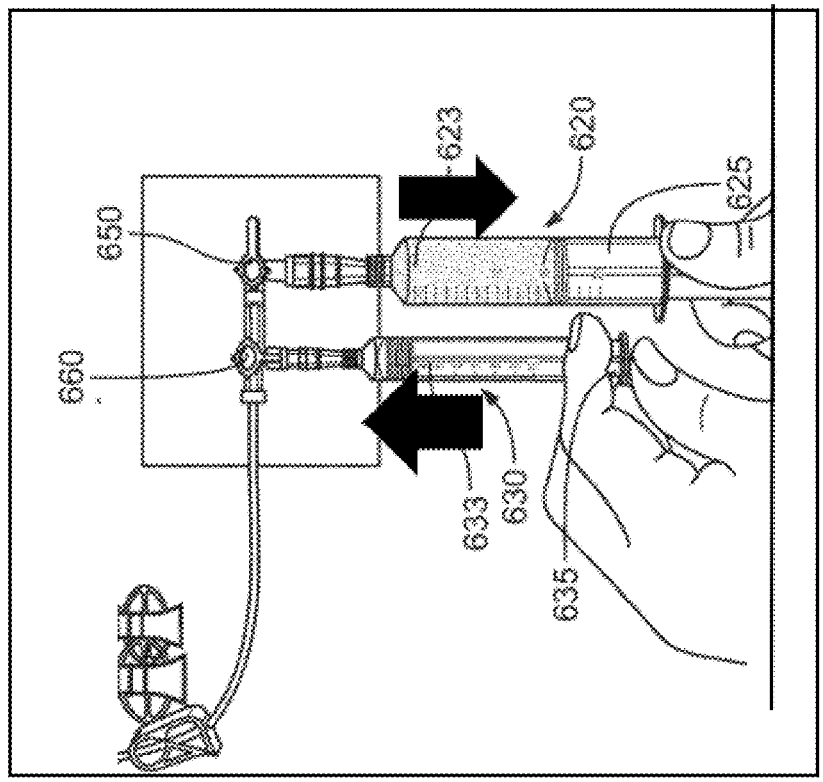
FIG. 15 is a top view of a portion of the mixing assembly of FIG. 6 shown in a second stage of a mixing procedure.

As shown in FIG. 15, the second substance in the syringe barrel 633 of the second syringe 630 can be transferred to the syringe barrel 623 of the first syringe 620 via translating (e.g., pushing) the plunger 635 relative to the syringe barrel 633 such that the second substance is transferred through the second valve 660, through the first valve 650, and into the first syringe 620. In some embodiments, the plunger 625 of the first syringe 620 can be translated (e.g., pulled) simultaneously while the plunger 635 of the second syringe 630 is pushed to assist in transferring the second substance. In some embodiments, the second substance can be transferred to the first syringe 620 at a flow rate sufficiently low to avoid stress to red blood cells within the second substance (e.g., stress caused by pushing on the plunger 635 too forcefully). For example, the second substance can be transferred to the first syringe 620 at a flow rate ranging from about 0.2 mL per second to about 1 mL per second. In some embodiments, the second substance can be transferred to the first syringe 620 at a flow rate of about 0.5 mL per second.

Figure 16:
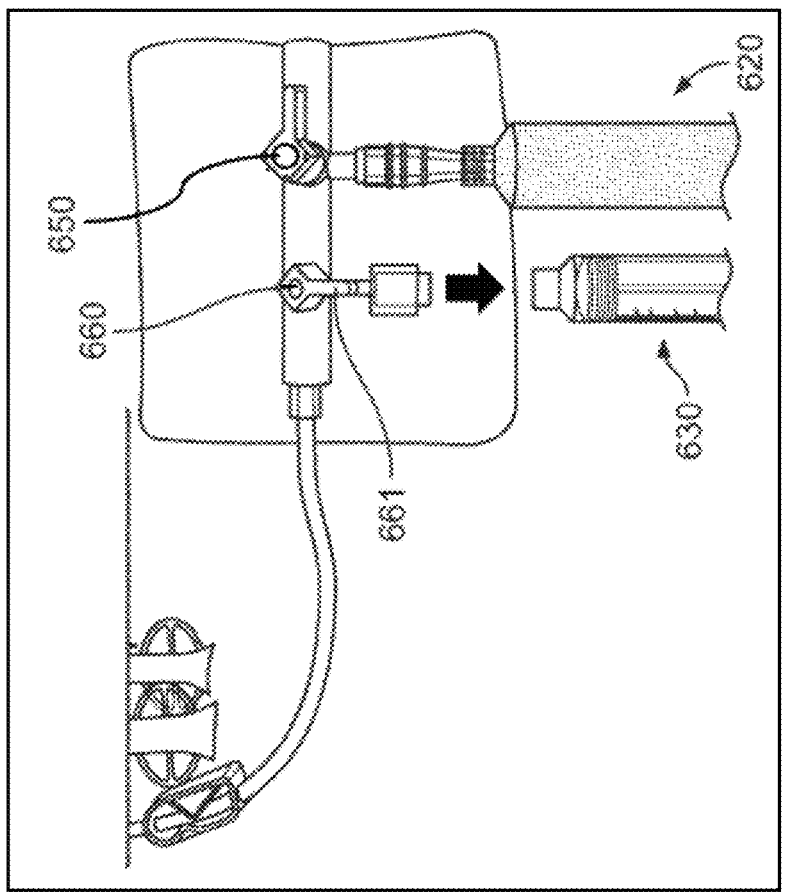
FIG. 16 is a top view of a portion of the mixing assembly of FIG. 6 with a syringe of the mixing assembly detached.

As shown in FIG. 16, the lever 661 of the second valve 660 can be rotated to extend toward the second syringe 630 such that the second syringe 630 is fluidically isolated from the second valve 660. The second syringe 630 can then be decoupled from the second connector 632.

Figure 17:
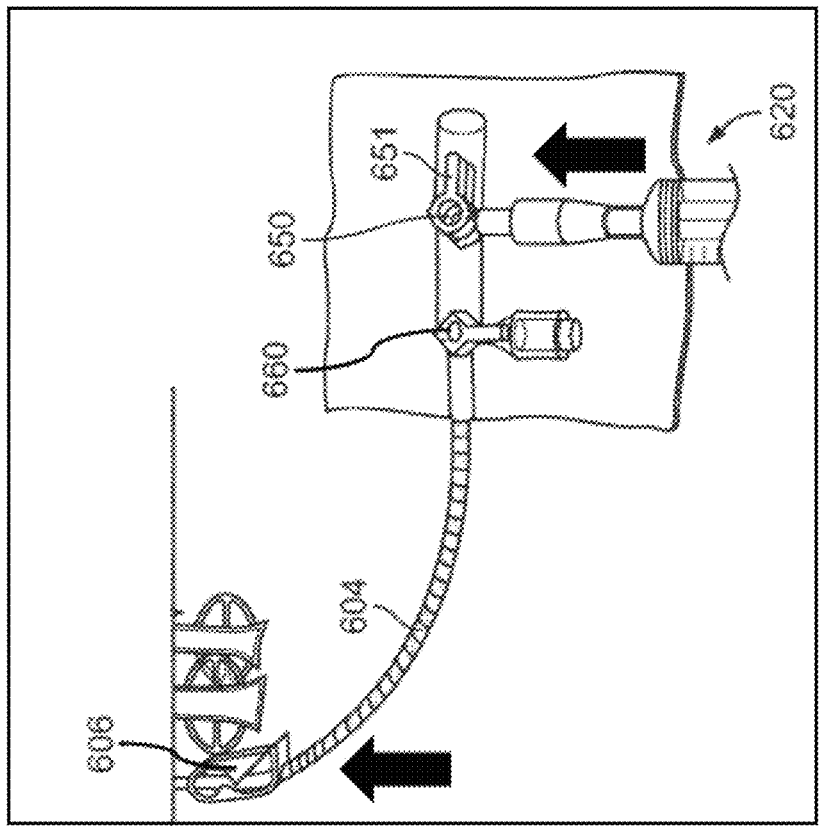
FIG. 17 is a top view of a portion of the mixing assembly of FIG. 6 with a selective fluid flow inhibitor in an open configuration.

As shown in FIG. 17, the first selective flow inhibitor 606 can be transitioned to an open configuration such that fluid can flow through the first tube 604 into the first fluid bag 642. Then, the second substance in the first syringe 620 can be transferred to the first fluid bag 642 via the first tube 604 via translating (e.g., pushing) the plunger 625 of the first syringe 620 such that the second substance is forced out of the first syringe 620, through the first valve 650, the second valve 660, and the first fluid tube 604 into the first fluid bag 642.

Figure 18:
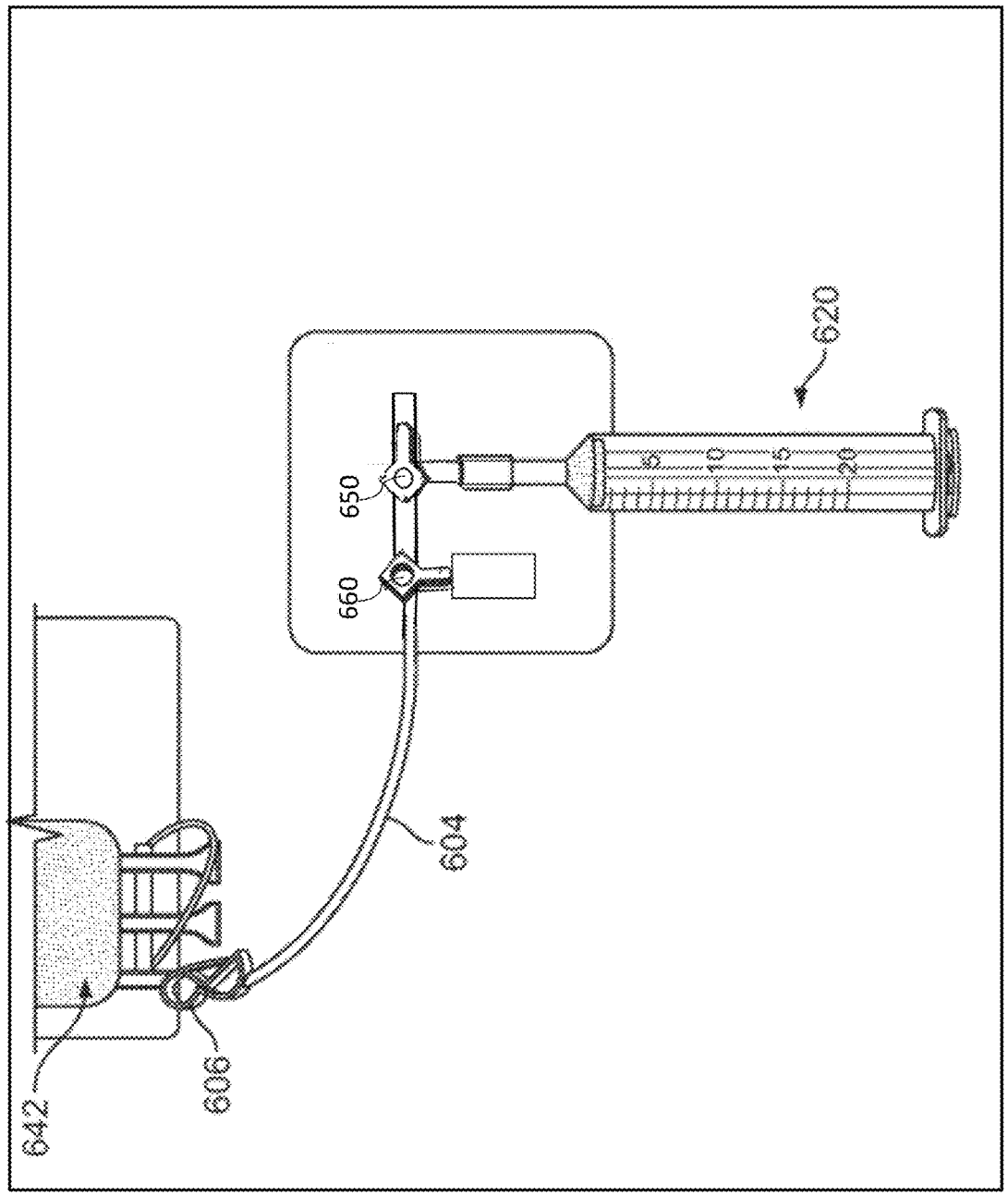
FIG. 18 is a top view of a portion of the mixing assembly of FIG. 6 with a selective fluid flow inhibitor in a closed configuration.

As shown in FIG. 18, the first selective flow inhibitor 606 can be transitioned to the closed configuration such that the third substance in the first fluid bag 642 is prevented from flowing out of the first fluid bag 642 via the first tube 604.

FIG. 19 shows a portion of the system 600 in a configuration in which the system 600 is ready for infusion. As shown, the third tube 605B of the filter subassembly 690 can be fluidically coupled to the second fluid bag 642 via a needle on a first end of the third tube 605B. With a second selective flow inhibitor 608A disposed on the second tube 605C closed to prevent fluid flow through the second tube 605A, the filter subassembly 690 can be primed with saline from the second fluid bag 640. A fourth selective flow inhibitor 608B on the third tubing 605B can then be closed. With the first selective flow inhibitor 618 in a closed configuration on the access tubing 616 and the patient access subassembly 610 still fluidically coupled to the blood vessel of the patient, the fourth tube 605C of the filter subassembly 690 can then be coupled to the third connector 614 of the patient access subassembly 610. The first selective flow inhibitor 618 can then be opened such that the patient access subassembly 610 can be primed.

The second tube 605A of the filter subsassembly 690 can then be fluidically coupled to the first fluid bag 642 via a needle on a first end of the second tube 605A. The third selective flow inhibitor 608A can then be opened to allow the second substance to travel through the second tube 605A, through the filter 691, through the fourth tube 605C, and through the patient access subassembly 610 into the patient. In some embodiments, a pump can be used to transfer the second substance from the first fluid bag 642 to the patient via the patient access subassembly 610. In some embodiments, the second substance can be transferred at a rate of 3 mL/minute for the first 15 minutes of infusion and then increased by 1 mL/minute every 10 minutes for the remainder of the infusion.

When the first fluid bag 642 is empty (i.e., almost all or all of the second substance has been transferred through the second tube 608A), the first fluid bag can be moved to a position lower than the filter 691. The fourth selective flow inhibitor 618 can then be opened to allow a volume of saline (e.g., about 25 mL) to travel from the second fluid bag 640, through the third tubing 605B, through the second tube 605A, and into the first fluid bag 642 to combine with any remaining second substance in the first fluid bag 642. The fourth selective flow inhibitor 618 can then be closed on the third tubing 605B. The first fluid bag 642 can then be raised above the filter 691 such that the second substance and saline combination in the first fluid bag 642 can be transferred to the patient (e.g., at the highest fluid rate used during the initial transfer of the second substance). Once the first fluid bag 642 is empty, the third selective flow inhibitor 608A can be closed to clamp off the second tube 605A and the fourth selective flow inhibitor 608B can be opened to allow saline from the second fluid bag 640 to flush filter subassembly 690 and the patient access subassembly 610 until the tubing of the filter subassembly 690 and patient access subassembly 610 are clear (i.e., the saline has pushed the second substance and saline combination through the tubing of the filter subassembly 690 and the patient access subassembly 610).

Thus, the system 600 can function as a closed loop system in which fluid can flow away from the patient access subassembly 610 via the assembly 640 and return to the patient access subassembly 610 via the second tube 605A, the filter 691, and the fourth tube 605C.

Figure 20:
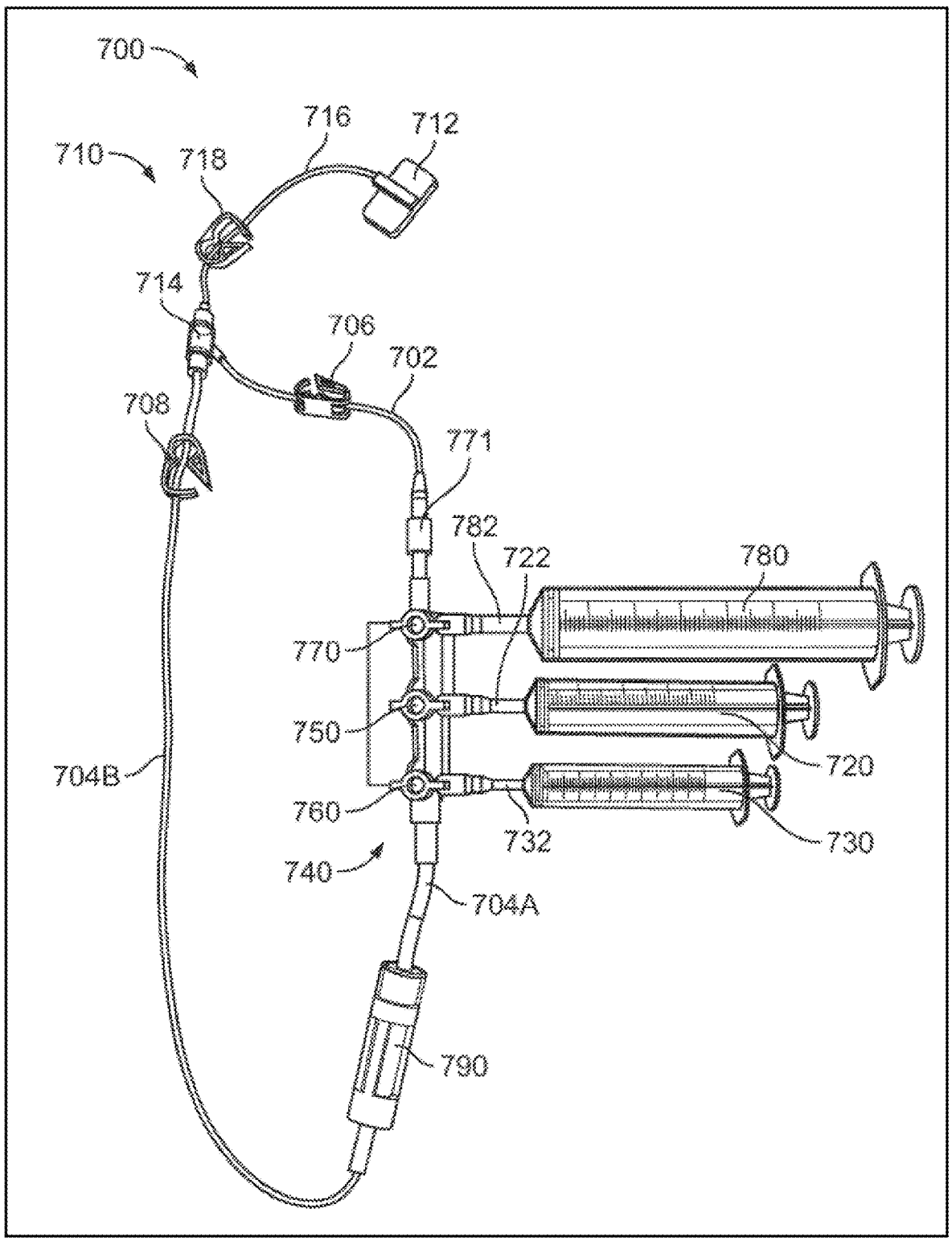
FIG. 20 is a top view of an example system, according to an embodiment.

FIG. 20 is a top view of a system 700 in an assembled configuration. The system 700 can be the same or similar in structure and/or function to any of the systems described herein, such as the system 100 or the system 200. Unless explicitly noted otherwise, similarly named and referenced components can be structurally and/or functionally similar to those described above with reference to, for example, FIGS. 1 and 2. In some embodiments, the system 700 is useful for drawing cells (e.g., packed red blood cells, white blood cells, and/or platelets) from a patient, combining medicament with the cells of the patient ex vivo, and infusing the combined cells and medicament into the patient's bloodstream. The system 700 includes a patient access subassembly 710, a first syringe 720 defining a first fluid reservoir, a second syringe 730 defining a second fluid reservoir, a third syringe 780 defining a third fluid reservoir, and an assembly 740. The assembly 740 includes a first valve 750, a second valve 760, and a third valve 770. In some embodiments, the assembly 740 can include a 3-gang valve manifold. Each valve of the first valve 750, the second valve 760, and the third valve 770 includes a valve lever to control the flow of fluid through the valve. The direction of extension of the valve lever can indicate the direction of the fluid line that is isolated or "off." The first syringe 720 can be coupled to the first valve 750 via a first connector 722 and the second syringe 730 can be coupled to the second valve 760 via a second connector 732. The first valve 750 can be engaged with the third valve 770 and the second valve 760 such that the first valve 750 can be in fluidic communication with the third valve 770 and the second valve 760. The third syringe 780 can be coupled to the third valve 770 via a third connector 782. In some embodiments, the third syringe 780 can be separate from the assembly 740 during a portion of the use of the system 700. The first connector 732, the second connector 722, and/or the third connector 782 can be needleless connectors (also referred to as needle free connectors). For example, the first connector 732, the second connector 722, and/or the third connector 782 can be an ICU Medical MC100 MicroClave Neutral Connector. The system 700 also includes a first tube 702, a second tube 704A, a third tube 704B, and a filter 790, the second tube 704A coupled to the second valve 760 and the filter 790, the third tube 704B coupled to the patient access subassembly 710 and the filter 790. In some embodiments, the filter 790 can be, for example, a 150 micron filter. In some embodiments, the filter 790 can be a 170 micron filter to a 260 micron filter.

In an example use scenario, the second fluid reservoir 730 can include medicament, such as 2-Bromo-1-(3,3-dinitroazetidin-1-yl)ethanone, propofol nitric oxide, and/or ozone. The system 700 can be attached to a patient via the patient access subassembly 710. A volume of blood of the patient can be drawn through the patient access subassembly 710, through the first tube 702, through the assembly 740, and into the first fluid reservoir 720. A portion of the volume of blood drawn can be transferred to the second fluid reservoir 730 via the assembly 740 such that the portion combines with the medicament in the second fluid reservoir 730 to form a first combined substance. The first combined substance can then be returned to the first fluid reservoir 720 via the assembly 740 to combine with the remaining blood in the first fluid reservoir 720 to form a second combined substance. The second combined substance can then be pushed through the assembly 740, through the second tube 704A, through the filter 790, through the third tube 704B, and through the patient access subassembly 710 such that the second combined substance flows into the bloodstream of the patient.

The patient access subassembly 710 can include a patient access port 712, access tubing 716, and a connector 714. The patient access port 712 can include any suitable element configured to provide access to a patient's vasculature system. For example, the patient access subassembly 710 can include a needle, such as, for example, a Huber needle. In some embodiments, the patient access subassembly 710 can include a connector configured to couple to a port previously coupled to the patient's vasculature system. The connector 714 of the patient access subassembly 710 can be coupled to the third valve 770 via the first tube 702 such that the patient access subassembly 710 can be in fluid communication with the third valve 770 via a first fluid route. In some embodiments, the patient access subassembly 710 includes the first tube 702. The connector 714 can be coupled to the second valve 760 via a second fluid route including the second tube 704A, the third tube 704B, and the filter 790 such that the patient access subassembly 710 can be in fluid communication with the second valve 760 via the second fluid route. Thus, the system 700 can function as a closed loop system in which fluid can flow away from the patient access subassembly 710 via the first tube 702 and return to the patient access subassembly 710 via the second tube 704A, the filter 790, and the third tube 704B. In some embodiments, the patient access subassembly 710 can be 19 G×0.75" or 19 G×1". In some embodiments, the patient access subassembly 710 can be a BARD EZ Huber SHQ19-75YS or 100YS. In some embodiments, the patient access subassembly 710 can include a needle having a needle length depending on a size of a patient (e.g., a needle length of 1", 1.25", or 1.5").

Each of the first valve 750, the second valve 760, and the third valve 770 can be configured to transition between two or more configurations, each configuration corresponding to a different available flow path through the assembly 740. Each of the first valve 750, the second valve 760, and the third valve 770 can include any suitable valve mechanism, such as, for example, a manual valve mechanism, a solenoid-actuated valve mechanism, a motor-operated valve mechanism, a hydraulic valve mechanism, and/or a pneumatic valve mechanism. For example, each of the first valve 750, the second valve 760, and the third valve 770 can include a three-way stopcock. Each of the first valve 750, the second valve 760, and the third valve 770 can define or include an interior region such that fluid can travel through the interior region. The first syringe 720 can be coupled to the first valve 750 such that the first syringe 720 can be in selective fluid communication with the patient access subassembly 710 via the third valve 770 and the first valve 750, the second syringe 730 via the first valve 750 and the second valve 760, or the second tube 704 via the first valve 750 and the second valve 760. For example, the first valve 750 can have a first configuration in which the first valve 750 allows fluid communication between an interior region of the third valve 770 and the first syringe 720, but fluidically isolates the second valve 760 from both the first syringe 720 and the interior region of the third valve 770. The first valve 750 can have a second configuration in which the first valve 750 allows fluid communication between the first syringe 720 and an interior region of the second valve 760, but fluidically isolates the third valve 770 from both the first syringe 720 and the interior region of the second valve 760. The first valve 750 can have a third configuration in which the first valve 750 allows fluid communication between the interior region of the third valve 770 and the interior region of the second valve 760, but fluidically isolates the first syringe 720 from both the interior region of the third valve 770 and the interior region of the second valve 760.

In some embodiments, the second syringe 730 can be coupled to the second valve 760 such that the second syringe 730 can be in selective fluid communication with the first syringe 720 via the second valve 760 and the first valve 750 and with the patient access subassembly 710 via the second valve 760. For example, the second valve 760 can have a first configuration in which the second valve 760 allows fluid communication between an interior region of the first valve 750 and the second syringe 730, but fluidically isolates the second tube 704A from both the second syringe 730 and the interior region of the first valve 750. The second valve 760 can have a second configuration in which the second valve 760 allows fluid communication between the interior region of the first valve 750 and the second tube 704A, but fluidically isolates the second syringe 730 from both the interior region of the first valve 750 and the second tube 704A.

The third valve 770 can be coupled to the first valve 750 such that the patient access subassembly 710 and the third syringe 780 can each be in selective fluid communication with the first syringe 720 and/or the second tube 704A via the third valve 770. For example, the third valve 770 can have a first configuration in which the third valve 770 allows fluid communication between the first tube 702 and the interior region of the first valve 750, but fluidically isolates the third syringe 780 (or a connector configured to be coupled to the third syringe 780) from both the first tube 702 and the interior region of the first valve 750. The third valve 770 can have a second configuration in which the third valve 770 allows fluid communication between the third syringe 780 and the interior region of the first valve 750, but fluidically isolates the first tube 702 from both the interior region of the first valve 750 and the third syringe 780.

Thus, the assembly 740 can have a first assembly configuration in which the patient access subassembly 710 is in fluid communication with the first syringe 720 via the first tube 702, a second assembly configuration in which the first syringe 720 is in fluid communication with the second syringe 730, and a third assembly configuration in which the first syringe 720 is in fluid communication with the patient access subassembly 710 via the second tube 704A. In the first assembly configuration, the first valve 750 can be in the first configuration of the first valve 750 and the third valve 770 can be in the first configuration of the third valve 770 such that the first tube 702 and the first syringe 720 can be in fluid communication between the third valve 770 and the first valve 750. In the first assembly configuration, the second valve 760 can be in either the first or second configuration of the second valve 760 because the second valve 760 is isolated from the flow path from the patient access subassembly 710, through the first tube 702, the third valve 770, the first valve 750, and into the first syringe 720.

In the second assembly configuration, the first valve 750 can be in the second configuration of the first valve 750 and the second valve 760 can be in the first configuration of the second valve 760 such that the first fluid first reservoir 720 and the second syringe 730 are in fluid communication via the first valve 750 and the second valve 760. The third valve 770 can be in either the first or second configuration of the third valve 770 because the third valve 770 is isolated from the flow path between the first syringe 720 and the second syringe 730 via the first valve 750 and the second valve 760.

In the third assembly configuration, the first valve 750 can be in the third configuration of the first valve 750 and the second valve 760 can be in the second configuration of the second valve 760 such that the first syringe 720 can be in fluid communication with the second tube 704A. The third valve 770 can be in either the first or second configuration of the third valve 770 because the third valve 770 is isolated from the flow path between the first syringe 720 and the second tube 704A via the first valve 750 and the second valve 760.

In some embodiments, the assembly 740 can have a fourth assembly configuration in which the third syringe 780 is in fluid communication with the second tube 704A. In the fourth assembly configuration, the first valve 750 can be in the third configuration of the first valve 750, the second valve 760 can be in the second configuration of the second valve 760, and the third valve 770 can be in the second configuration of the third valve 770 such that the third syringe 780 is in fluid communication with the second tube 704A (and the patient access subassembly 710) via the third valve 770, the first valve 750, and the second valve 760. In the fourth assembly configuration, the flow path from the third syringe 780 to the second tube 704A can be fluidically isolated from the first tube 702, the first syringe 720, and the second syringe 730.

In some embodiments, the first syringe 720 can include (e.g., be prefilled with) an anti-coagulant, such as, for example, ACD-A, ACD-B, EDTA, or heparin. For example, the first syringe 720 can include about 1.5 mL of ACD-A anticoagulant. In some embodiments, the first syringe 720 can be prefilled with both an anti-coagulant and an antioxidant (e.g., vitamin C or N-acetylcysteine). In some embodiments, the second syringe 730 can include (e.g., be prefilled with) a medicament, such as, for example, 2-Bromo-1-(3, 3-dinitroazetidin-1-yl)ethanone, propofol, a nitric oxide donor, a chemotherapy drug, and/or ozone. In some embodiments, the third syringe 780 can include (e.g., be prefilled with) saline or Ringer's lactate solution. In some embodiments, the first syringe 720 can have a volume of 20 mL, and the second syringe 730 can have a volume of 10 mL. In some embodiments, the second syringe 730 can have a volume of less than 10 mL, e.g., the second syringe 730 can have a volume of 3 mL when used with lower amounts of a medicament (e.g., 0.5-2 mg). In some embodiments, the second syringe 730 can be pre-filled with between 0.25 mL and 5 mL of medicament, containing between 0.5 and 4 mg of medicament, respectively. In some embodiments, the third syringe 780 can have a volume of 60 mL.

As shown in FIG. 20, the system 700 can include a number of selective flow inhibitors coupled to tubing of the system 700 such that the flow through the tubing can be temporarily inhibited. For example, a first selective flow inhibitor 718 can be disposed on the access tube 716, a second selective flow inhibitor 706 can be disposed on the first tube 702, and a third selective flow inhibitor 708 can be disposed on the third tube 704B. Each of the first selective flow inhibitor 718, the second selective flow inhibitor 706, and the third selective flow inhibitor 708 can be, for example, tubing clamps or roller clamps.

Figure 21:
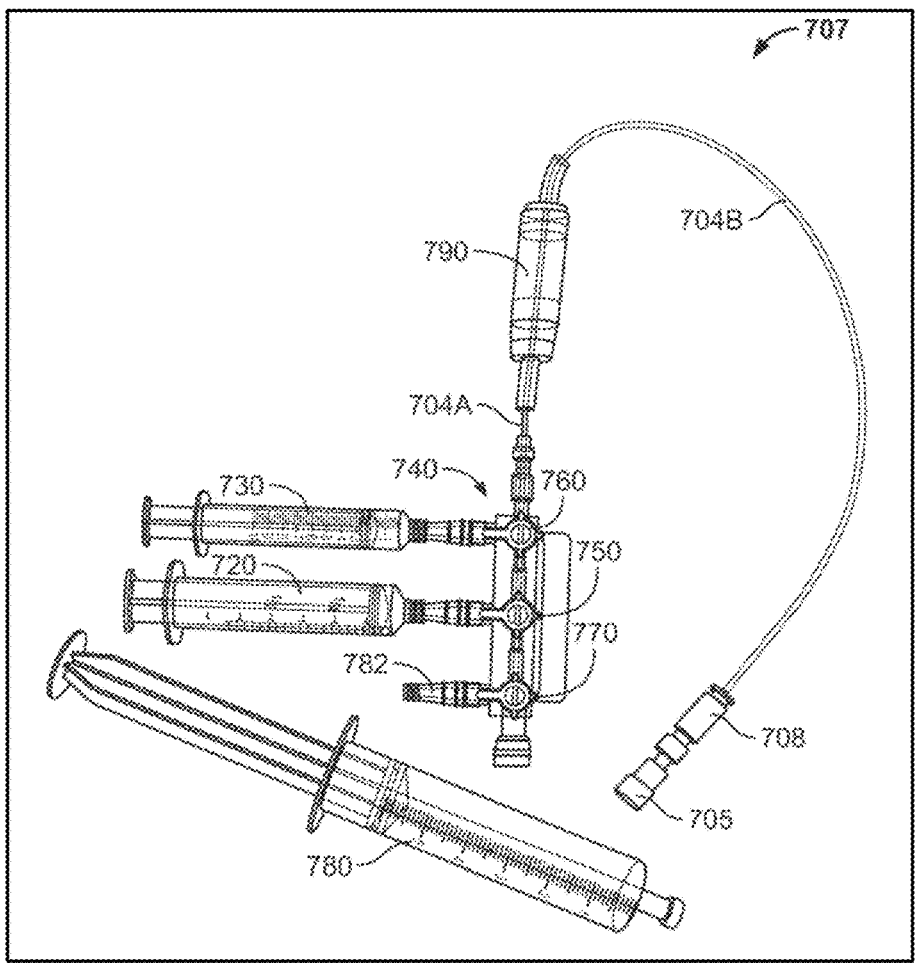
FIG. 21 is a top view of a mixing assembly of the system of FIG. 20 in a partially assembled configuration.
Figure 22:
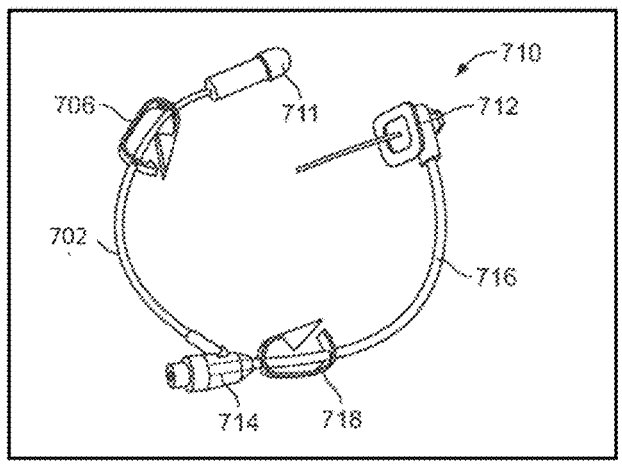
FIG. 22 is a top view of a patient access subassembly of the system of FIG. 20.
Figure 23:
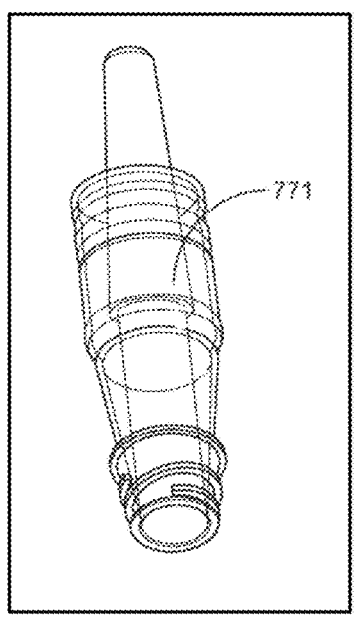
FIG. 23 is a perspective view of an subassembly connector of the system of FIG. 20.

As shown in FIGS. 21-34, the system 700 can be assembled from a kit of separate components. FIGS. 21-23 show various views of the components of the system 700 prior to assembly. Specifically, FIG. 21 shows a mixing assembly 707, which is a subassembly of the system 700 including the assembly 740, the first syringe 720, the second syringe 730, the second tube 704A, the filter 790, and the third tube 704B. As shown, the third tube 704B is coupled to the filter 790 at a first end and a coupler 705 at a second end. Additionally, the mixing assembly 707 includes the connector 782 coupled to the third valve 770 of the assembly 740. As shown, in the pre-assembled configuration, each valve of the assembly 740 can be configured to isolate each valve from their respective connectors and/or syringes. Further, as described above, each valve of the assembly 770 includes a valve lever extending in the "off" direction of the respective valve, representing which flow path is closed with respect to the particular valve. Specifically, the first valve 750 is configured in the third configuration of the first valve 750 (e.g., with the lever of the first valve 750 directed toward the first connector 722) such that the first connector 722 and first syringe 720 are fluidically isolated from the assembly 740. The second valve 760 is configured in the second configuration of the second valve 760 (e.g., with the lever of the second valve 760 directed toward the second connector 732) such that the second connector 732 and second syringe 730 are fluidically isolated from the assembly 740. The third valve 770 is configured in the first configuration of the third valve 770 (e.g., with the lever of the third valve 770 directed toward the third connector 782) such that the third connector 782 is fluidically isolated from the assembly 740. The assembly 740, the second tube 704A, the filter 790, and the third tube 704B can be primed with saline (e.g., 0.9% Sodium Chloride) prior to delivery to the user (e.g., by a pharmacy). Further, the third tube 704B can be pinched closed by the third selective flow inhibitor 708. In some embodiments, the mixing assembly 707 can be packaged (e.g., by a pharmacy) in a sterile pouch or container separate from other components of the system 700 prior to use. A user (e.g., a clinician, doctor, or nurse) can unpackage the mixing assembly 707 to assemble the system 700 for use.

Additionally, the third syringe 780 can be provided separately from the mixing assembly 707 and uncoupled from the connector 782. Further, the first fluid reservoir 720 can be prefilled with a volume of anti-coagulant. The second fluid reservoir 730 can be prefilled with a volume of medicament. The third fluid reservoir 780 can be prefilled with a volume of saline. In some embodiments, the third fluid reservoir 780 can be included in the same sterile pouch or container as the other components of the mixing assembly 707. In some embodiments, the third fluid reservoir 780 can be packaged separately (e.g., in another sterile pouch or container).

As shown in FIG. 22, the patient access subassembly 710 can also be provided independent from the mixing assembly 707. The patient access subassembly 710 can be provided with an end cap 711 on the end of the first tube 702 opposite from the connector 714. Furthermore, FIG. 23 shows an access connector 771, which can be provided with the other components of the system 700. The access connector 771 can be a needleless connector (also referred to as a needle free connector) configured to be coupled to tubing or a fluid inlet/outlet. The access connector 771 can be the same or similar in structure and/or function to the first connector 732, the second connector 722, and/or the third connector 782. Additionally, the first selective flow inhibitor 718 and the second selective flow inhibitor 706 can each be in the closed position such that flow is inhibited through the access tube 716 and the first tube 702, respectively. In some embodiments, the patient access subassembly 710 can be packaged (e.g., by a pharmacy) in a sterile pouch or container separate from other components of the system 700 prior to use. A user (e.g., a clinician, doctor, or nurse) can unpackage the patient access subassembly 710 to assemble the system 700 for use.

Figure 24:
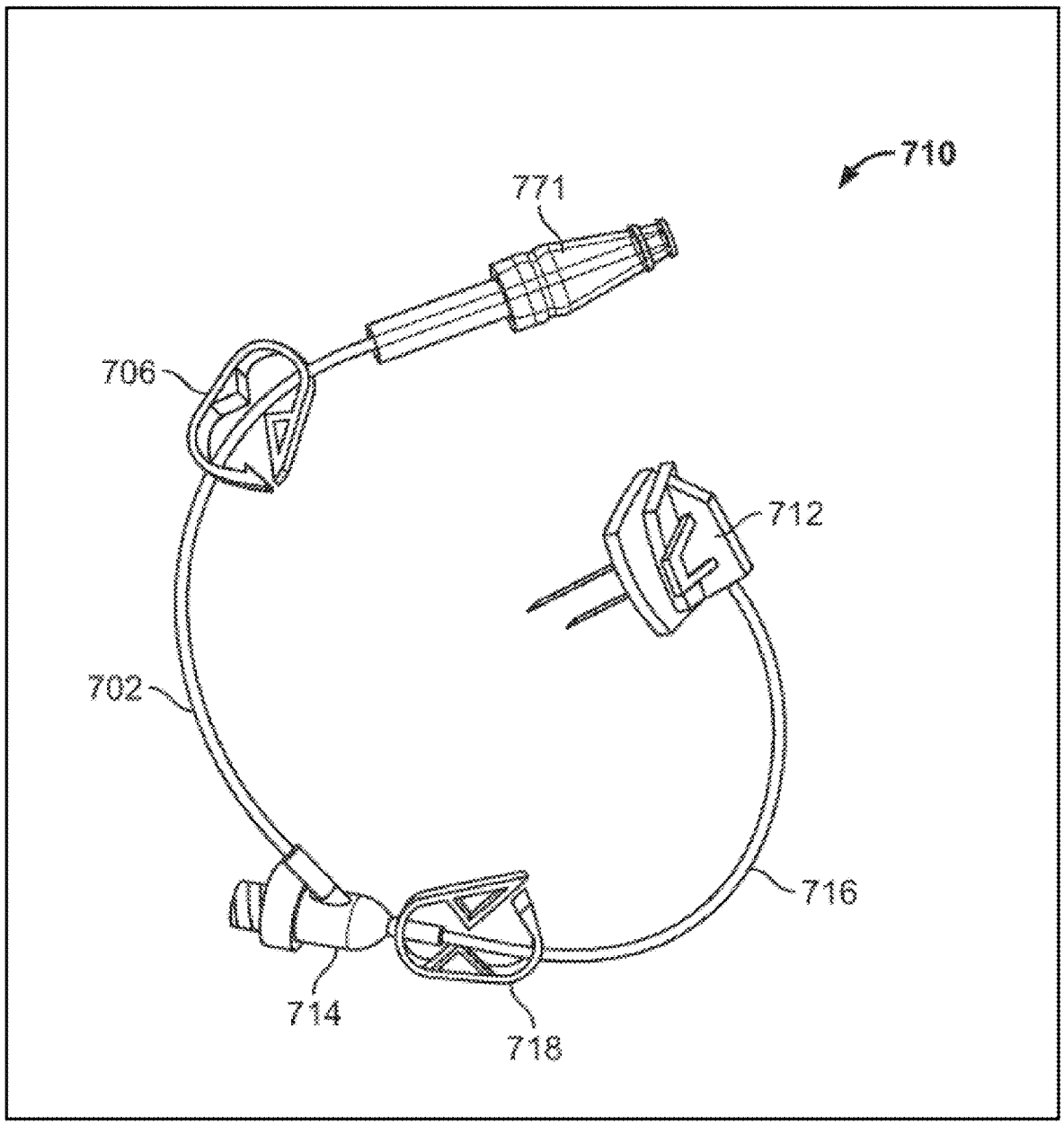
FIG. 24 is a top view of the patient access subassembly of the system of FIG. 22 coupled to the subassembly connector of FIG. 23.

As shown in FIG. 24, the end cap 711 of the patient access subassembly 710 can be removed and replaced with the access connector 771. The access connector 771 can then be swabbed with an alcohol pad, which can be included in a kit with the other components of the system 700.

Figure 25:
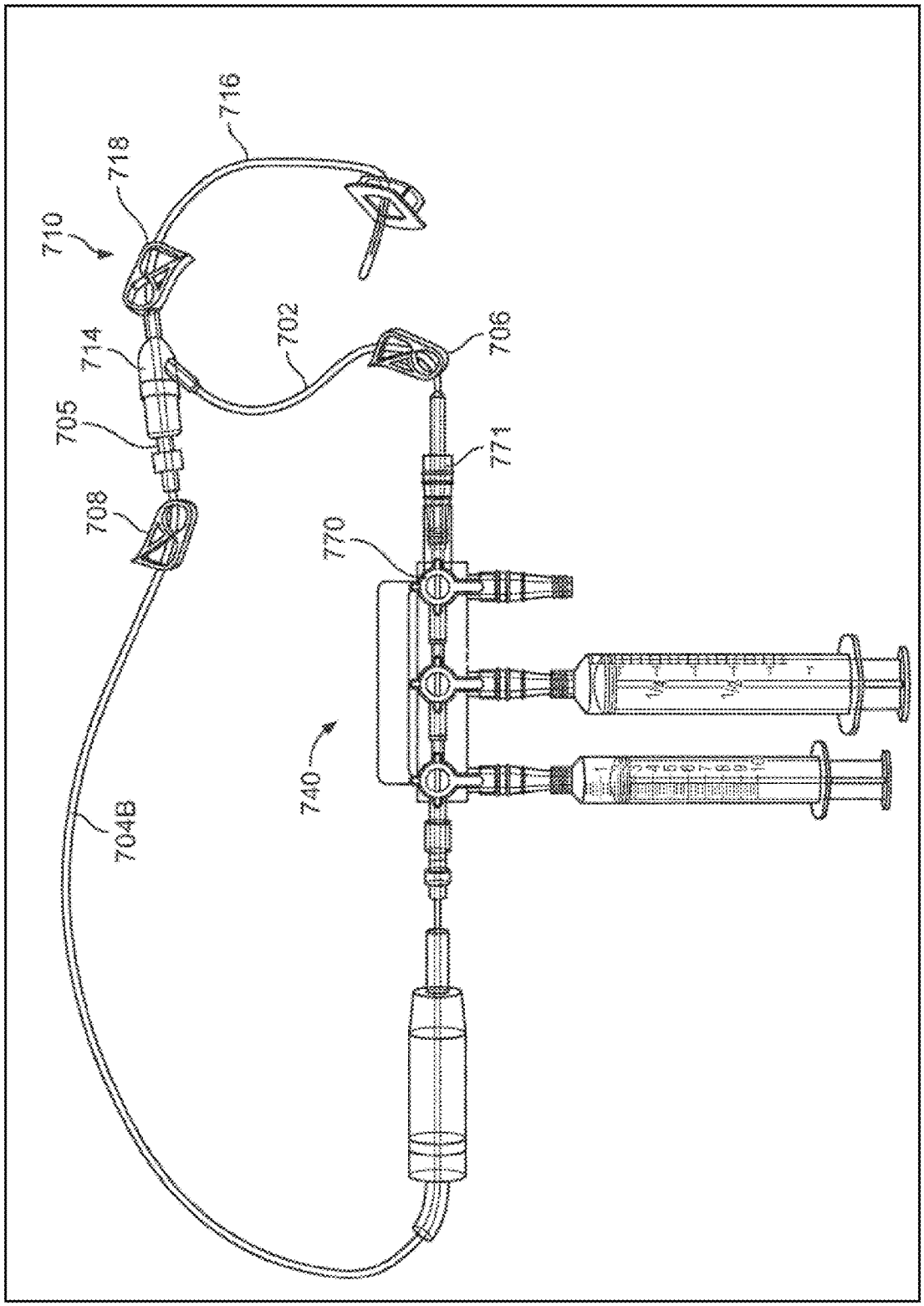
FIG. 25 is a top view of the system of FIG. 20 with the patient access subassembly coupled to the mixing assembly.

As shown in FIG. 25, the access connector 771 can be coupled to the third valve 770 of the assembly 740 via, for example, removing a cap on a port of the third valve 770 and coupling the access connector 771 to the port. Additionally, the coupler 705 of the third tube 704B can be coupled to the connector 714 via removing a cap on the coupler 705, swabbing the coupler 705 with an alcohol pad, and coupling the coupler 705 to the connector 714. The patient access subassembly 710 can be placed in fluid communication with a patient's vasculature via the patient access port 712 (e.g., via inserting a needle of the patient access port 712 through a patient's skin or via coupling the patient access port 712 to an existing port through a patient's skin (e.g., peripherally inserted central catheter)). In some embodiments, the patient access subassembly 710 can be placed in fluid communication with a patient's vasculature via the patient access port 712 prior to coupling the patient access subassembly 710 to the mixing assembly 707. For example, a user (e.g., a clinician, doctor, or nurse) can couple the patient access port 712 to a patient's vasculature via, for example, a connector coupled to tubing already in place in the patient, and then verify that blood flows into the access tubing 716 and the first tube 702 prior to coupling the first tube 702 to the assembly 740 and the connector 714 to the coupler 705 on the end of the third tube 704B.

Figure 26:
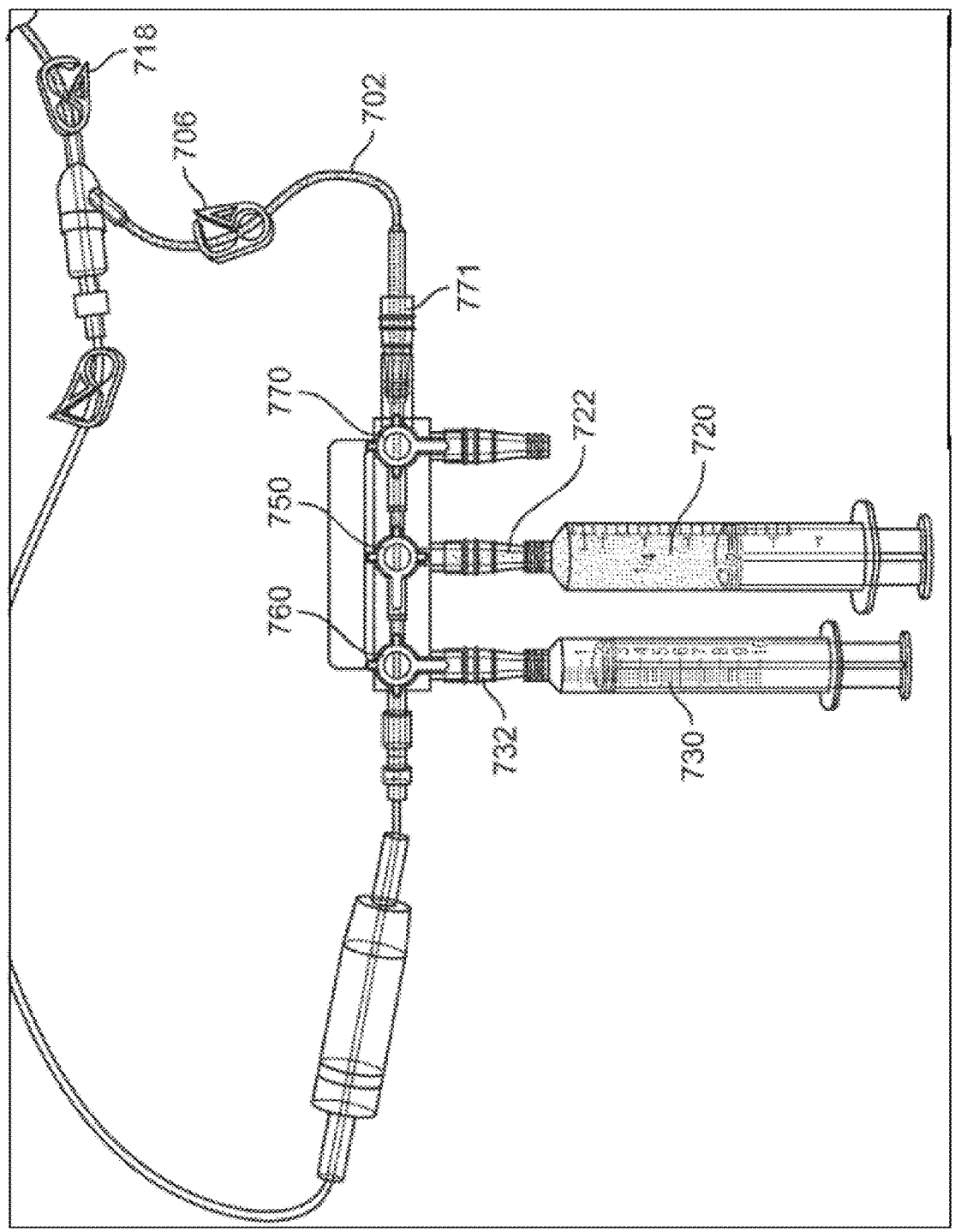
FIG. 26 is a top view of the system of FIG. 20 during a blood draw stage of an administration procedure.

As shown in FIG. 26, the assembly 740 can be arranged in the first assembly configuration such that the patient access subassembly 710 is in fluid communication with the first syringe 720 via the first tube 702, the third valve 770, and the first valve 750. For example, the first valve 750 can be manipulated or toggled into the first configuration of the first valve 750 (e.g., the lever of the first valve 750 can be rotated such that the interior region of the first valve 750 is fluidically isolated from the interior region of the second valve 760 and such that the syringe 730 is in fluid communication with the patient access port 712). Next, the first selective flow inhibitor 718 and the second selective flow inhibitor 706 can each be transitioned to an open configuration such that fluid can flow through the access tube 716 and the first tube 702, respectively.

Blood can then be drawn from the patient, through the patient access subassembly 710, the first tube 702, the third valve 770, the first valve 750, and into the first fluid reservoir 720 such that the blood combines with the anticoagulant within the first syringe 720 to form a first substance. For example, a plunger of the first syringe 720 can be translated relative to a barrel of the first syringe 720 to draw blood into the first syringe 720. In some embodiments, 12 mL of blood can be drawn into the first syringe 720 to combine with the anticoagulant. For example, the 12 mL of blood can combine with 1.5 mL of anticoagulant previously drawn into the first fluid reservoir 720 such that the first fluid reservoir 720 contains 13.5 mL of the first substance. In some embodiments, between about 10 mL and about 14 mL of blood can be drawn into the first syringe 720 to combine with the anticoagulant.

Figure 27:
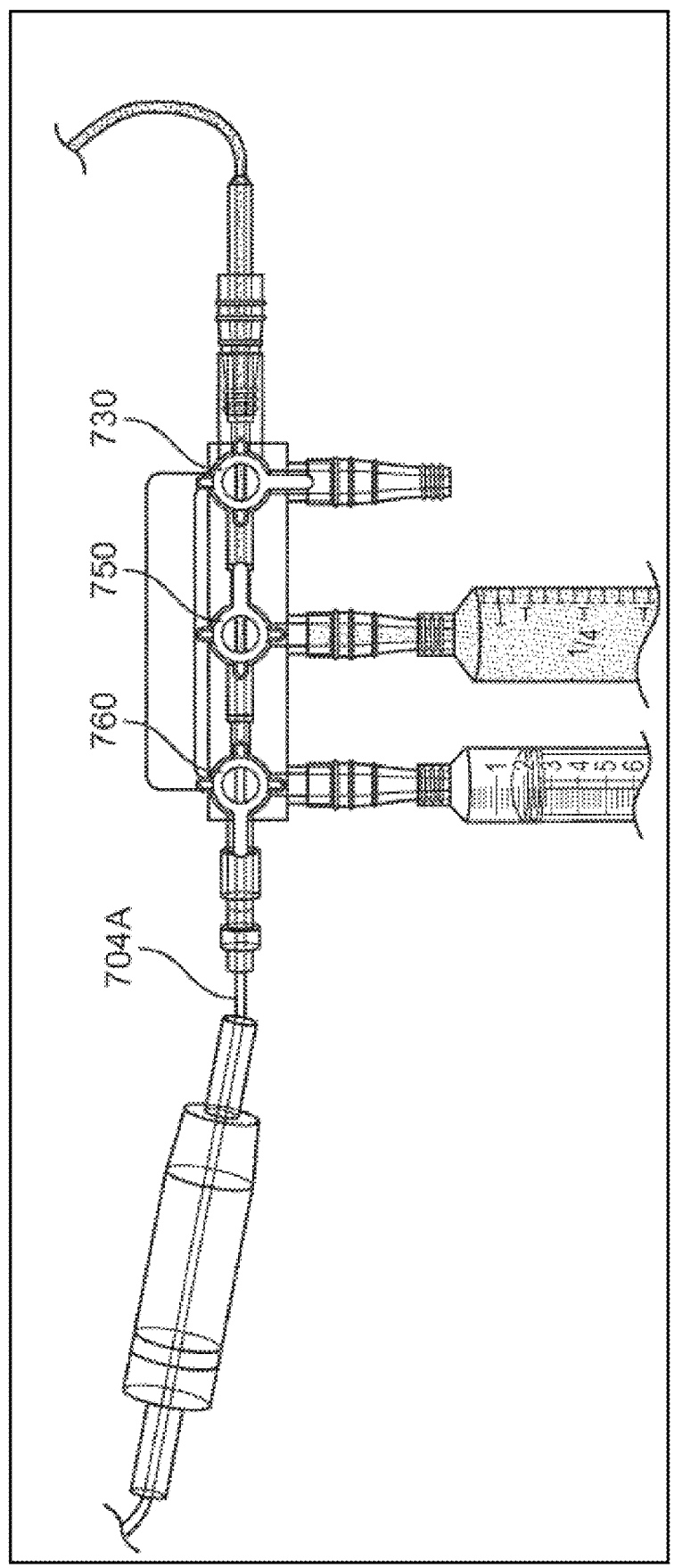
FIG. 27 is a top view of a portion of the mixing assembly of FIG. 21 in a mixing configuration.

As shown in FIG. 27, the assembly 720 can then be transitioned to the second assembly configuration such that the first syringe 720 is in fluid communication with the second syringe 730. For example, the first valve 750 and the second valve 760 can be manipulated or toggled such that the first valve 750 is in the second configuration of the first valve 750 and the second valve 760 is in the first configuration of the second valve 760 (e.g., the lever of the first valve 750 is directed toward the third valve 730 such that the interior region of the first valve is fluidically isolated from the interior region of the third valve 730 and the lever of the second valve 720 is directed toward the second tube 704A such that the interior region of the second valve 720 is fluidically isolated from the second tube 704A). Additionally, the first selective flow inhibitor 718 and the second selective flow inhibitor 706 can each be transitioned to a closed configuration such that fluid flow through the access tube 716 and the first tube 702, respectively, is inhibited.

Figure 28:
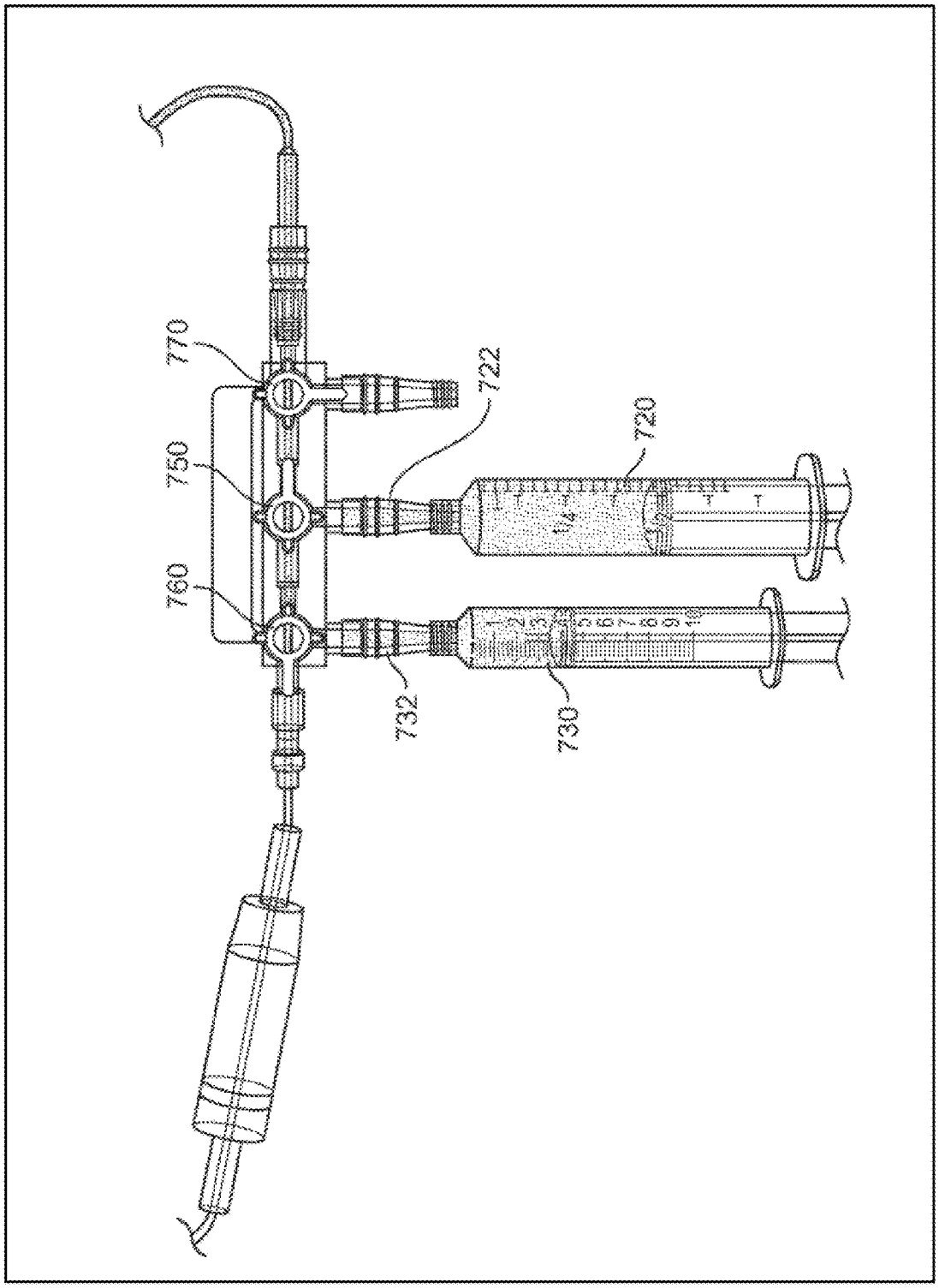
FIG. 28 is a top view of a portion of the mixing assembly of FIG. 21 during a mixing stage of an administration procedure.

As shown in FIG. 28, a portion of the first substance can then be transferred from the first syringe 720 to the second syringe 730 such that the portion of the first substance combines with the medicament within the second syringe 730 to form a second substance. For example, the plunger of the first syringe 720 can be translated to expel the portion of the first substance from the first syringe 720 and push the first substance into the second syringe 730. In some embodiments, a plunger of the second syringe 730 can be simultaneously translated relative to a barrel of the second syringe 730 to assist in drawing the first substance into the second syringe 730. In some embodiments, the portion of the first substance transferred can be equal the volume of medicament in the second syringe 730. For example, the second syringe 730 can contain 2 mL of medicament (e.g., a 4 mg dose of 2-Bromo-1-(3,3-dinitroazetidin-1-yl)ethanone, propofol nitric oxide, and/or ozone) prior to assembly of the system 700, and 2 mL of the first substance can be transferred from the first syringe 720 to the second syringe 730 such that the second syringe 730 contains 4 mL of the second substance. Additionally, in some embodiments the first substance can be transferred from the first syringe 720 to the second syringe 730 at a flow rate sufficiently low to avoid stress to red blood cells (e.g., shear stress and hemolysis) within the first substance (e.g., stress caused by pushing on the plunger of the first syringe 720 too forcefully). For example, the first substance can be transferred to the second syringe 730 at a flow rate ranging from about 0.2 mL per second to about 1 mL per second. In some embodiments, the first substance can be transferred to the second syringe 730 at a flow rate of about 0.5 mL per second.

Figure 29:
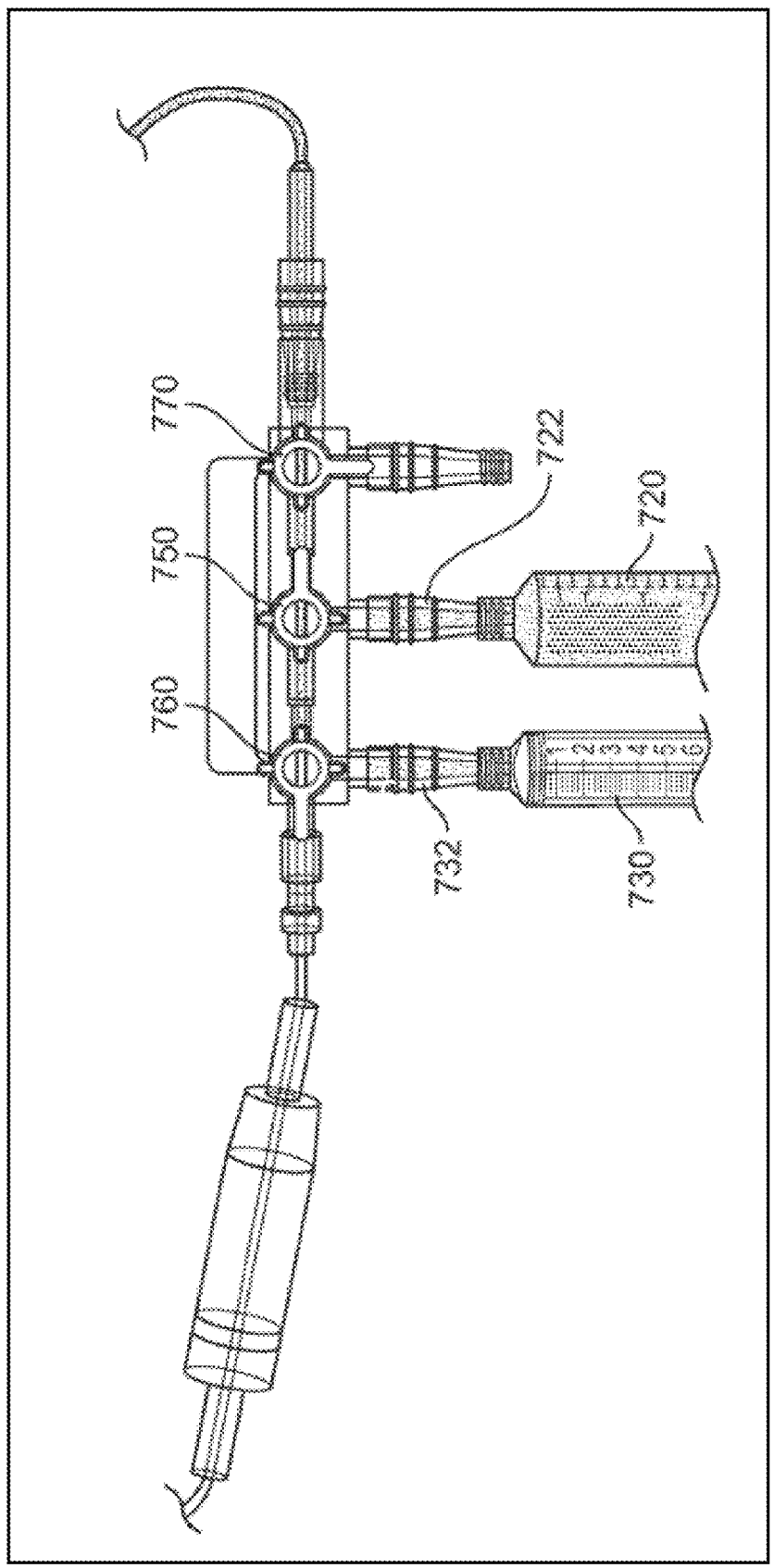
FIG. 29 is a top view of a portion of the mixing assembly of FIG. 21 in a fully mixed, pre-infusion configuration.

As shown in FIG. 29, while the assembly 740 remains in the second assembly configuration, the second substance can be transferred from the second syringe 730 to the first syringe 720 such that the second substance combines with the remaining portion of the first substance in the first syringe 720 to form a third substance. For example, the plunger of the second syringe 730 can be translated to expel the second substance from the second syringe 730 and push the second substance into the first syringe 720 via the second valve 760 and the first valve 750. In some embodiments, the plunger of the first syringe 720 can be simultaneously translated to assist in drawing the second substance into the first syringe 720. Additionally, in some embodiments the second substance can be transferred from the second syringe 730 to the first syringe 720 at a flow rate sufficiently low to avoid stress to red blood cells within the second substance (e.g., stress caused by pushing on the plunger of the second syringe 730 too forcefully). For example, the second substance can be transferred to the first syringe 720 at a flow rate ranging from about 0.2 mL per second to about 1 mL per second. In some embodiments, the second substance can be transferred to the first syringe 720 at a flow rate of about 0.5 mL per second.

In some embodiments, after the second substance is transferred from the second syringe 730 to the first syringe 720 to combine with the remaining portion of the first substance to form a third substance, the third substance can be allowed to remain in the first syringe 720 for a wait period having any suitable duration. For example, in some embodiments, the wait period may be at least about 2 minutes. In some embodiments, the wait period may be between about 2 minutes and about 4 minutes. Allowing the third substance to remain in the first syringe 720 for the wait period prior to infusing the third substance into the patient's vasculature can reduce the discomfort of the patient during infusion (e.g., due to nitric oxide in the third substance being absorbed into blood cells during the wait period). In some embodiments, during the wait period, the fluid line from the assembly 740 to the patient (e.g., the first tube 702) can be flushed. For example, a fourth syringe (not shown) containing saline can be fluidically coupled to the third valve 770. The third valve 770 can be transitioned to a third configuration in which the third valve 770 allows fluid communication between the first tube 702 and the fourth syringe but fluidically isolates the fourth syringe from the interior region of the first valve 750. The saline can then be delivered from the fourth syringe, through the first tube 702, through the access tube 716, through the patient access port 712, and into the patient's vasculature such that blood can be flushed from the fluid path. The third valve 770 can then be transitioned to fluidically isolate the fourth syringe and/or the first tube 702 from the first valve 750 (e.g., to a closed position). The fourth syringe can then be detached from the third valve 770.

Figure 30:
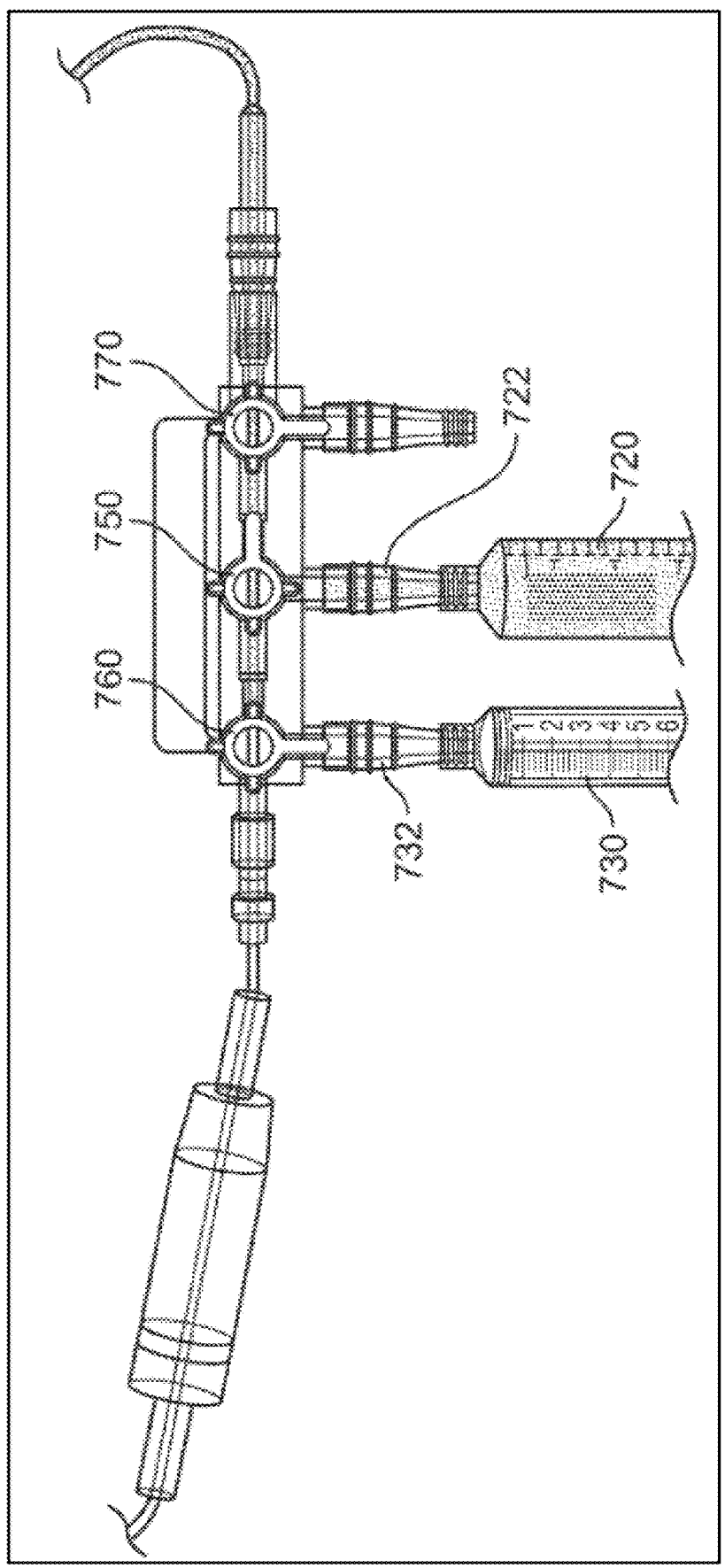
FIG. 30 is a top view of a portion of the mixing assembly of FIG. 21 in an infusion configuration.

As shown in FIG. 30, the assembly 740 can then be transitioned to the third assembly configuration such that the first syringe 720 is in fluid communication with the patient access subassembly 710 via the first valve 750, the second valve 760, the second tube 704, the filter 790, and the third tube 704B. For example, the first valve 750 can remain in the second configuration of the first valve 750 and the second valve 760 can be manipulated or toggled such that the second valve 760 is in the second configuration of the second valve 760 (e.g., the lever of the second valve 760 can be rotated to point toward the second syringe 720 such that the second syringe 720 is fluidically isolated from the interior region of the second valve 760). Additionally, the first selective flow inhibitor 718 and the third selective flow inhibitor 708 can each be transitioned to an open configuration such that fluid can flow through the access tube 716 and the third tube 704B, respectively.

Figure 31:
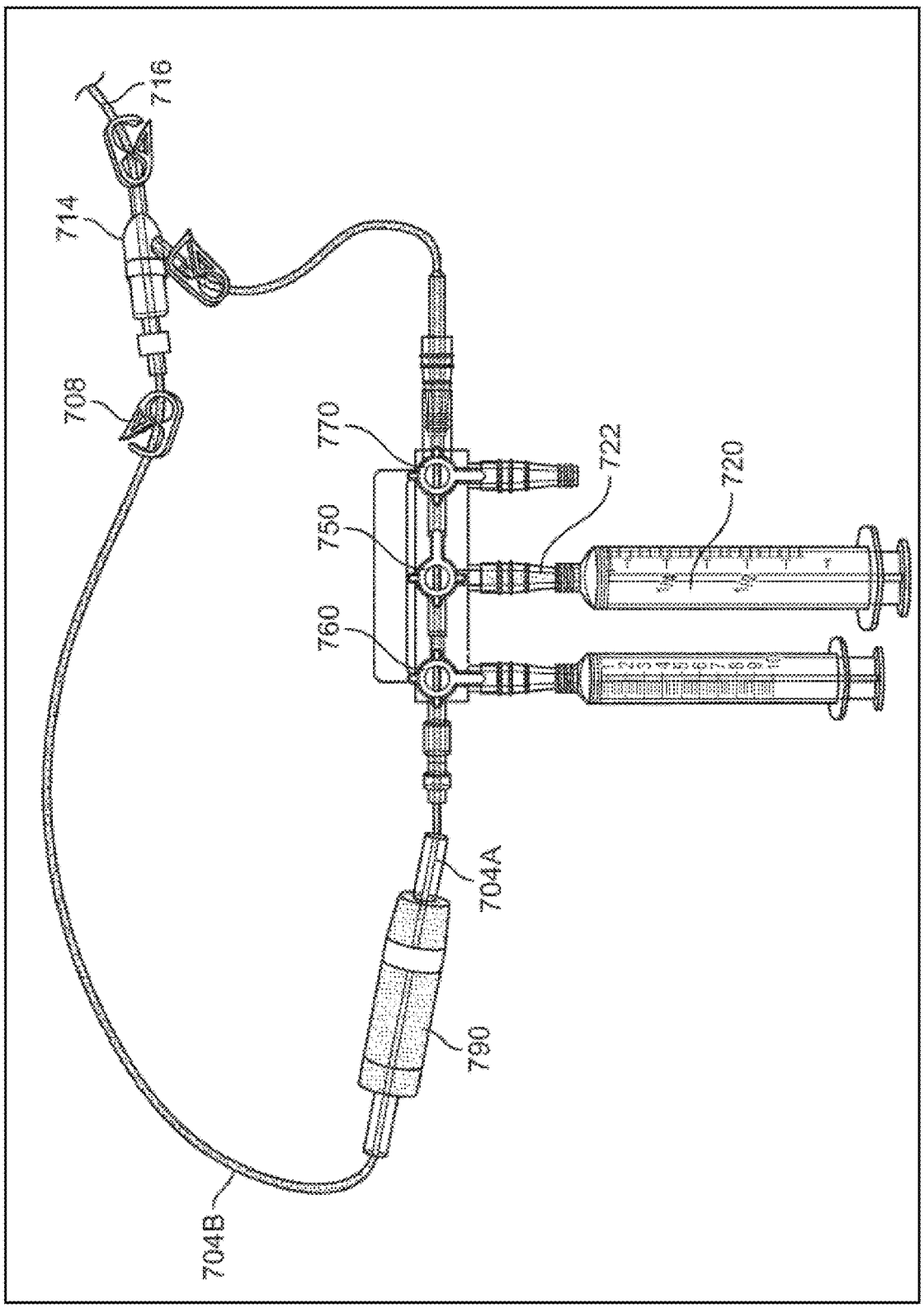
FIG. 31 is a top view of the system of FIG. 20 during an infusion stage of an administration procedure.

As shown in FIG. 31, the third substance can then be transferred from the first syringe 720 to the patient's vasculature system via the first valve 750, the second valve 760, the second tube 704A, the filter 790, the third tube 704B, and the patient access subassembly 710. In some embodiments, the third substance can be transferred from the first syringe 720 to the patient access subassembly 710 at a rate sufficiently low to avoid stress to red blood cells within the third substance. For example, the third substance can be transferred to the patient at a flow rate ranging from about 0.2 mL per second to about 1 mL per second. In some embodiments, the third substance can be transferred to the patient at a flow rate of about 0.5 mL per second.

Figure 32:
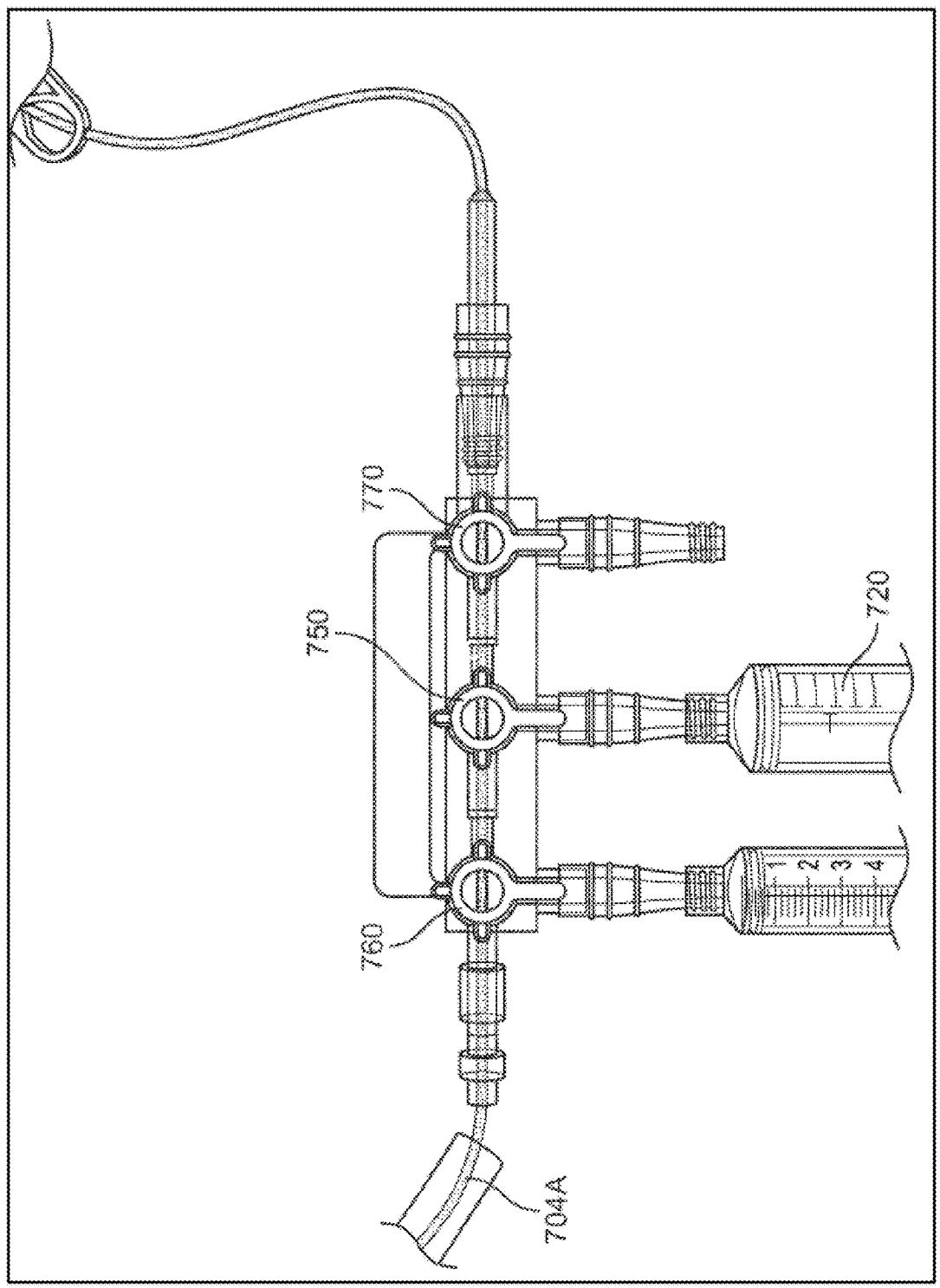
FIG. 32 is a top view of a portion of the mixing assembly of FIG. 21 in a pre-flush configuration.

As shown in FIG. 32, after transferring the third substance to the patient's vasculature, the first valve 750 can be rotated such that the lever points toward the first syringe 720 and the first syringe 720 is fluidically isolated from the interior region of the second valve 760 and the interior region of the third valve 770.

Figure 33:
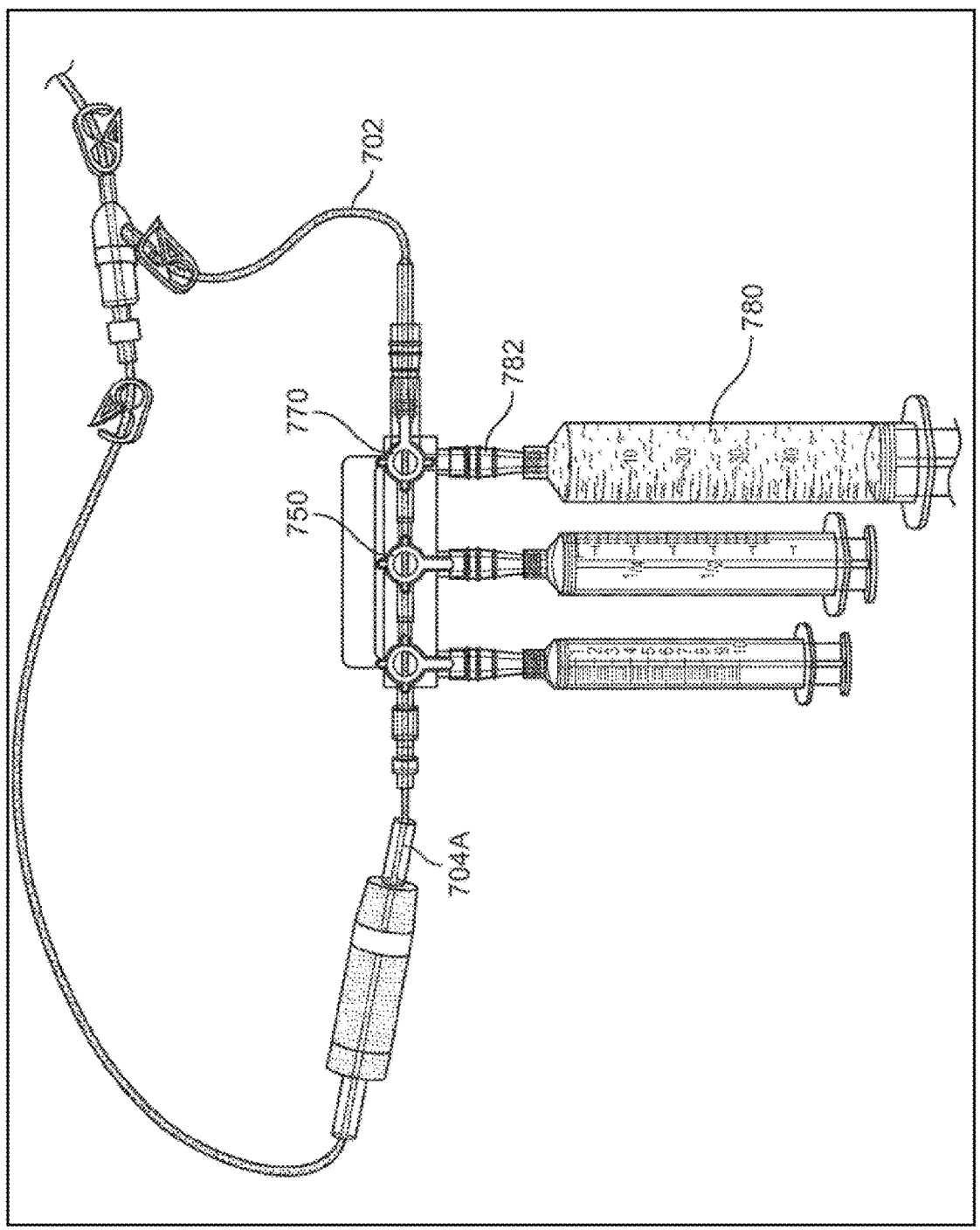
FIG. 33 is a top view of the system of FIG. 20 with a syringe containing a saline solution coupled to the mixing assembly.

As shown in FIG. 33, the third syringe 780 can be coupled to the third valve 770 via the third connector 782. The assembly 740 can then be transitioned to the fourth assembly configuration such that the third syringe 780 is in fluid communication with the patient access subassembly 710 via the third valve 770, the first valve 750, the second valve 760, and the second tube 704A. For example, with the first valve 750 in the third configuration of the first valve 750 and the second valve 760 in the second configuration of the second valve 760, the third valve 770 can be manipulated or toggled such that the third valve 770 is in the second configuration of the third valve 770 (e.g., the lever of the third valve 770 is directed toward the first tube 702 such that the first valve 750 and the third syringe 780 are fluidically isolated from the first tube 702).

Figure 34:
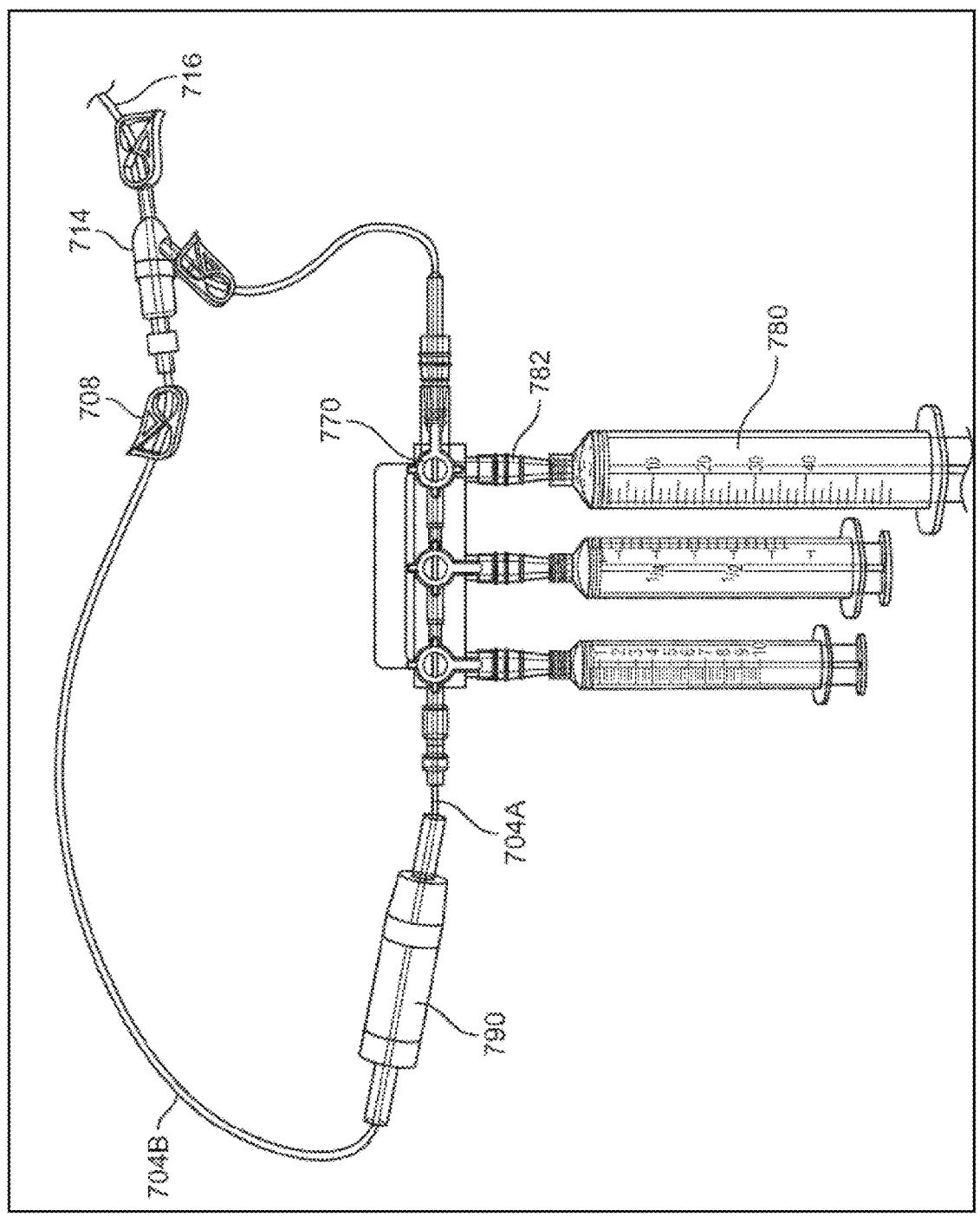
FIG. 34 is a top view of the system of FIG. 20 after being flushed with a saline solution.

As shown in FIG. 34, the contents of the third fluid reservoir 780 (i.e., saline) can then be transferred to the patient access subassembly 710 via the third valve 770, the first valve 750, the second valve 760, the second tube 704A, the filter 790, and the third tube 704B such that the saline flushes out the fluid flow path of the third substance. In some embodiments, the contents of the third fluid reservoir 780 can be delivered at a rate of about 0.5 mL/s to the patient access subassembly 710 via the third valve 770, the first valve 750, the second valve 760, the second tube 704A, the filter 790, and the third tube 704B. In some embodiments, an initial portion of the contents of the third fluid reservoir 780 can be delivered at a rate of 0.5 mL/s and the remaining portion of the contents of the third fluid reservoir 780 can be delivered at a rate higher than 0.5 mL/s. For example, the first 10-20 mL of the contents of the third fluid reservoir 780 can be delivered at a rate of 0.5 mL/s and the remaining contents of the third fluid reservoir 780 can be delivered at a rate higher than 0.5 mL/s. The system 700 can then be detached from the patient.

In some embodiments, rather than providing portions of the system 700 separately, the system 700 can be packaged in a sterile pouch or container in an assembled configuration. The second syringe 730 can be provided separately (e.g., also within the sterile pouch or separately from the sterile pouch). A practitioner, such as an infusion nurse, can open the sterile pouch at a patient's bedside, prime the system 700 with saline, and couple the second syringe 730 to the assembly 740 (e.g., prior to operation of the system 700).

Although not shown, the system 700 (and any of the embodiments described herein) can optionally include a partial deoxygenation device (not shown). For example, in some embodiments, the combination of blood with a medicament such as 2-Bromo-1-(3,3-dinitroazetidin-1-yl)ethanone or another hemoglobin-binding compound can promote an increase in autoxidation-producing reactive oxygen species (ROS) that are not completely neutralized by other antioxidants combined with the blood using the system 700. Overoxidized red cells in the blood may lead to premature removal by the reticuloendothelial system (RES) in the body or hemolysis in the system 700, both of which are undesirable. Thus, to avoid these undesirable outcomes, treated blood (e.g., blood mixed with 2-Bromo-1-(3,3-dinitroazetidin-1-yl)ethanone) can be transferred through the partial deoxygenation device (e.g., in through an inlet of the partial deoxygenation device and out through an outlet of the partial deoxygenation device that can be the same or different from the inlet). The partial deoxygenation device can include a bag configured to receive treated blood. The bag can be coupled to the system 700 between, for example, the valve assembly 740 and the connector 714 of the patient access subassembly 710 such that blood that has been mixed with the contents of the second reservoir 730 can travel through the bag prior to being infused into the patient (e.g., pushed into the bag and then squeezed out of the bag to continue toward the patient). For example, the bag can be coupled between the filter 790 and the third tube 704B or between the third tube 704B and the patient access subassembly 710. In some embodiments, the bag can be pre-filled with nitrogen.

In some embodiments, the bag can include an oxygen impermeable outer layer, an oxygen permeable inner layer, and an oxygen scrubber. The inner layer can be disposed inside the outer layer and can define a reservoir. The oxygen scrubber can be disposed between the inner layer and the outer layer and can include any suitable material capable of absorbing oxygen (e.g., oxygen sorbents such as iron powders with or without a catalyst such as palladium). In some embodiments, the bag (e.g., the reservoir defined by the inner layer) can be pre-filled with an analgesic and/or an anesthetic drug prior to use of the system 700 such that patient pain and/or discomfort associated with infusion can be attenuated. The analgesic can include, for example, morphine, oxycodone, fentanyl, sufentanil, pethidine, and/or any other suitable analgesic. The anesthetic can include, for example, ropivacaine, lidocaine, bupivacaine, cloroprocaine, and/or any other suitable anesthetic. In some embodiments, rather than the bag being a partial deoxygenation device, the bag can define a reservoir pre-filled with an analgesic and/or an anesthetic drug to be mixed with the treated blood prior to reinfusion.

In some embodiments, each of the first valve 750, the second valve 760, and the third valve 770 can include a visible indicator representing the intended order of actuation of the valves and/or an instruction associated with the intended operation of the system 700. For example, each of the first valve 750, the second valve 760, and the third valve 770 can be formed by or include a different color or can be labeled with a different number (e.g., 1, 2, 3, etc.) or letter (e.g., A, B, C, etc.).

Figure 35:
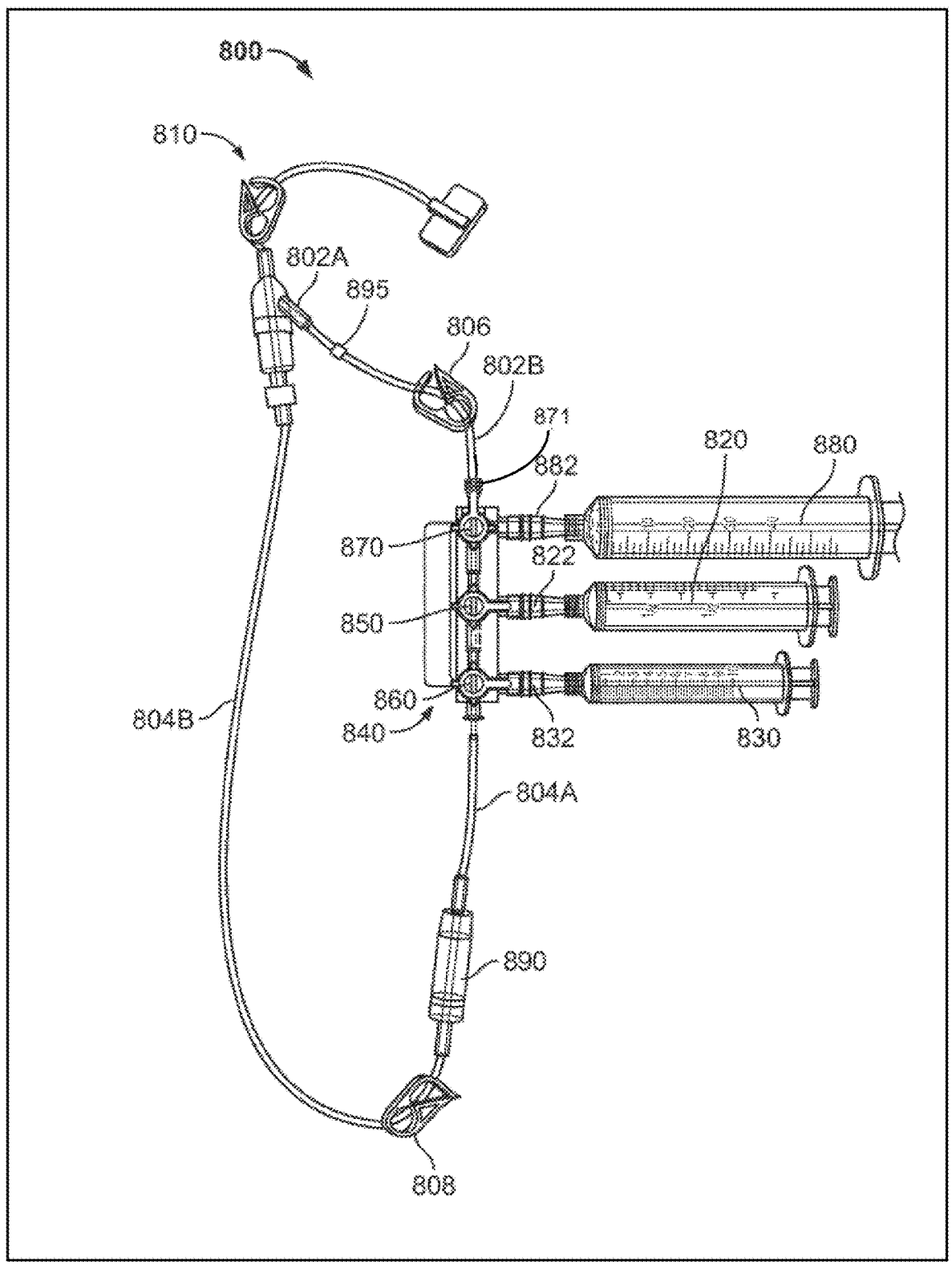
FIG. 35 is a top view of an example system, according to an embodiment.

In some embodiments, a system can include a white blood cell filter upstream of the valve assembly. For example, FIG. 35 is a top view of a system 800. The system 800 can be similar in structure and/or function to any of the systems described herein, such as the system 700. For example, each of the components of the system 800 can be the same or similar in structure and/or function to corresponding components of the system 700.

For example, the system 800 includes a patient access subassembly 810, a first syringe 820, a second syringe 830, a third syringe 880, and an assembly 840. The patient access subassembly 810, the first syringe 820, the second syringe 830, the third syringe 880, and the assembly 840 can be the same or similar in structure and/or function to the patient access subassembly 710, the first syringe 720, the second syringe 730, the third syringe 780, and the assembly 740. Further, the assembly 840 can include a first valve 850, a second valve 860, and a third valve 870. The first valve 850, the second valve 860, and the third valve 870 can be the same or similar to the first valve 750, the second valve 760, and the third valve 770. The system can also include a first connector 832, a second connector 822, and a third connector 882 that can be the same and/or similar to the first connector 732, the second connector 722, and the third connector 782. As shown in FIG. 35, the system 800 can also include a first tube 802 having a first tube portion 802A and a second tube portion 802B, a second tube 804A, a third tube 804B, and a filter 890, the second tube 804A coupled to the second valve 860 and the filter 890, the third tube 804B coupled to the patient access subassembly 810 and the filter 890.

As shown in FIG. 35, a white blood cell filter 895 is disposed between the first tube portion 802A of the first tube 802 and the second tube portion 802B of the first tube 802. The white blood cell filter 895 can filter white blood cells to prevent damage to red blood cells, which, in some embodiments, act as carriers for the in vivo delivery of medicament to the patient after the medicament is combined with the patient's blood ex vivo. Since white blood cells (also referred to as leukocytes) can elaborate or produce inflammatory molecules, the white blood cell filter 895 can be used to remove white blood cells from (e.g., leukoreduce) the fluid (e.g., blood) drawn from the patient via the patient access subassembly 810 by filtering out white blood cells to reduce potential oxidation and damage to the red blood cells. The white blood cell filter 895 can have any suitable pore size for filtering white blood cells from red blood cells For example, the pore size of the white blood cell filter 895 can range from 6-16 µm. Thus, white blood cells can be filtered from the flow of blood from the patient prior to being drawn into the first syringe 820 to prevent the white blood cells from oxidizing red blood cells.

Figure 36:
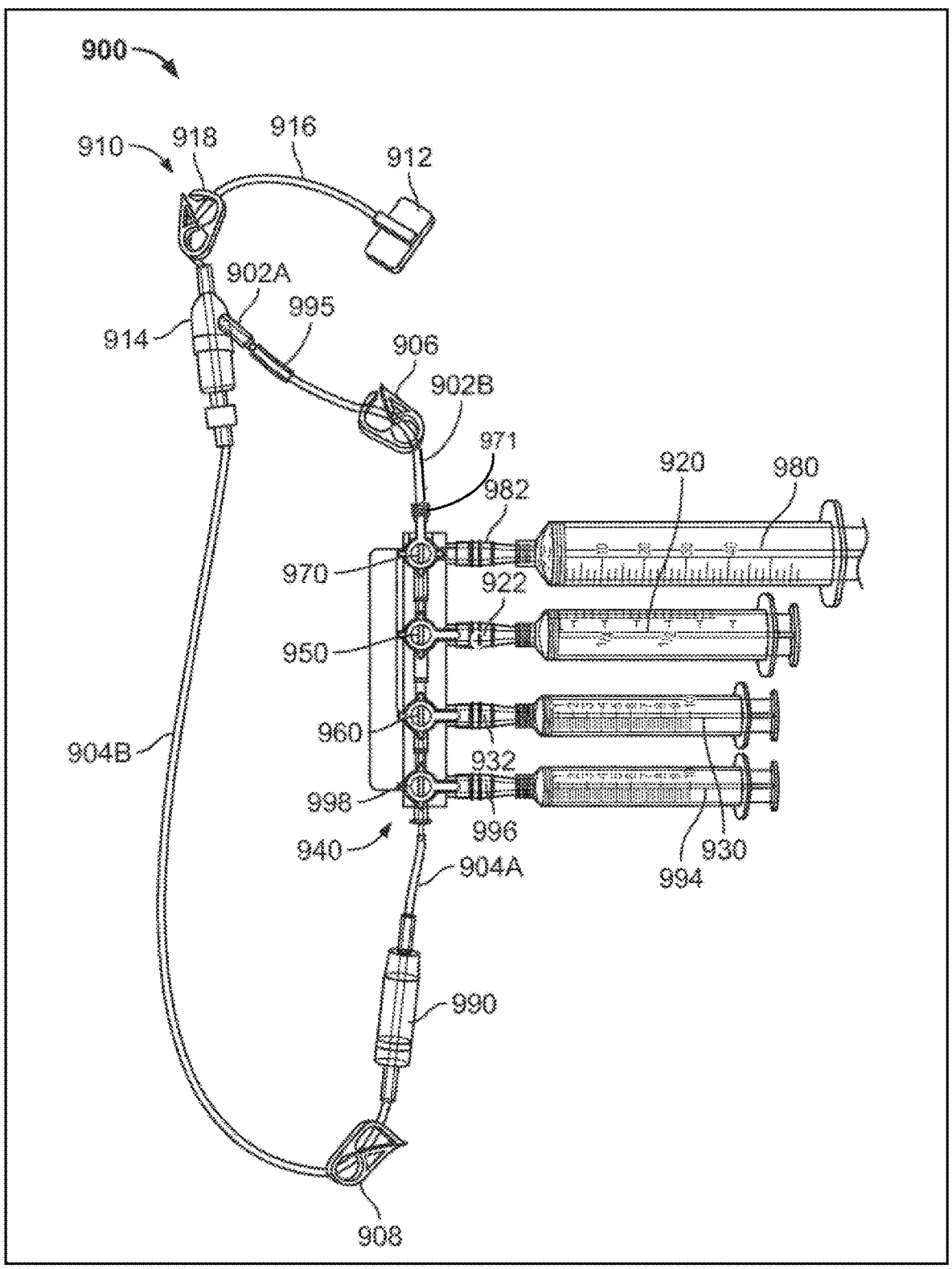
FIG. 36 is a top view of an example system, according to another embodiment.

In some embodiments, a fourth valve and a fourth syringe can be included in a mixing assembly. For example, FIG. 36 is a top view of a system 900. The system 900 can be similar in structure and/or function to any of the systems described herein, such as the system 700. For example, each of the components of the system 900 can be the same or similar in structure and/or function to corresponding components of the system 700.

For example, the system 900 includes a patient access subassembly 910, a first syringe 920, a second syringe 930, a third syringe 980, and an assembly 940. The patient access subassembly 910, the first syringe 920, the second syringe 930, the third syringe 980, and the assembly 940 can be the same or similar in structure and/or function to the patient access subassembly 710, the first syringe 720, the second syringe 730, the third syringe 780, and the assembly 740. Further, the assembly 940 can include a first valve 950, a second valve 960, and a third valve 970. The first valve 950, the second valve 960, and the third valve 970 can be the same or similar to the first valve 750, the second valve 760, and the third valve 770. The system can also include a first connector 932, a second connector 922, and a third connector 982 that can be the same and/or similar to the first connector 732, the second connector 722, and the third connector 782. As shown in FIG. 35, the system 900 can also include a first tube 902 having a first tube portion 902A and a second tube portion 902B, a second tube 904A, a third tube 904B, and a filter 990, the second tube 904A coupled to the assembly 940 and the filter 990, the third tube 904B coupled to the patient access subassembly 910 and the filter 990.

Similarly as described above with reference to FIG. 35, a white blood cell filter 995 can be optionally disposed between the first tube portion 902A of the first tube 902 and the second tube portion 902B of the first tube 902. Thus, white blood cells can be filtered from the flow of blood from the patient prior to being drawn into the first syringe 920 to prevent the white blood cells from oxidizing red blood cells.

Further, the system 900 can include one or more additional sets of one or more valves, one or more connectors, and/or one or more syringes. As shown in FIG. 36, the assembly 940 includes a fourth valve 998 coupled to a fourth syringe 994 via a fourth connector 996. In some embodiments, the fourth syringe 994 can be prefilled with and/or contain an antioxidant, such as, for example, vitamin C or N-acetylcysteine. Although the fourth valve 998 is shown as being coupled between the second valve 960 and the second tube 940A, in some embodiments, the fourth valve 998 can be disposed in any suitable location relative to the other valves, such as between the first valve 950 and the second valve 960. The fourth valve 998 and the fourth syringe 994 can be configured to draw a portion of the first substance or blood from the first syringe 920 into the fourth syringe 994 to combine with the antioxidant in the fourth syringe 994 and then to return the combination to the first syringe 920 similarly as described with respect to the second valve 760 and second syringe 730 above.

Figure 37:
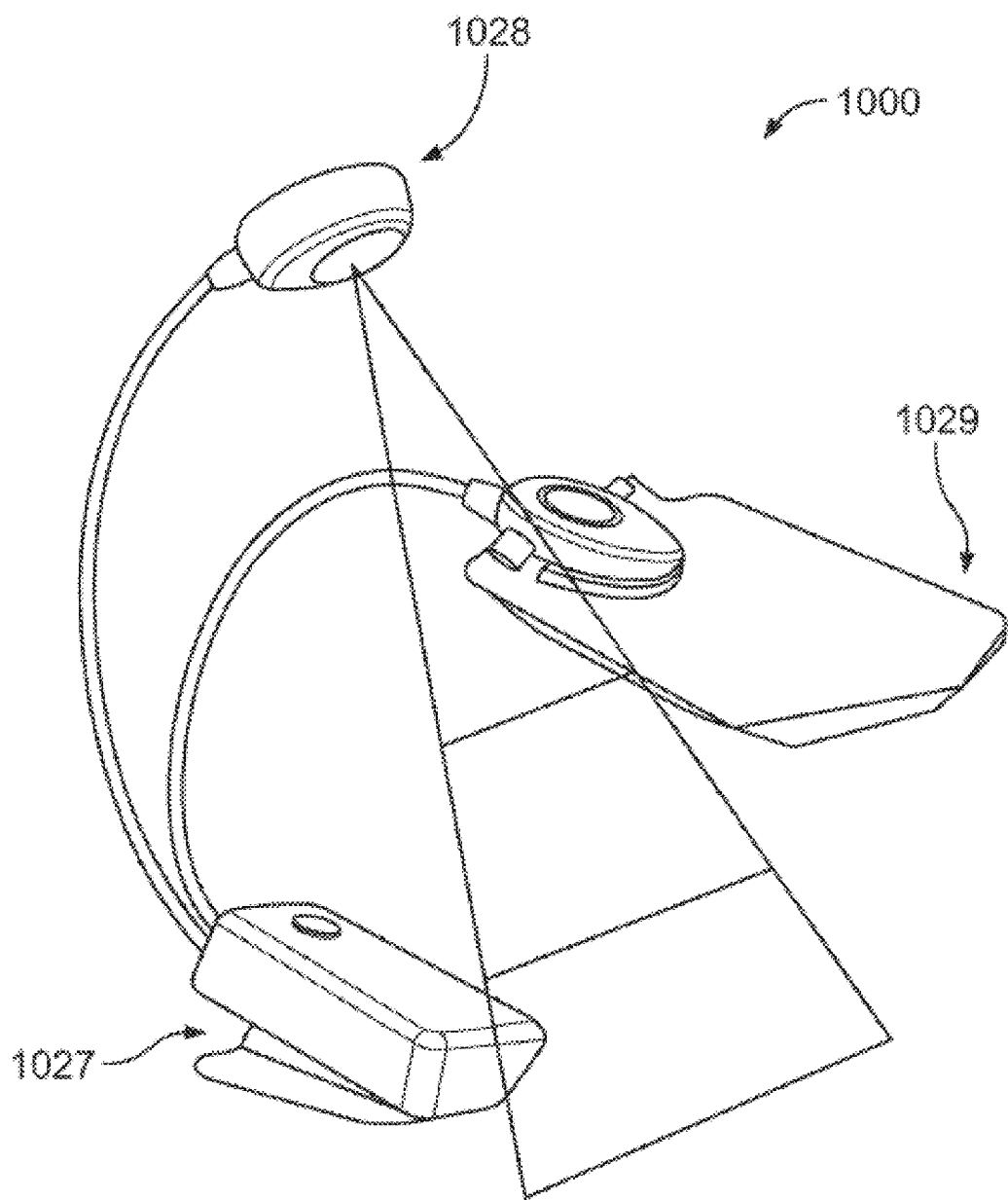
FIG. 37 is a perspective view of a light assembly, according to an embodiment.

In some embodiments, one or more tubes used in any of the systems described herein can be tinted a color (e.g., green) such that clots can be more easily visualized by a user. Additionally, in some embodiments, a system, such as any of the systems described herein, can include a light assembly. In some embodiments multiple light sources, such as LEDs, can be placed near or adjacent the tubes of any of the systems described herein such that clots can be more easily visualized. For example, the multiple light sources can provide green light such that the clots appear as black. For example, FIG. 37 is an illustration of a light assembly 1000. The light assembly 1000 can be positioned near a portion of tubing of any of the systems described herein to assist in visualizing blood clots. The light assembly 1000 can project green light from a light source 1028 so that the blood clots appear to be black in color. In some embodiments, the light assembly can include a magnifying glass 1029 to assist the user in looking more closely at the contents of portions of tubing. Additionally, the light assembly 1000 can include a clip 1027 such that the light assembly 1000 can be securely attached to an object associated with an infusion system, such as, for example, a fluid bag pole.

In some embodiments, a kit can include a light assembly, such as the light assembly 1000 shown and described with respect to FIG. 37, and any of the systems disclosed herein. For example, a kit can include the light assembly 1000 and the system 700 shown and described above.

Figure 38:
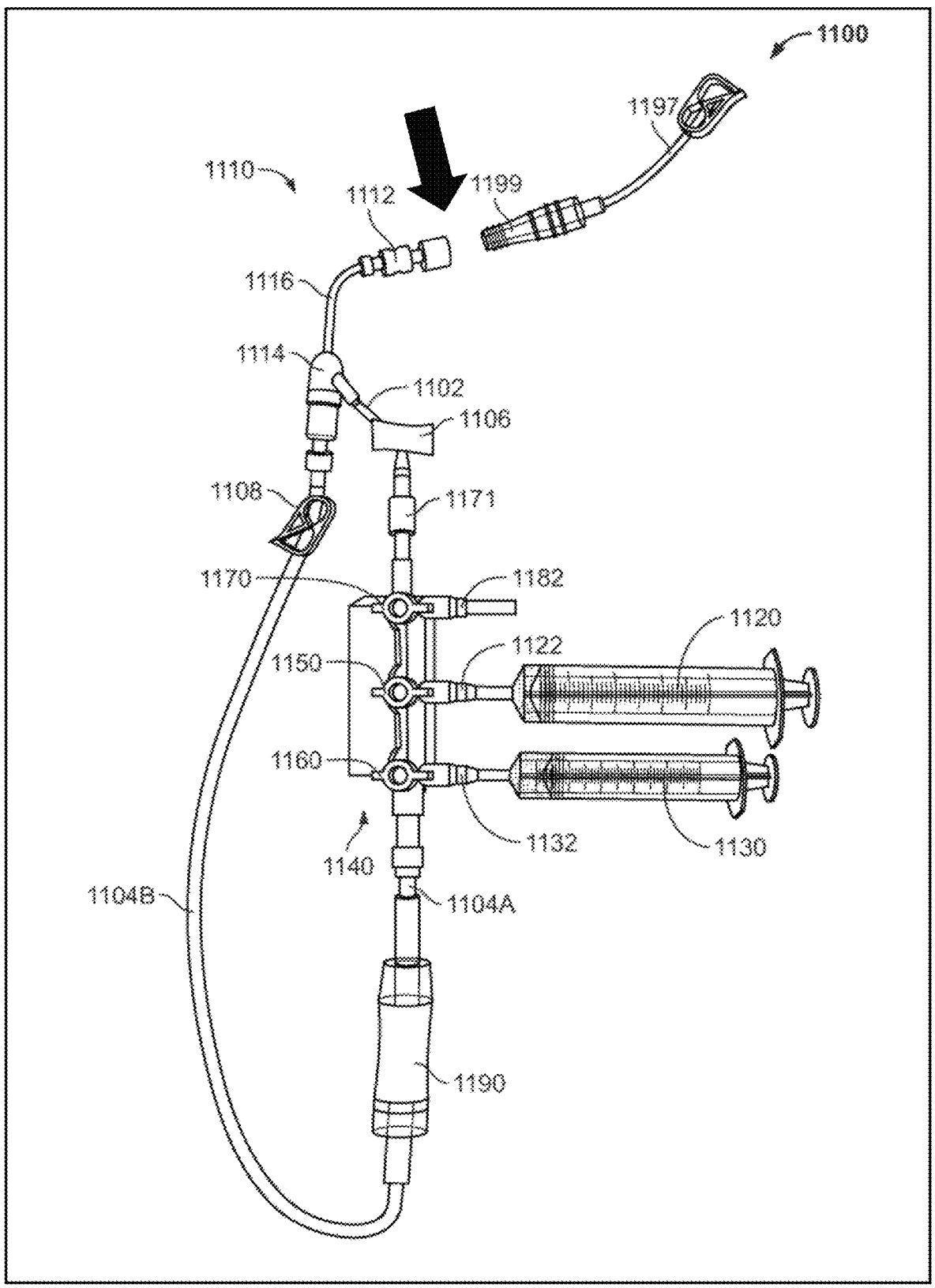
FIG. 38 is a top view of an example system, according to an embodiment.

In some embodiments, as described above, a system can include a patient access subassembly having a connector configured to be coupled to a connector of a patient's intravascular tubing. The intravascular tubing may be fluidically coupled to a patient's vascular system prior to attachment to the system. For example, the intravascular tubing may be a peripherally inserted central catheter (PICC) and the connector of the intravascular tubing may be any suitable standard connector. For example, FIG. 38 is a top view of a system 1100. The system 1100 can be similar in structure and/or function to any of the systems described herein, such as the system 700. For example, each of the components of the system 1100 can be the same or similar in structure and/or function to corresponding components of the system 700.

For example, the system 1100 includes a patient access subassembly 1110, a first syringe 1120, a second syringe 1130, a third syringe (not shown), and an assembly 1140. The patient access subassembly 1110, the first syringe 1120, the second syringe 1130, the third syringe, and the assembly 1140 can be the same or similar in structure and/or function to the patient access subassembly 710, the first syringe 720, the second syringe 730, the third syringe 780, and the assembly 740. Further, the assembly 1140 can include a first valve 1150, a second valve 1160, and a third valve 1170. The first valve 1150, the second valve 1160, and the third valve 1170 can be the same or similar to the first valve 750, the second valve 760, and the third valve 770. The system can also include a first connector 1132, a second connector 1122, and a third connector 1182 that can be the same and/or similar to the first connector 732, the second connector 722, and the third connector 782. As shown in FIG. 35, the system 1100 can also include a first tube 1102 included in the patient access subassembly 1110, a second tube 1104A, a third tube 1104B, and a filter 1190, the second tube 1104A coupled to the second valve 1160 and the filter 1190, the third tube 1104B coupled to the patient access subassembly 1110 and the filter 1190.

FIG. 38 is a top view of the patient access subassembly 1110 of the system 1100. As shown, the patient access subassembly 1110 can be provided independent from the remainder of the system 1100. The patient access subassembly 1110 can include a patient access port 1112, access tubing 1116, and a connector 1114. The patient access port 1112 can include a connector configured to couple the access tubing 1116 to intravenous tubing previously coupled to the patient's vasculature system (e.g., a PICC line). For example, as shown in FIG. 38, the patient access port 1112 can be coupled to a connector 1199 disposed on the end of intravenous tubing 1197 such that the system 1100 can be in fluid communication with the intravenous tubing 1197. The connector 1114 of the patient access subassembly 1110 can be coupled to the third valve 1170 via the first tube 1102 such that the patient access subassembly 1110 can be in fluid communication with the third valve 1170 via a first fluid route. The connector 1114 can be coupled to the second valve 1160 via a second fluid route including the second tube 1104A, the third tube 1104B, and the filter 1190 such that the patient access subassembly 1110 can be in fluid communication with the second valve 1160 via the second fluid route.

Figure 39:
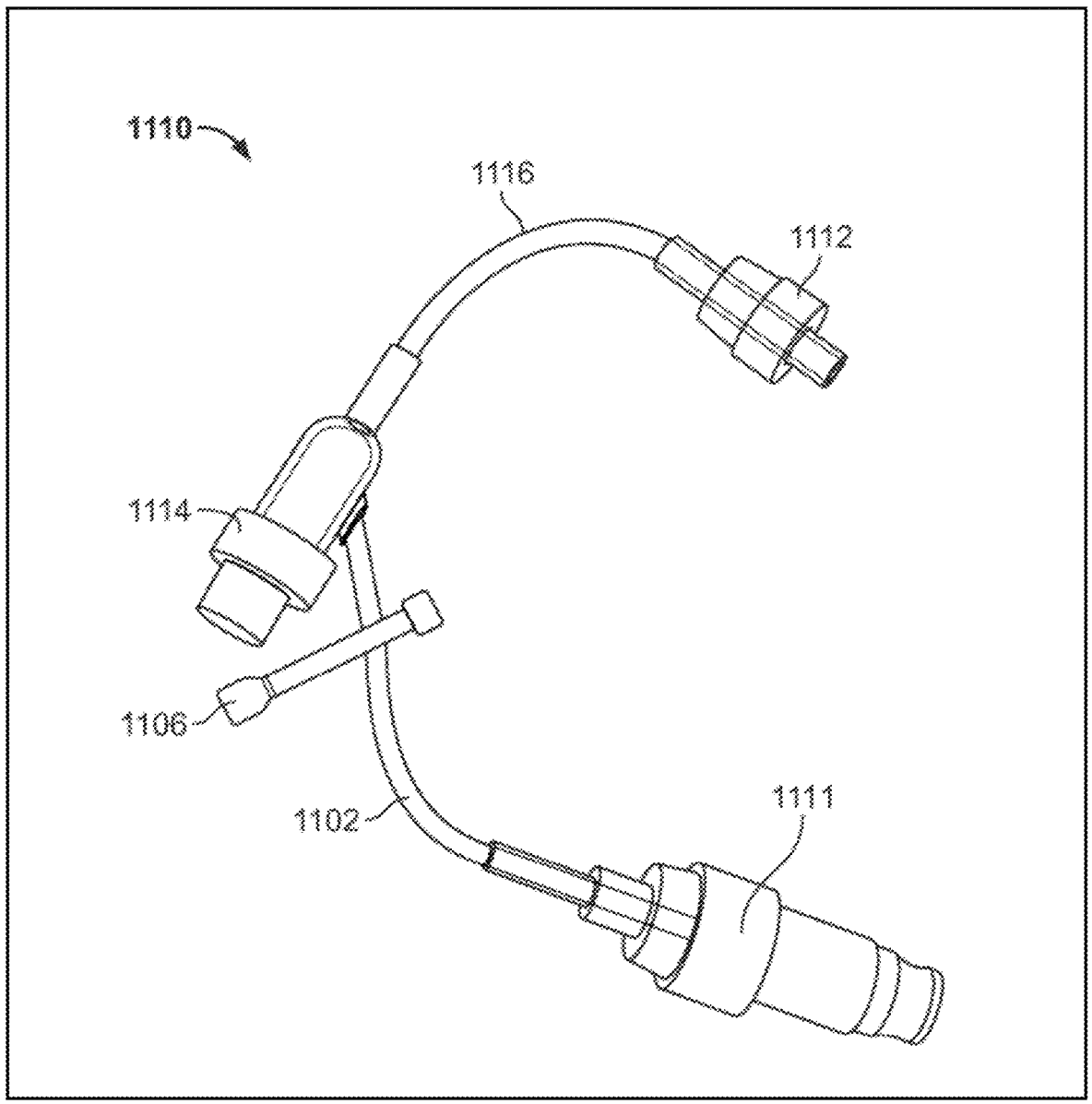
FIG. 39 is a top view of a patient access subassembly of the system of FIG. 38.

Thus, the system 1100 can function as a closed loop system in which fluid can flow away from the patient access subassembly 1110 via the first tube 1102 and return to the patient access subassembly 1110 via the second tube 1104A, the filter 1190, and the third tube 1104B. The patient access subassembly 1110 can be provided with an end cap 1111 on the end of the first tube 1102 opposite from the connector 1114. The system 1100 can include any suitable number of selective flow inhibitors coupled to tubing of the system 1100 such that the flow through the tubing can be temporarily inhibited. For example, a selective flow inhibitor 1106 can be disposed on the first tube 1102 as shown in FIG. 39. Each of the selective flow inhibitors (e.g., the selective flow inhibitor 706), can be, for example, tubing clamps or roller clamps.

Figure 40:
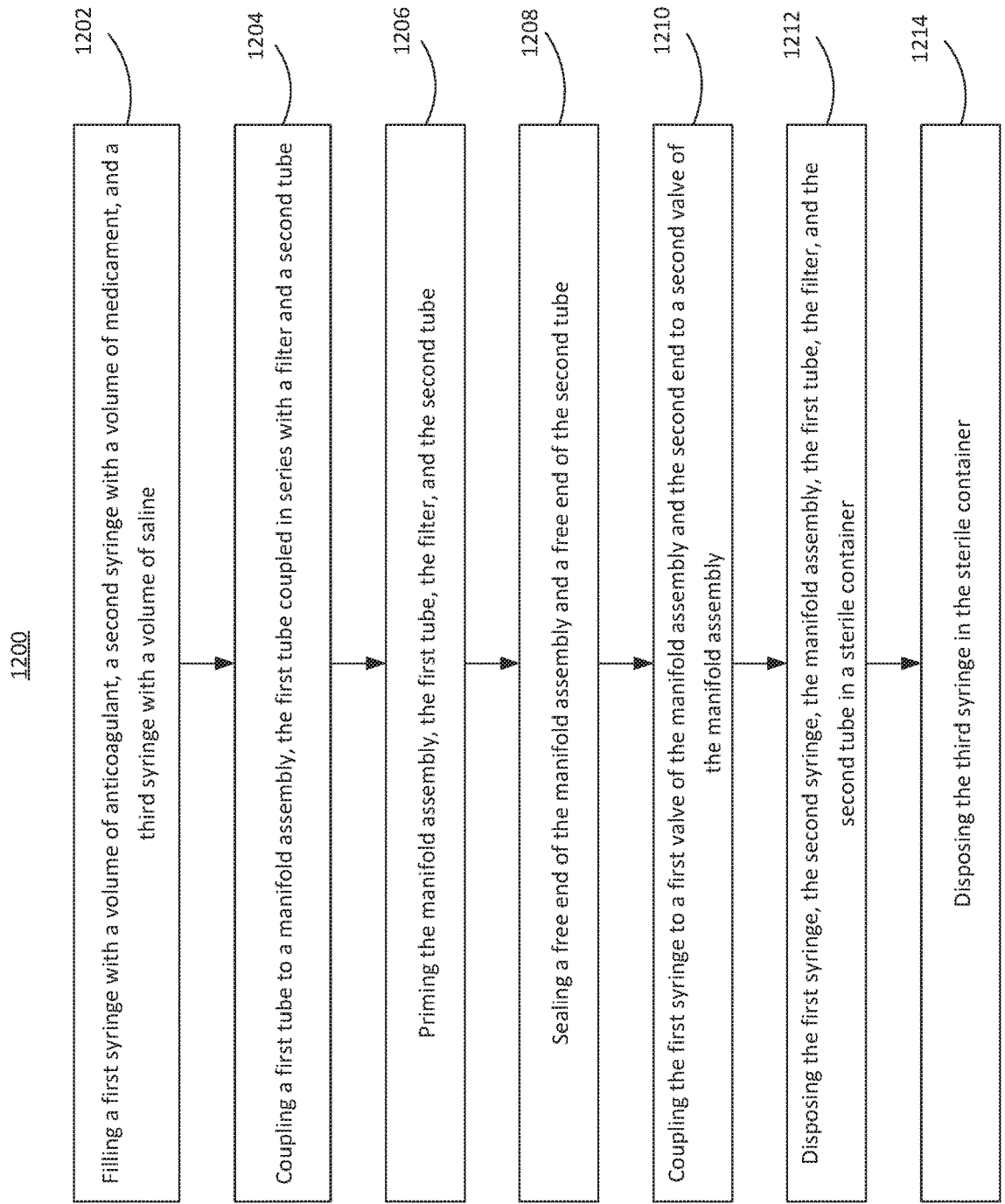
FIG. 40 is a flow chart of a method, according to an embodiment.

In some embodiments, as shown in FIG. 40, a system, such as any of the systems described herein, can be prepared for assembly and/or partially assembled at a pharmacy prior to delivery to a user. For example, a user (e.g., a clinician or pharmacist) may open one or more pouches under a laminar flow hood or in a similar sterile environment. The components of at least a portion of a system, such as a mixing assembly, can be distributed amongst the one or more pouches. The mixing assembly can be, for example, the same or similar as the mixing assembly 707 described above with respect to FIG. 21. In some embodiments, a first pouch may include a first tube (e.g., second tube 704A) coupled in series to a filter (e.g., filter 790) coupled in series to a second tube (e.g., third tube 704B) and a second pouch may include syringes, a valve manifold assembly (e.g., assembly 740), and/or injection caps (also referred to as connectors). The components of the mixing assembly can be individually wrapped within the second pouch. For example, the second pouch can include a first syringe (e.g., first syringe 720), a second syringe (e.g., second syringe 730), and a third syringe (e.g., third syringe 780). For example, the first syringe can be a 20 mL syringe, the second syringe can be a 10 mL syringe, and the third syringe can be a 60 mL syringe. Each of the syringes can be empty. The connectors can include a first connector (e.g., first connector 722), a second connector (e.g., second connector 732), and a third connector (e.g., third connector 782).

As shown at 1202, each of the syringes may be prepared by being filled with an appropriate substance. The first syringe can be filled with a volume of anticoagulant such as any of the anticoagulants described herein (e.g., 1.5 mL of ACD-A). The second syringe can be filled with a volume of medicament such as any of the medicaments described herein (e.g., 2 mL of volume for a 4 mg dose of 2-Bromo-1-(3,3-dinitroazetidin-1-yl)ethanone). The third syringe can be filled with saline (e.g., 60 mL of saline). Each of the first syringe, the second syringe, and third syringe can then be capped and labeled.

As shown at 1204, the first tube can then be coupled to the manifold assembly. In some embodiments, one end of the manifold assembly (e.g., the end including a third valve such as third valve 770) can have a male connector and the opposite end of the manifold assembly (e.g., the end including the second valve such as second valve 760) can have a female connector. The free end of the first tube (e.g., the end opposite the end coupled to the filter) can have a male connector such that the free end of the first tube is configured to be coupled to the side of the manifold assembly having a female connector.

The valves of the manifold assembly can each be disposed in a configuration allowing fluid flow through the manifold assembly from the first end to the second end (e.g., toggles of each of the valves can be directed away from syringe ports of the valves). The first connector, the second connector, and the third connector can be coupled to each of the first valve, the second valve, and the third valve, respectively.

As shown at 1206, the mixing assembly can then be primed by flushing the manifold assembly, first tube, filter, and second tube. For example, a saline syringe can be coupled to the available end of the manifold assembly (opposite the end of the manifold assembly coupled to the first tube). In some embodiments, the saline syringe can be a pre-filled fourth syringe. In some embodiments, rather than using a fourth syringe for priming, the first syringe can be filled with saline (e.g., 20 mL of saline) and then used to deliver saline to the mixing assembly prior to being filled with anticoagulant. In some embodiments, the syringe used to deliver the priming saline can be coupled to the manifold assembly via another suitable connector.

After connecting a syringe containing saline to the end of the manifold assembly, the saline can be delivered from the syringe through a fluid line including a chamber of the manifold assembly (e.g., defined in part by the interior chambers of the valves of the manifold assembly), the first tube, the filter, and the second tube such that air is pushed out of an open end of the second tube. In some embodiments, a first portion of the saline (e.g., 10 mL) may be pushed through the fluid line and then the filter may be engaged (e.g., tapped or shaken) to encourage the release of any residual air from the filter. The remainder of the saline (e.g., the remaining 10 mL) may then be delivered through the fluid line (e.g., from the same syringe as the first portion of the saline or from a second saline syringe attached in place of the initial saline syringe). Having delivered the priming saline, the saline syringe can be decoupled from the manifold assembly. As shown at 1208, the open end of the manifold assembly and the open end of the second tube can both be sealed (e.g., capped). Additionally, a selective flow inhibitor (e.g., third selective flow inhibitor 708) can be coupled to the second tube and closed.

The valves of the manifold assembly can be transitioned such that the syringe ports of the valves are fluidically isolated from one another and the first tube (e.g., the lever of each valve can be rotated 180 degrees to be directed toward the syringe ports). As shown at 1210, the first syringe can be coupled to the first valve and the second syringe can be coupled to the second valve. The syringes can be coupled to the first valve and the second valve such that gradations on the syringe are visible to the user during operation of the system (e.g., facing upward relative to a patient surface or a bottom of the manifold assembly (e.g., the side opposite the side including valve levers). As shown at 1212, the mixing assembly (e.g., the first syringe, second syringe, manifold assembly, first tube, filter, and second tube) can be disposed in a sterile container (e.g., bag or pouch) in an assembled configuration. As shown at 1214, the third syringe can be disposed in the sterile container decoupled from the manifold assembly. The mixing assembly can then be delivered as a sterile kit to another user, such as a nurse, doctor, or clinician for connection to a patient's vasculature via a patient access subassembly.

Although not shown, in some embodiments, rather than including a first fluid line from the patient access subassembly to the valve assembly and a separate second fluid line from the valve assembly to the patient access subassembly, a system can include a single fluid line for transfer of fluid to and from the valve assembly. In some embodiments, one or more of the syringes can include a filter between the fluid reservoir of the syringe and the single fluid line to prevent unwanted particles from the syringe from entering the patient's vasculature. In some embodiments, for example, a system similar to system 700 can be configured such that fluid flows from a patient access subassembly similar to patient access subassembly 710 via a first tube similar to the first tube 702. The system can then be configured and used such that, after the mixing procedure is performed by a mixing assembly similar (e.g., a mixing assembly including assembly 740, the first syringe 720 and the second syringe 730), the combined blood and medicament substance can be return to the patient access subassembly via the first tube. In such systems, a filter can be included at the interface of one or more of the syringes and the assembly and/or along the fluid flow path through the first tube to filter, for example, sediment from the combined blood and medicament substance as the substance is returned to the patient via the patient access subassembly. A syringe including a saline solution can then be coupled to the assembly to flush the flow path similarly as described with respect to other systems herein.

In some embodiments, any of the systems described herein can include a timer. For example, the time can be a standard timer including a clip that can clip onto a portion of the system (e.g., an assembly or tubing line). In some embodiments, the timer can be used to ensure that the process of using the system does not exceed a predetermined time threshold (e.g., to reduce the risk of infection). In some embodiments, the predetermined time threshold can be, for example, four hours or less. In some embodiments, the predetermined time threshold can be determined based on standards set by, for example, the American Academy of Blood Banks (AABB). In some embodiments, when blood is drawn from the patient, the timer can be started. In some embodiments, the timer can be a count-down timer such that the timer activates an alarm or other indicator at or near the predetermined time threshold. In some embodiments, the time can be a count-up timer such that a user can monitor the time that has passed since the mixing and infusion procedure has begun. In some embodiments, the timer can be integrated into any of the systems described herein such that the timer can control the initiation or cessation of the process of drawing, treating, and infusing blood. For example, in some embodiments, the timer can control the opening and/or closing of one or more valves of a system such that, after a predetermined time threshold has passed since the timer has been started (e.g., a valve has been opened or the timer was manually started prior to blood draw), the timer causes one or more valves to close and infusion to cease.

In some embodiments, rather than drawing blood from a patient through a patient access subassembly, and into a first reservoir (e.g., via pulling on a plunger of a syringe defining the first reservoir), the patient's blood can be drawn and processed prior to being drawn into an assembly, such as any of the assemblies described herein. For example, the patient's blood can be drawn and processed prior to being combined with an anti-coagulant and/or a medicament (e.g., prior to being drawn into the first reservoir within the first syringe). Thus, rather than whole blood being combined with the anti-coagulant and/or medicament, individual cells (e.g., platelets, red blood cells, white blood cells, and/or tumor cells) can be isolated from other components of the patient's blood and combined with the anti-coagulant and/or medicament. Further, plasmapheresis (i.e., the separation of plasma from blood cells) and/or leukapheresis (i.e., the separation of white blood cells from other components of a blood sample) can be performed on the blood drawn from the patient prior to combining the resulting plasma or white blood cells, respectively, with the anti-coagulant and/or medicament. In some embodiments, a buffy coat (e.g., a concentrated leukocyte suspension) can be separated from the drawn blood and then combined with the anti-coagulant and/or medicament. For example, the patient's blood can be separated via a centrifuge such that only a portion of the patient's blood is combined with the anti-coagulant, combined with the medicament, and then returned to the patient.

For example, in some embodiments, blood can be drawn from a patient (e.g., via a syringe and/or via any of the patient access subassemblies described herein). The blood can then be separated into component blood parts via any standard procedure, such as via a centrifuge. One or more components of the blood (e.g., platelets, red blood cells, white blood cells, plasma and/or tumor cells) can then be drawn into a first syringe of any of the systems described herein (e.g., the system 700) and combined with the anti-coagulant to form a first substance. For example, the component of the blood can be transferred from the centrifuge to a fluid bag or syringe, and then transferred to the first syringe. The remainder of the mixing and infusion procedure can then be performed via any of the methods described herein and/or using any of the systems described herein. For example, a portion of the first substance can then be transferred to a second syringe and combined with a medicament in the second syringe to form a second substance. The second substance can then be transferred to the first syringe and combined with the remainder of the first substance to form a third substance. The third substance can then be delivered to the patient. A third syringe can then be used to deliver, for example, saline or Ringer's lactate solution, to the patient via the same fluid route as the third substance was delivered.

In some embodiments, a closed system transfer device (CSTD) can be used in place of any of the connectors described herein. For example, a CSTD can be used in place of any of the needleless connectors described herein. The CSTD can be, for example, a CSTD manufactured by Equashield®, PhaSeal®, Chemoclave®, OnGuard®, or any other suitable CSTD.

Figure 41:
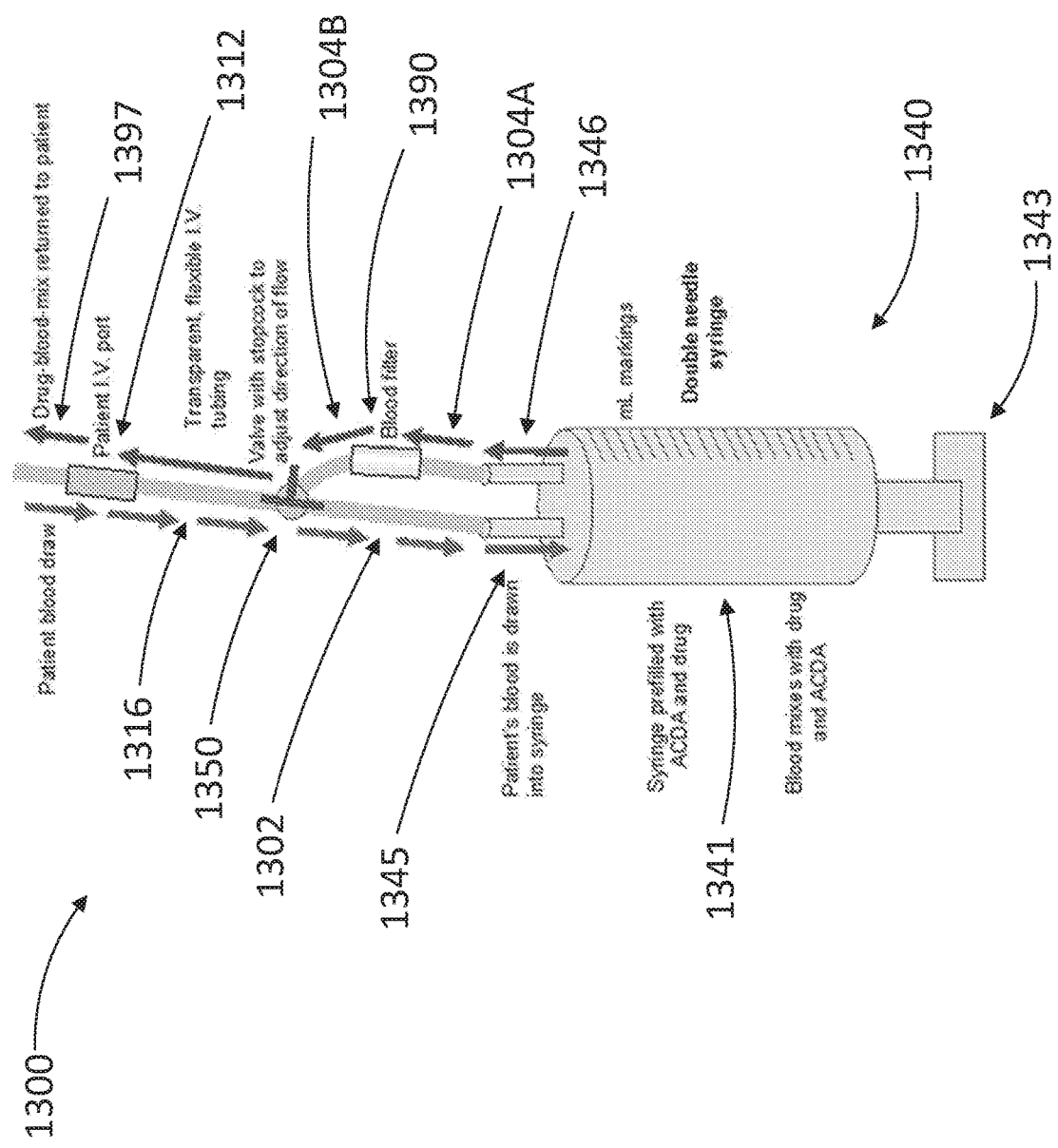
FIG. 41 is a schematic illustration of an example system, according to an embodiment.

In some embodiments, a system can include a double needle syringe. For example, FIG. 41 is a schematic illustration of a system 1300. The system 1300 includes a syringe 1340 (also referred to herein as a "double needle syringe"), a valve 1350, a patient intravenous port 1312 (also referred to herein as a "patient access port"), and a blood filter 1390. The blood filter 1390 can be the same or similar in structure and/or function to any of the blood filters described herein.

The syringe 1340 includes a barrel 1341 and a plunger 1343. The barrel 1341 and the plunger 1343 define a reservoir. The barrel 1341 can be transparent and can include indicator markings such that the volume of the reservoir can be visually observed by an operator of the system 1300. The syringe 1340 also includes a fluid inlet 1345 and a fluid outlet 1346. The fluid inlet 1345 can be coupled to the valve 1350 via a first tube 1302. The fluid outlet 1346 can be coupled to the valve 1350 via a second tube 1304A, the blood filter 1390, and a third tube 1304B. The fluid inlet 1345 can have any suitable shape and/or include any suitable connection components such that the first tube 1302 can be coupled to the fluid inlet 1345 and be in fluidic communication with the reservoir of the syringe 1340. The fluid outlet 1346 can have any suitable shape and/or include any suitable connection components such that the second tube 1304A can be coupled to the fluid outlet 1346 and be in fluidic communication with the reservoir of the syringe 1340. The valve 1350 can be coupled to the patient intravenous port 1312 via a fourth tube 1316. The patient intravenous port 1312 can be coupled to the patient via intravenous tubing 1397. The first tube 1302, the second tube 1304A, the third tube 1304B, the fourth tube 1316, and/or the intravenous tubing 1397 can be transparent and flexible (e.g., standard intravenous tubing).

The patient intravenous port 1312 can be the same or similar in structure and/or function to any of the patient access ports described herein, such as, for example, the patient access port 1112. For example, the patient intravenous port 1312 can include a connector configured to fluidically couple the fourth tube 1316 to the intravenous tubing 1397. The intravenous tubing 1397 can be coupled to the patient's vasculature system (e.g., the intravenous tubing can be a PICC line) and can be coupled to the patient's vasculature system prior to being coupled to the fourth tubing 1316 via the patient intravenous port 1312. In some embodiments, the intravenous tubing 1397 can include a connector disposed on an end of the intravenous tubing 1397 that can be same or similar in structure and/or function to any of the connectors described herein, such as, for example, the connector 1199. The intravenous tubing 1397 can be coupled to the patient intravenous port 1312 via the connector.

The reservoir inside of the barrel 1341 can be prefilled (e.g., in a pharmacy under sterile conditions). The reservoir can be prefilled, for example, with a medicament and an anticoagulant. The medicament can include any of the medicaments described herein, such as, for example, 2-Bromo-1-(3,3-dinitroazetidin-1-yl)ethenone. The anticoagulant can be any of the anticoagulants described herein, such as, for example, ACD-A. The volume of the medicament disposed within the reservoir of the syringe 1340 can be any suitable volume, such as any of the volumes described herein (e.g., 2 mL). The volume of the anticoagulant disposed within the reservoir of the syringe 1340 can be any suitable volume, such as any of the volumes described herein (e.g., 1.5 mL). In some embodiments, the reservoir can be additionally or alternatively be prefilled with any suitable substance described herein.

The valve 1350 can be, for example, a three-way stopcock. The valve 1350 can be the same or similar in structure and/or function to any of the valves described herein. The valve 1350 can have a first configuration in which the first tube 1302 is in fluid communication with the fourth tube 1316 such that fluid can flow from the intravenous tubing 1397, through the patient intravenous port 1312, through the fourth tube 1316, through the valve 1350, through the first tube 1302, through the fluid inlet 1345, and into the reservoir of the syringe 1340. In the first configuration of the valve 1350, the third tube 1304B can be fluidically isolated from the fourth tube 1316 such that fluid flowing from the fourth tube 1316, through the valve 1350, and into the first tube 1302 is not diverted into the third tube 1304B. The valve 1350 can have a second configuration in which the third tube 1304B is in fluid communication with the fourth tube 1316 such that fluid can flow from the reservoir of the syringe 1340, through the second tube 1304A, through the blood filter 1390, through the third tube 1304B, through the valve 1350, through the fourth tube 1316, through the patient intravenous port 1312, through the intravenous tubing 1397, and into the patient's vasculature. In the second configuration of the valve 1350, the first tube 1302 can be fluidically isolated from the fourth tube 1316 such that fluid flowing from the third tube 1304B, through the valve 1350, and into the fourth tube 1316 is not diverted into the first tube 1302. The valve 1350 can have a third configuration in which both the first tube 1302 and the third tube 1304B are fluidically isolated from the fourth tube 1316. The valve 1350 can be configured to be transitioned between the first configuration, the second configuration, and the third configuration via manual manipulation (e.g., via a rotation of a lever of the valve 1350).

To prepare the system 1300, the reservoir of the syringe 1340 can be filled with medicament and anticoagulant. The valve 1350 can be arranged in the third configuration such that the medicament and anticoagulant are isolated from the fourth tube 1316. In use, the patient intravenous tubing 1397 can be coupled to the intravenous tubing such that the fourth tube 1316 is in fluid communication with the intravenous tubing 1397. The valve 1350 can then be transitioned from the third configuration to the first configuration such that the fourth tube 1316 is in fluid communication with the first tube 1302. The plunger 1343 can be drawn away from the fluid inlet 1345 such that blood is drawn from the patient's vasculature, through the fourth tube 1316, through the valve 1350, through the first tube 1302, through the fluid inlet 1345, and into the reservoir of the syringe 1340. The blood can combine with the medicament and the anticoagulant within the reservoir to form a combined substance. The valve 1350 can then be transitioned to the second configuration such that the third tube 1304B is in fluid communication with the fourth tube 1316. The plunger 1343 can then be pushed toward the fluid outlet 1346 such that the combined substance is expelled from the reservoir through the fluid outlet, through the second tube 1304A, through the blood filter 1390, through the third tube 1304B, through the valve 1350, through the fourth tube 1316, through the patient intravenous port 1312, through the intravenous tubing 1397, and into the patient's vasculature. The fluid flow rate from the reservoir can be the same or similar to the fluid flow rate from any of the reservoirs described herein.

In some embodiments, rather than including a valve 1350, the system 1300 can include Y-type tubing (e.g., tubing in the shape of a "Y") and any suitable number of clamps. For example, the tubing can include a distal tubing portion, a first proximal tubing portion, and a second proximal tubing portion. The tubing portions can be integrally formed or connected via connectors (e.g., a Y-connector). Each of the distal tubing portion, the first proximal tubing portion, and the second proximal tubing portion can be in fluid communication with one another. The first proximal tubing portion can be coupled to the fluid inlet 1345 of the syringe 1340 and the second proximal tubing portion can be coupled to the fluid outlet 1346 of the syringe 1340. A first clamp can be disposed on the first proximal tubing portion and a second clamp can be disposed on the second proximal tubing portion. Each of the first clamp and the second clamp can be transitioned between open and closed configurations. The first clamp can allow fluid to flow through the first proximal tubing portion in an open configuration and can prevent fluid to flow through the first proximal tubing portion in a closed configuration (e.g., by clamping the sidewalls of the first proximal tubing portion closed). The second clamp can allow fluid to flow through the second proximal tubing portion in an open configuration and can prevent fluid to flow through the second proximal tubing portion in a closed configuration (e.g., by clamping the sidewalls of the second proximal tubing portion closed). In some embodiments, the second proximal tubing portion can be coupled to the fluid outlet 1346 via a blood filter such as the blood filter 1390. In some embodiments, the second proximal tubing portion can be coupled to a Y-connector connecting the first proximal tubing portion, the distal tubing portion, and the second proximal tubing portion via a blood filter such as the blood filter 1390. In some embodiments, the blood filter is a 22 micron in-line filter.

In use, the patient intravenous tubing 1397 can be coupled to the intravenous tubing 1397 with the first clamp closed and the second clamp closed such that both the fluid inlet 1345 and the fluid outlet 1346 are fluidically isolated from the distal tubing portion and the intravenous tubing 1397. The first clamp can then be opened such that the distal tubing portion is in fluid communication with the fluid inlet 1345 via the first proximal tubing portion. With the second clamp closed to obstruct the fluid path through the second proximal tubing portion, the plunger 1343 can be drawn away from the fluid inlet 1345 such that blood is drawn from the patient's vasculature, through the intravenous tubing 1397, through the distal tubing portion, through the first proximal tubing portion, and into the reservoir of the syringe 1340. The blood can combine with the medicament and the anticoagulant within the reservoir to form a combined substance. The first clamp can then be closed and the second clamp opened such that the fluid path through the first proximal tubing portion is obstructed and fluid can flow through the second proximal tubing portion. The plunger 1343 can then be pushed toward the fluid outlet 1346 such that the combined substance is expelled from the reservoir through the fluid outlet 1346, through the second proximal tubing portion, through the optional blood filter, through the distal tubing portion, through the intravenous tubing 1397, and into the patient's vasculature. The fluid flow rate from the reservoir can be the same or similar to the fluid flow rate from any of the reservoirs described herein.

In some embodiments, rather than using a syringe having an inlet and a separate outlet, a system can include a syringe having an opening that can be used as an inlet and an outlet. The syringe can be coupled to a fluid path (e.g., any suitable tubes and connectors) that is configured to be coupled to the vasculature of a patient via a fluid access port or a needle. The fluid path can include a filter device having a filter that can be transitioned (e.g., rotated, slid, shifted, or otherwise moved) in and out of the fluid path. In some embodiments, the filter can be a 22 micron in-line filter. In some embodiments, the filter can be any of the filters (e.g., blood filters) described herein. The filter device can have a first open end and a second open end. In a first configuration of the filter device, the filter can be positioned so as not to obstruct the flow of fluid from the first open end to the second open end such that fluid can flow freely through the filter device without traveling through the filter. In a second configuration of the filter device, the filter can be moved into a position in which the filter obstructs the flow from the first open end to the second open end such that fluid traveling through the filter device must pass through the filter. In some embodiments, the filter can be snapped into place in the second configuration (e.g., via applying pressure on an exterior of the filter device to move the filter). The syringe can be prefilled with anticoagulant and medicament similarly to the syringe 1340 described above. In use, with the filter device in the first configuration, a plunger of the syringe can be pulled to draw blood from a patient, through the filter device, and into a reservoir of the syringe. The fluid line from the patient to the syringe can be flushed with saline. After the blood has mixed with the anticoagulant and medicament to form a combined substance, the filter device can be transitioned to the second configuration. The plunger of the syringe can then be pressed to push the combined substance out of the reservoir, through the filter of the filter device, and back into the patient's vasculature.

Figure 43:
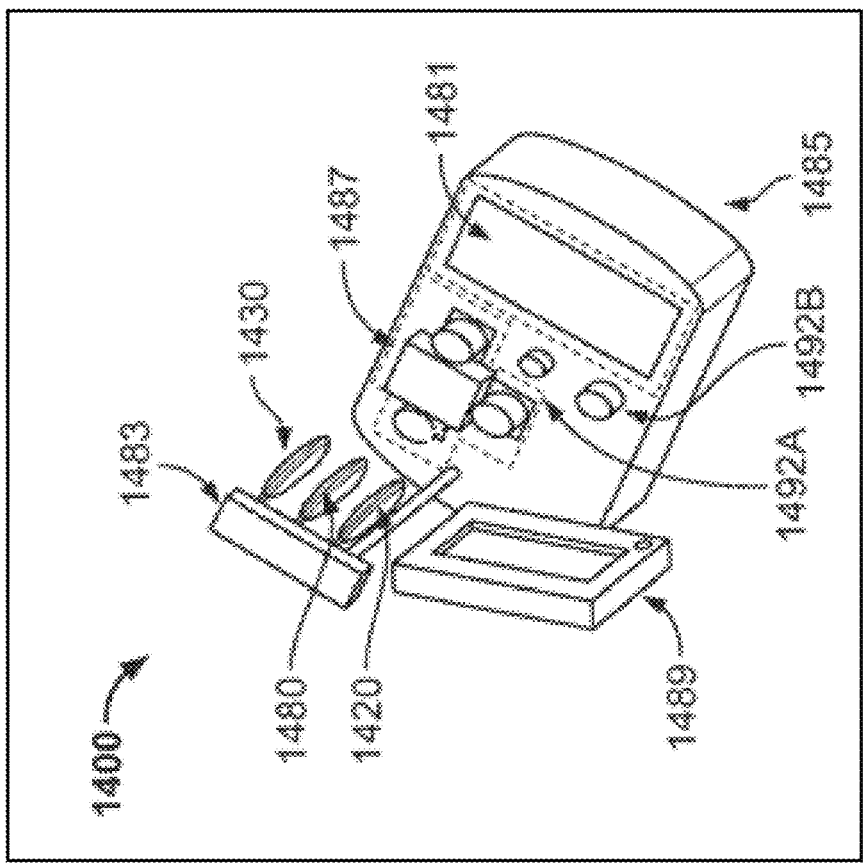
FIGS. 42 and 43 are perspective views of an example system, according to an embodiment.
Figure 42:
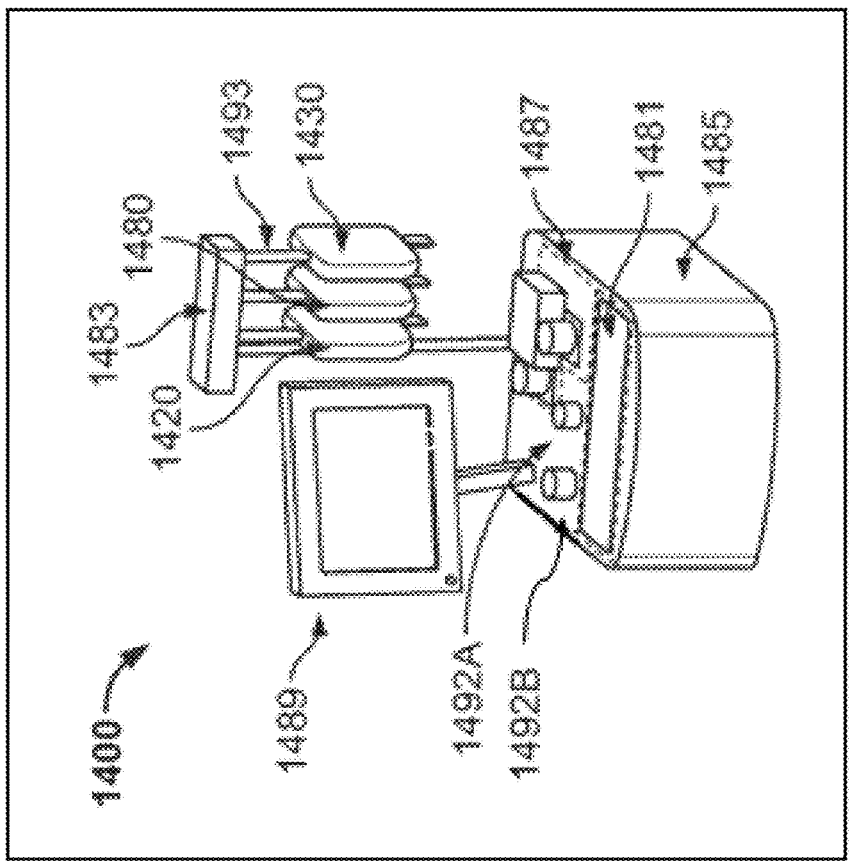

In some embodiments, rather than being manually operated, a system can be automated or semi-automated. For example, as shown in FIGS. 42 and 43, which are perspective views of a system 1400, the system 1400 includes a base 1485, a support 1493, and a display screen 1489. The support 1493 extends above the base 1485. A set of fluid bags can be hung from the support 1493. The set of fluid bags can include a first fluid bag 1420, a second fluid bag 1480, and a third fluid bag 1430. As shown in FIG. 42, in some embodiments, the first fluid bag 1420, the second fluid bag 1480, and the third fluid bag 1430 can be hung from a set of scales 1493 configured to measure the weight of each of the first fluid bag 1420, the second fluid bag 1480, and the third fluid bag 1430 during operation of the system 1400.

The first fluid bag 1420 can include anticoagulant, the second fluid bag 1480 can include saline, and the third fluid bag 1430 can include medicament. The anticoagulant can include any suitable anticoagulant, such as any of the anticoagulants described herein (e.g., ACD-A). The medicament can include any suitable medicament, such as any of the medicaments described herein.

The base 1485 can include an air detector 1492A, a clamp 1492B, a cassette/pumping assembly 1487, and a mixing module 1481. Although not shown in FIGS. 42 and 43, the first fluid bag 1420, the second fluid bag 1480, and the third fluid bag 1430 can each be coupled to the cassette/pumping assembly 1487 via fluid lines (e.g., fluid tubes and connectors). Additionally, the cassette/pumping assembly 1487 can be coupled to a patient's vasculature via a fluid line (e.g., fluid tubes and connectors). The air detector 1492A can be fluidically coupled to the fluid line coupled to the patient's vasculature and configured to monitor the fluid line for air during infusion through the fluid line from the cassette/pumping assembly 1487. The clamp 1492 can be coupled to the fluid line coupled to the patient's vasculature and can be configured to transition from an open configuration to a closed configuration. In the open configuration of the clamp 1492, fluid can travel through the fluid line. In the closed configuration of the clamp 1492, the clamp 1492 can squeeze the fluid line (e.g., sidewalls of tubing of the fluid line) to obstruct flow through the fluid line. In an emergency, for example, the clamp 1492 can be transitioned from the open configuration to the closed configuration to fluidically isolate the patient's vasculature from the system 1400.

Figure 44:
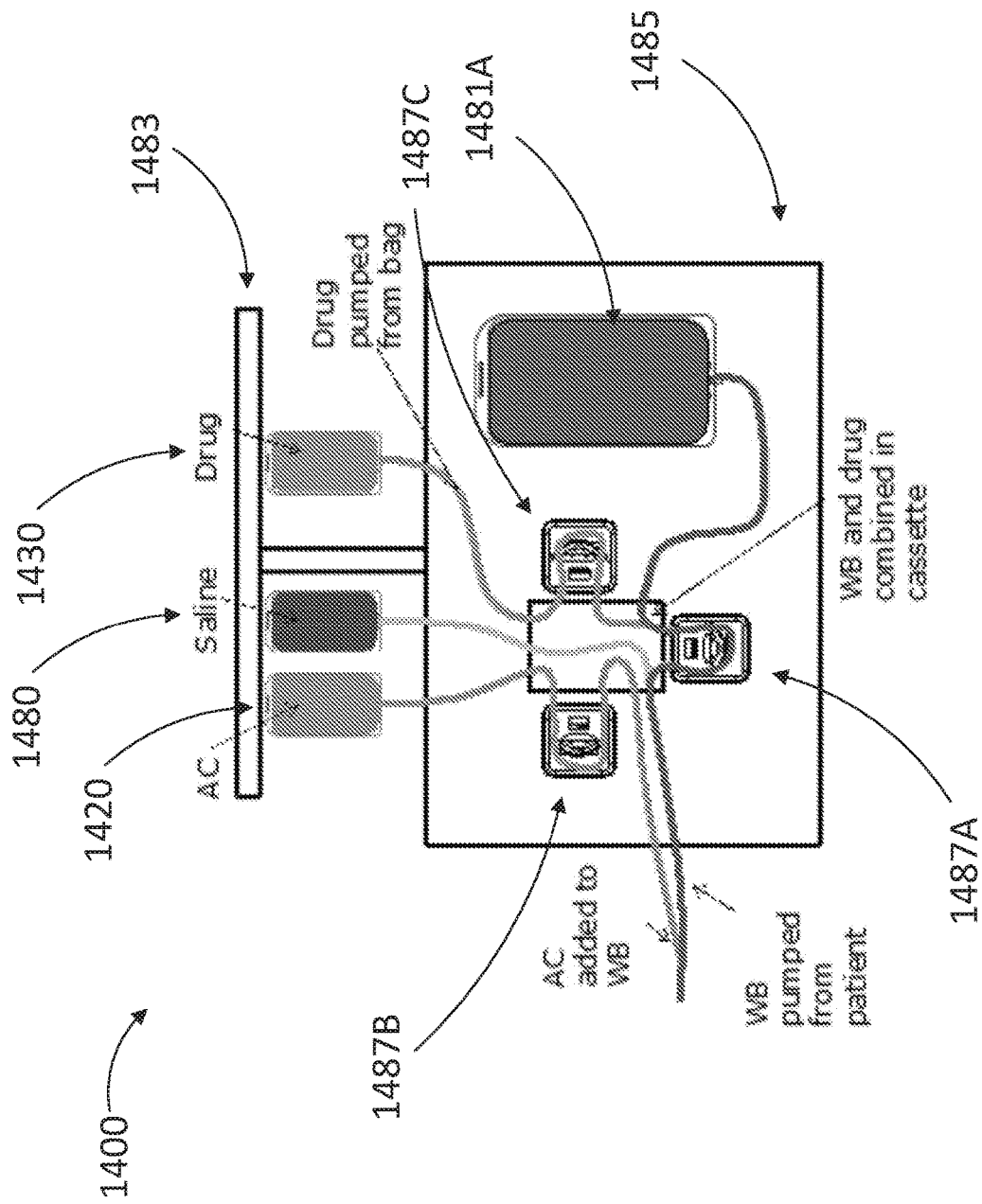
FIGS. 44-46 of schematic illustrations of the example system of FIGS. 42 and 43 in various stages of operation, according to an embodiment.
Figure 45:
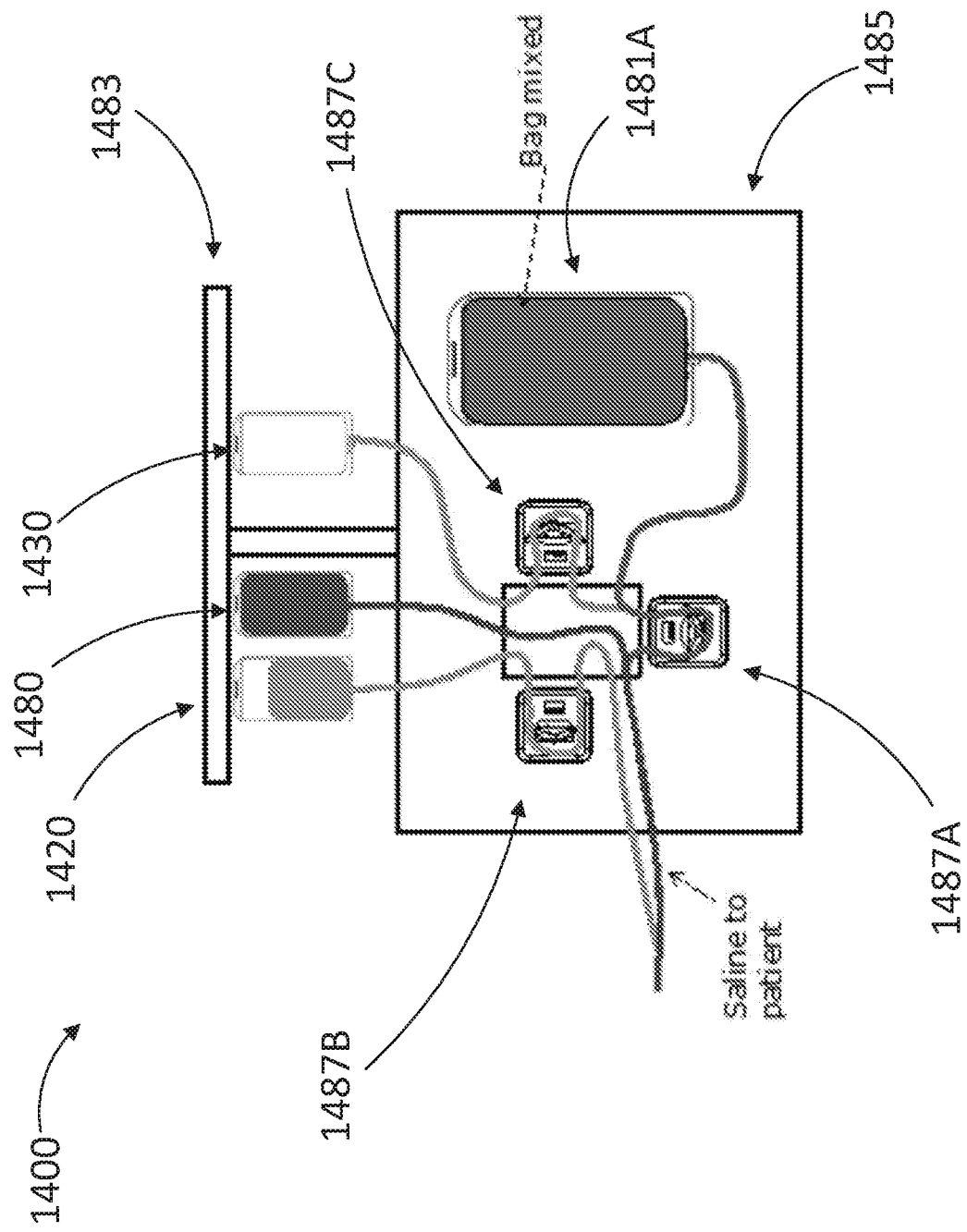
Figure 46:
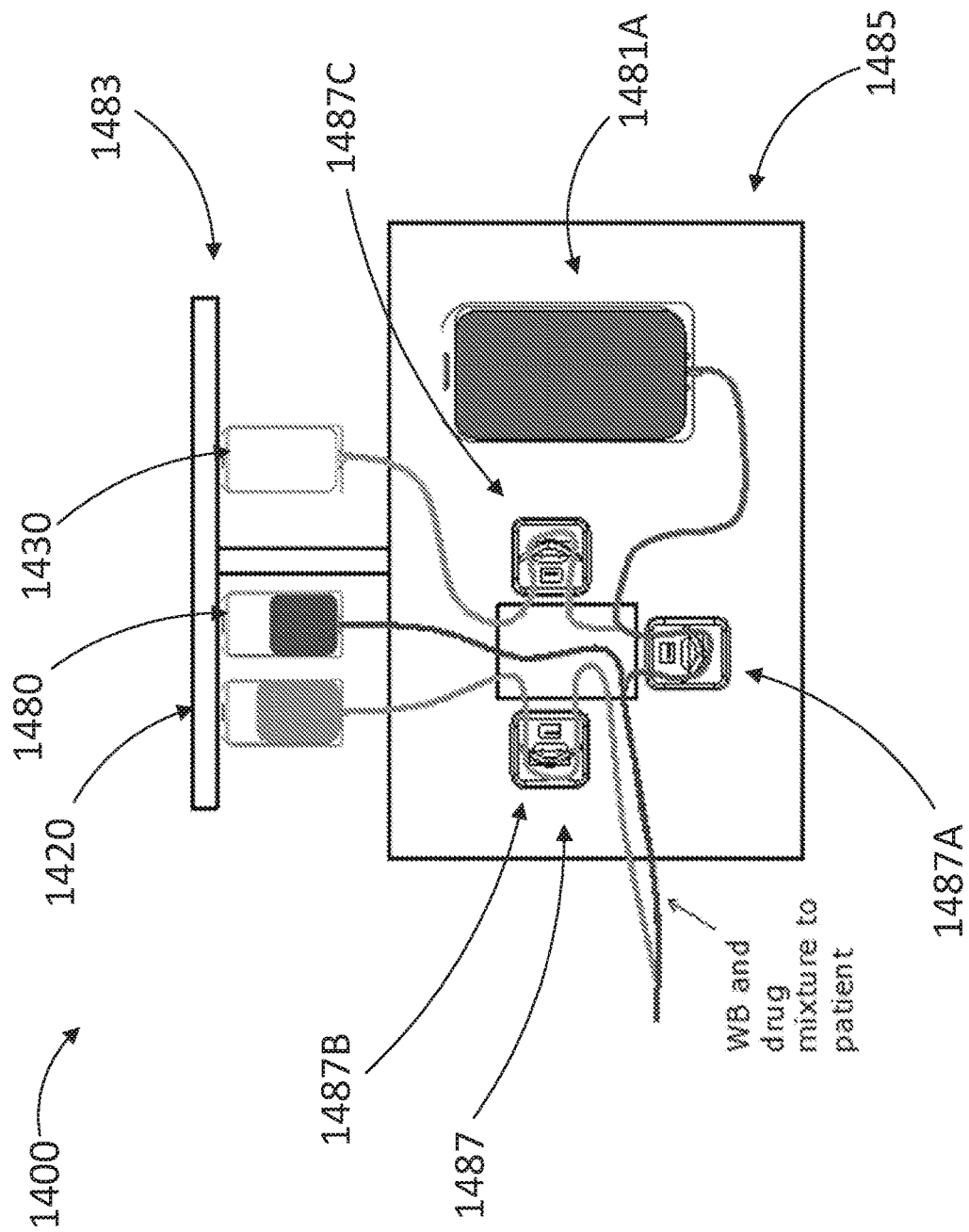

FIGS. 44-46 are various schematic illustrations of the system 1400 in various stages of operation. As shown in FIG. 44, the cassette/pumping assembly 1487 can include a first cassette 1487A, a second cassette 1487B, and a third cassette 1487C. The mixing module 1481 can include a fourth fluid bag 1481A. Each of the first cassette 1487A, the second cassette 1487B, and the third cassette 1487C can include a cover (e.g., a transparent plastic cover) and a pump tube having a first end and a second end. Each of the first cassette 1487A, the second cassette 1487B, and the third cassette 1487C can be configured to be engaged with a respective a rotor assembly and motor of the cassette/pumping assembly 1487 to form a peristaltic pump such that fluid flow through the pump tubes of the first cassette 1487A, the second cassette 1487B, and the third cassette 1487C can be controlled by the respective rotor assembly and motor base. The system 1400 can include a control assembly including a processor (e.g., a microprocessor) and a memory. Each of the motors of the cassette/pumping assembly 1487 can be operated under the control of the processor such that the rate of fluid flow through each of the first cassette 1487A, the second cassette 1487B, and the third cassette 1487C can be controlled by operating the speed of each of the respective motors.

The first end of the pump tube of the first cassette 1487A can be configured to be fluidically coupled to the patient's vasculature via a fluid line (e.g., including one or more tubes and connectors). For example, the fluid line can include a tube coupled to an existing intravenous port of the patient. The second end of the pump tube of the first cassette 1487A can be configured to be fluidically coupled to the fourth fluid bag 1481A of the mixing module 1481 via one or more tubes and connectors.

The first end of the pump tube of the second cassette 1487B can be configured to be fluidically coupled to the first fluid bag 1420 via a fluid line (e.g., a tube having a spike to spike the first fluid bag 1420). The fluid line can include an anti-microbial filter. The second end of the pump tube of the second cassette 1487B can be configured to be fluidically coupled to the fluid line from the patient to the first cassette 1487A.

The first end of the pump tube of the third cassette 1487C can be configured to be fluidically coupled to the third fluid bag 1430 via a fluid line (e.g., a tube having a spike to spike the third fluid bag 1430). The fluid line can include an anti-microbial filter. The second end of the pump tube of the third cassette 1487C can be configured to be fluidically coupled to the fluid path from the first cassette 1487A to the fourth fluid bag 1481A.

As shown in FIG. 44, after the system 1400 has been coupled to a patient's vasculature (e.g., via being coupled to an existing port or via a needle coupled to the patient's vasculature), the cassette/pumping assembly 1487 can operate the first cassette 1487A to draw a predetermined volume of whole blood from the patient's vasculature and pump the whole blood into the fourth fluid bag 1481A. The whole blood can be drawn at a predetermined rate (e.g., a rate selected by the operator). For example, the flow rate of the whole blood drawn into the system 1400 can be between about 20 mL/min and about 100 mL/min. In some embodiments, the flow rate of the whole blood during the drawing process can be adjusted by an operator of the system 1400 during the procedure.

The cassette/pumping assembly 1487 can operate the second cassette 1487B to draw a predetermined volume of anticoagulant from the first fluid bag 1420 and pump the anticoagulant into the fluid line transporting the whole blood to the fourth fluid bag 1481A by the first cassette 1481A. The second cassette 1487B can be operated by a rotor assembly and motor of the cassette/pumping assembly 1487 to pump anticoagulant into the fluid line coupled to the first cassette 1487A at a first predetermined flow rate and the first cassette 1487A can be configured to draw the mixture of whole blood and anticoagulant at a second predetermined flow rate such that the mixture of whole blood and anticoagulant in the fourth fluid bag 1481A has a predetermined or target ratio of whole blood to anticoagulant (e.g., 10:1). The weight of the first fluid bag 1420 can be monitored via the scales of the set of scales 1493 from which the first fluid bag 1420 is suspended.

The cassette/pumping assembly 1487 can operate the third cassette 1487C to draw a predetermined volume of medicament from the third fluid bag 1430 and add the medicament to the whole blood and anticoagulant transported to the fourth fluid bag 1481A by the first cassette 1481A. The weight of the third fluid bag 1480 can be monitored via the scales of the set of scales 1493 from which the third fluid bag 1480 is suspended.

The mixing module 1481 (shown in FIGS. 42 and 43) can be configured to incubate and/or mix the anticoagulant, whole blood, and medicament within the fourth fluid bag 1481A. The mixing module 1481 can be configured to operate for a predetermined amount of time. The mixing can be performed sufficiently gently to not cause hemolysis beyond a predefined threshold safety level. As shown in FIG. 45, while the contents of the fourth fluid bag 1481A are being mixed, the cassette/pumping assembly 1487 can provide saline from the second fluid bag 1480 to the patient's vasculature (e.g., to keep the patient's vein open). For example, a line from the second fluid bag 1480 can be unclamped such that saline can drip from the second fluid bag 1480 to the patient. The weight of the second fluid bag 1480 can be monitored via the scales of the set of scales 1493 from which the second fluid bag 1480 is suspended.

As shown in FIG. 46, after the contents of the fourth fluid bag 1481A are sufficiently mixed, the cassette/pumping assembly 1487 can operate the first cassette 1487A to draw the contents of the fourth fluid bag 1481A from the fourth fluid bag 1481A and pump the contents to the patient's vasculature at a controlled flow rate. The system 1400 can then be decoupled from the patient.

The first cassette 1487A, the second cassette 1487B, and the third cassette 1487C can be disposable and replaceable (e.g., for each patient). Additionally, the first fluid bag 1420, the second fluid bag 1480, the third fluid bag 1430, and the fourth fluid bag 1481A can be disposable and replaceable (e.g., for each patient).

The system 1400 (e.g., the control assembly including the processor of the system 1400) can be configured to monitor a patient's draw pressure and infusion pressure (also referred to as "return pressure") during the procedure to ensure the safety of the patient and patency of the access. If the draw pressure is below a predetermined pressure limit or outside of a predetermined pressure range, the system 1400 can alert the operator (e.g., via the display screen 1489). If the draw pressure is greater than a predetermined pressure limit or outside of a predetermined pressure range, the system 1400 can alert the operator (e.g., via the display screen 1489). During infusion, the air detector 1492A can monitor the infusion line to prevent any air from being infused to the patient.

In some embodiments, the display screen 1489 can include a touch screen and/or user input buttons. The display screen 1489 can be configured to allow an operator of the system 1400 to control the operation (e.g., set or adjust flow rates through the first cassette 1487A, the second cassette 1487B, and/or the third cassette 1487C), gather information on system status and operation status, and address error conditions.

In some embodiments, the system 1400 can be configured to draw about 125 mL of whole blood and combine the whole blood with a 50 mg dose of medicament (e.g., about 25 mL of medicament) in the fourth fluid bag 1481A. In some embodiments, the system 1400 can be configured to draw a volume of whole blood and combine the whole blood with medicament in the fourth fluid bag 1481A at a ratio of five to one.

In some embodiments, a method includes drawing fluid (e.g., containing whole blood or cells such as packed red blood cells, white blood cells, or platelets) from a patient's vasculature into a first fluid reservoir. The method can be similar to any of the methods described herein and can be performed, for example, using any of the systems described herein. The fluid can combined with a first substance in the first fluid reservoir to form a second substance. The first substance can be, for example, an anticoagulant, such as any of the anticoagulants described herein. For example, in some embodiments, the first fluid reservoir can be prefilled with the first substance. In some embodiments, the first substance can be added to the first fluid reservoir after the fluid has been drawn or pumped into the first fluid reservoir. In some embodiments, the second substance can then be combined with a third substance to form a fourth substance. For example, in some embodiments, the second substance can be combined with the third substance in the first fluid reservoir by transferring the third substance to the first fluid reservoir. In some embodiments, rather than transferring the third substance to the first fluid reservoir, the second substance can be transferred to a second fluid reservoir prefilled with the third substance. The third substance can be, for example, a medicament, such as any of the medicaments described herein. The fourth substance can then be transferred to the patient's vasculature (e.g., via infusion through a patient access port). In some embodiments, prior to transferring the fourth substance to the patient's vasculature, the fourth substance can be allowed to remain in a fluid reservoir (e.g., the first fluid reservoir or the second fluid reservoir) for a duration of time (e.g., at least two minutes).

In some embodiments, only a portion of the second substance can be combined with the third substance to form the fourth substance (e.g., by transferring the portion of the second substance to a second fluid reservoir in which the third substance is prefilled or later introduced). The fourth substance can then be combined with the remainder of the second substance to form a fifth substance (e.g., by combining the fourth substance with the remaled of the second substance in the first fluid reservoir, a second fluid reservoir, or a third fluid reservoir). The fifth substance can then be transferred to the patient's vasculature (e.g., via infusion through a patient access port). In some embodiments, the portion of the second substance has a first volume and the fifth substance has a second volume, the second volume being at least about two times the size of the first volume. In some embodiments, prior to transferring the fifth substance to the patient's vasculature, the fourth substance can be allowed to remain in a fluid reservoir for a duration of time (e.g., at least two minutes).

While various embodiments have been described above, it should be understood that they have been presented by way of example only, and not limitation. Where methods described above indicate certain events occurring in certain order, the ordering of certain events can be modified. Additionally, certain of the events can be performed concurrently in a parallel process when possible, as well as performed sequentially as described above.

Where schematics and/or embodiments described above indicate certain components arranged in certain orientations or positions, the arrangement of components can be modified. While the embodiments have been particularly shown and described, it will be understood that various changes in form and details can be made. Any portion of the apparatus and/or methods described herein can be combined in any combination, except mutually exclusive combinations. The embodiments described herein can include various combinations and/or sub-combinations of the functions, components, and/or features of the different embodiments described.

The invention claimed is:

1. An apparatus for in-situ mixing, the apparatus comprising:
   a patient access subassembly;
   a first fluid reservoir comprising a first fluidic substance;
   a second fluid reservoir comprising a second fluidic substance, wherein the second fluidic substance comprises a medicament;
   a base fluidically coupled to the patient access subassembly, the first fluid reservoir, and the second fluid reservoir; and
   an assembly comprising a processor adapted to control the base to:
      receive a blood product from a patient;
      mix the blood product with the first fluidic substance to form a third fluidic substance;
      mix the third fluidic substance with the second fluidic substance to form a fourth fluidic substance; and
      transfer the fourth fluidic substance to the patient access subassembly to expel the fourth fluidic substance from the patient access subassembly and back into the patient,
   wherein the apparatus is configurable such that fluidic communication is achievable between any of the first fluid reservoir, the second fluid reservoir, and the patient access subassembly.

2. The apparatus of claim 1, where the first fluidic substance comprises an anti-coagulant.

3. The apparatus of claim 1, wherein the base comprises a cassette/pumping assembly configured to:
   draw a predetermined volume of the blood product from vasculature of the patient at a predetermined rate;
   draw the first fluidic substance into a mixing module configured to mix the blood product with the first fluidic substance to form the third fluidic substance; and
   draw the third fluidic substance into the mixing module configured to mix the third fluidic substance with the second fluidic substance to form the fourth fluidic substance.

4. The apparatus of claim 1, wherein the apparatus is automated or semi-automated.

5. The apparatus of claim 1,
   wherein the apparatus further comprises a filter, and
   wherein the filter is configured to trap microbubbles and remove debris from the fourth fluidic substance prior to expelling the fourth fluidic substance from the patient access subassembly and back into the patient.

6. The apparatus of claim 5, wherein the filter comprises a pore size in a range of about 150 microns to about 260 microns.

7. The apparatus of claim 1, wherein the processor of the assembly is further configured to control the base to:
   manipulate the assembly such that the first fluid reservoir is fluidically isolated from the patient access subassembly and the first fluid reservoir is in fluidic communication with the second fluid reservoir;
   transfer a portion of the third fluidic substance from the first fluid reservoir into the second fluid reservoir such that the portion of the third fluidic substance and the second fluidic substance form the fourth fluidic substance;
   transfer the fourth fluidic substance from the second fluid reservoir into the first fluid reservoir such that a remainder of the third fluidic substance and the fourth fluidic substance form a fifth fluidic substance;
   manipulate the assembly such that the first fluid reservoir is in fluidic communication with the patient access subassembly; and transfer the fifth fluidic substance to the patient access subassembly to expel the fifth fluidic substance from the patient access subassembly and back into the patient.

8. The apparatus of claim 7, wherein the processor of the assembly is further configured to control the base to maintain the fifth fluidic substance in the first fluid reservoir for a time period prior to transferring the fifth fluidic substance to the patient access subassembly to expel the fifth fluidic substance from the patient access subassembly and back into the patient.

9. The apparatus of claim 8, wherein the time period comprises at least two minutes.

10. The apparatus of claim 3, wherein the cassette/pumping assembly is coupled to vasculature of the patient via a fluid line.

11. The apparatus of claim 10, wherein the base comprises an air detector and a display screen.

12. The apparatus of claim 11, wherein the air detector is coupled to the fluid line and is configured to:
monitor the fluid line for air during the transfer of the fourth fluidic substance to the patient access subassembly to expel the fourth fluidic substance from the patient access subassembly and back into the patient; and
in response to a detection of the air during the transfer, transmit an alert to the display screen.

13. The apparatus of claim 3, wherein the cassette/pumping assembly is configured to draw a predetermined volume of the blood product from vasculature of the patient at a predetermined rate.

14. The apparatus of claim 13, wherein the predetermined rate is in a range of about 20 mL/min to about 100 mL/min.

15. The apparatus of claim 3, wherein at least one cassette of the cassette/pumping assembly is disposable and replaceable.

16. The apparatus of claim 3, wherein the blood product comprises a volume of about 125 mL of blood.

17. The apparatus of claim 3, wherein the blood of the blood product comprises whole blood.

18. The apparatus of claim 1, where the first fluidic substance comprises an antioxidant.

19. The apparatus of claim 18, wherein the antioxidant comprises vitamin C or N-acetylcysteine.

20. The apparatus of claim 2, wherein the anti-coagulant is selected from the group consisting of: ACD-A, ACD-B, EDTA, and heparin.

21. The apparatus of claim 1, wherein the medicament is selected from the group consisting of: 2-Bromo-1-(3,3-dinitroazetidin-1-yl)ethanone, a derivative of 2-Bromo-1-(3,3-dinitroazetidin-1-yl)ethenone, a dinitroazetidine, propofol, nitric oxide, a nitric oxide donor, ozone, and a chemotherapy drug.

22. The apparatus of claim 21, wherein the medicament comprises the chemotherapy drug.

23. The apparatus of claim 22, wherein the chemotherapy drug is selected from the group consisting of: an antitumor platinum coordination complex, an antimetabolite, a mitotic inhibitor, an anticancer antibiotic, a topoisomerase I inhibitor, a topoisomerase II inhibitor, a proteasome inhibitor, a histone deacetylase inhibitor, a nitrogen mustard alkylating agent, a nitrosourea alkylating agent, a nonclassical alkylating agent, an estrogen antagonist, an androgen antagonist, a mTOR inhibitor, and a tyrosine kinase inhibitor.

* * * * *